(12) United States Patent
Arnold et al.

(10) Patent No.: US 11,865,137 B2
(45) Date of Patent: Jan. 9, 2024

(54) SULFATED OLIGOSACCHARIDES HAVING ANTI-INFLAMMATORY ACTIVITY

(71) Applicants: The University of North Carolina at Chapel Hill, Chapel Hill, NC (US); THE RESEARCH FOUNDATION FOR THE STATE UNIVERSITY OF NEW YORK, Amherst, NY (US)

(72) Inventors: Katelyn Arnold, Chapel Hill, NC (US); Ding Xu, East Amherst, NY (US); Yongmei Xu, Durham, NC (US); Rafal Pawlinski, Chapel Hill, NC (US); Jian Liu, Chapel Hill, NC (US)

(73) Assignees: The University of North Carolina at Chapel Hill, Chapel Hill, NC (US); The Research Foundation for the State University of New York, Amherst, NY (US)

( * ) Notice: Subject to any disclaimer, the term of this patent is extended or adjusted under 35 U.S.C. 154(b) by 123 days.

(21) Appl. No.: 16/761,159

(22) PCT Filed: Nov. 5, 2018

(86) PCT No.: PCT/US2018/059152
§ 371 (c)(1),
(2) Date: May 1, 2020

(87) PCT Pub. No.: WO2019/090203
PCT Pub. Date: May 9, 2019

(65) Prior Publication Data
US 2021/0169923 A1 Jun. 10, 2021

Related U.S. Application Data

(60) Provisional application No. 62/581,443, filed on Nov. 3, 2017.

(51) Int. Cl.
*A61K 31/727* (2006.01)
(52) U.S. Cl.
CPC .................. *A61K 31/727* (2013.01)
(58) Field of Classification Search
None
See application file for complete search history.

(56) References Cited

U.S. PATENT DOCUMENTS

| | | |
|---|---|---|
| 4,554,101 A | 11/1985 | Hopp |
| 4,865,870 A | 9/1989 | Hu et al. |
| 5,527,785 A * | 6/1996 | Bevilacqua .......... A61K 31/715 514/56 |
| 5,543,403 A | 8/1996 | Petitou et al. |
| 5,817,487 A | 10/1998 | Kobayashi et al. |
| 5,834,282 A | 11/1998 | Habuchi et al. |
| 5,935,824 A | 8/1999 | Sgarlato |
| 6,255,088 B1 | 7/2001 | Wong et al. |
| 6,861,254 B1 | 3/2005 | Rosenberg et al. |
| 7,101,859 B2 | 9/2006 | Yedgar et al. |
| 7,531,338 B2 | 5/2009 | Liu |
| 9,951,149 B2 | 4/2018 | Liu et al. |
| 10,286,047 B2 | 5/2019 | Spirig et al. |
| 11,203,772 B2 | 12/2021 | Xu et al. |
| 11,633,424 B2 | 4/2023 | Liu et al. |
| 2003/0083294 A1 | 5/2003 | Sullenger |
| 2003/0099967 A1 | 5/2003 | Deangelis |
| 2004/0191870 A1 | 9/2004 | Rosenberg et al. |
| 2004/0259142 A1 | 12/2004 | Chai et al. |
| 2005/0090601 A1 | 4/2005 | Dadalas et al. |
| 2005/0090661 A1 | 4/2005 | Asari et al. |
| 2005/0101532 A1 | 5/2005 | Yang et al. |
| 2005/0191288 A1 | 9/2005 | Bennett et al. |
| 2005/0255562 A1 | 11/2005 | Rosenberg et al. |
| 2005/0282775 A1 * | 12/2005 | Kennedy .............. A61K 31/727 514/56 |
| 2006/0165673 A1 | 7/2006 | Liu |
| 2006/0172931 A1 | 8/2006 | San Antonio et al. |
| 2006/0229276 A1 | 10/2006 | Hook et al. |
| 2008/0109236 A1 | 5/2008 | DeAngelis |
| 2009/0035787 A1 | 2/2009 | Liu |
| 2009/0155851 A1 | 6/2009 | Sugiura et al. |
| 2009/0197308 A1 | 8/2009 | Liu |
| 2010/0125052 A1 | 5/2010 | Lu et al. |

(Continued)

FOREIGN PATENT DOCUMENTS

| | | |
|---|---|---|
| CN | 105452479 B | 5/2021 |
| EP | 0 394 971 | 10/1990 |

(Continued)

OTHER PUBLICATIONS

Arnold, Biomedicines 2020, 8, 0503. (Year: 2020).*
Frank, Thromb Haemost 2006; 96:802-6. (Year: 2006).*
Advisory Action corresponding to U.S. Appl. No. 13/996,930 dated Dec. 9, 2016.
Aikawa et al., "Molecular Cloning and Expression of a Third Member of the Heparan Sulfate/Heparin GlcNAc N-Deacetylase/N-Sulfotransferase Family," The Journal of Biological Chemistry, vol. 274, No. 5, pp. 2690-2695 (Jan. 29, 1999).
Aikawa et al., "Multiple Isozymes of Heparan Sulfate/Heparin GlcNAc N-Deacetylase/GlcN N-Sulfotransferase," The Journal of Biological Chemistry, vol. 276, No. 8, pp. 5876-5882 (Feb. 23, 2001).

(Continued)

*Primary Examiner* — Layla D Berry
(74) *Attorney, Agent, or Firm* — Jenkins, Taylor & Hunt P.A.

(57) ABSTRACT

Provided herein are small molecule compounds, including non-anticoagulant heparan sulfate oligosaccharide molecules, having anti-inflammatory properties and capable of interacting with high mobility group box 1 (HMGB1) proteins in a manner sufficient to affect an interaction between the HMGB1 protein and a receptor for advanced glycation end products (RAGE). Also provided herein are methods of treating Paracetamol (APAP) overdose in subjects.

24 Claims, 15 Drawing Sheets

(56) References Cited

U.S. PATENT DOCUMENTS

| | | | |
|---|---|---|---|
| 2010/0298260 A1* | 11/2010 | Sundaram | C12P 19/04 536/123.13 |
| 2010/0305022 A1 | 12/2010 | Shriver | |
| 2011/0054236 A1 | 3/2011 | Yang et al. | |
| 2011/0281819 A1 | 11/2011 | Kakehi et al. | |
| 2012/0064044 A1 | 3/2012 | Egan | |
| 2012/0308546 A1 | 12/2012 | Kizhakkedathu et al. | |
| 2012/0322114 A1 | 12/2012 | Liu et al. | |
| 2012/0322760 A1 | 12/2012 | Fier et al. | |
| 2013/0022647 A1 | 1/2013 | Kizhakkedathu et al. | |
| 2013/0296540 A1 | 11/2013 | Xu et al. | |
| 2013/0338097 A1 | 12/2013 | Stephens et al. | |
| 2016/0122446 A1 | 5/2016 | Liu et al. | |
| 2021/0137967 A1 | 5/2021 | Liu et al. | |
| 2021/0260098 A1 | 8/2021 | Liu et al. | |
| 2021/0332076 A1 | 10/2021 | Liu et al. | |
| 2022/0265699 A1 | 8/2022 | Arnold et al. | |
| 2022/0416486 A1 | 12/2022 | Yamaguchi | |

FOREIGN PATENT DOCUMENTS

| | | |
|---|---|---|
| EP | 0 565 863 | 10/1993 |
| JP | 6670235 | 3/2020 |
| WO | WO 89/04328 | 5/1989 |
| WO | WO93/05167 | 3/1993 |
| WO | WO 96/14425 | 5/1996 |
| WO | WO2003018598 | 3/2003 |
| WO | WO 2004/005475 A2 | 1/2004 |
| WO | WO 2004/009642 | 1/2004 |
| WO | WO 2004/017910 A2 | 3/2004 |
| WO | WO2005/118609 | 12/2005 |
| WO | WO 2006/124801 | 11/2006 |
| WO | WO 2009/079693 A1 | 7/2009 |
| WO | WO 2012/088416 A2 | 6/2012 |
| WO | WO 2012/116048 | 8/2012 |
| WO | WO 2014/204929 | 12/2014 |
| WO | WO 2018/165656 | 9/2018 |
| WO | WO 2019/010216 A1 | 1/2019 |
| WO | WO 2019/246264 | 12/2019 |
| WO | WO 2021/097345 A1 | 5/2021 |

OTHER PUBLICATIONS

Alexander et al., "Syndecan-1 is required for Wnt-1-induced mammary tumorigenesis in mice," Nat. Genet., vol. 25, pp. 329-332 (2000).
Altschul et al., "Basic Local Alignment Search Tool," J. Mol Bio., vol. 1215, pp. 403-410 (1990).
Antoine et al., "Mechanistic biomarkers provide early and sensitive detection of acetaminophen-induced acute liver injury at first presentation to hospital." Hepatology vol. 58, pp. 777-787 (2013).
Applicant-Initiated Interview Summary corresponding to U.S. Appl. No. 13/996,930 dated Jan. 23, 2017.
Arnold et al., "Design of anti-inflammatory heparan sulfate to protect against acetaminophen-induced acute liver failure." Sci. Transl. Med., vol. 12, Article ID eaav8075 (2020).
Arnold et al., "Synthetic anticoagulant heparan sulfate attenuates liver ischemia reperfusion injury." Sci. Reports, vol. 10, Article No. 17187 (10 pages) (2020).
Arungundram, S.; Al-Mafraji, K.; Asong, J.; Leach III, F. E.; Amster, I. J.; Venot, A.; JE, T.; Boons, G. J. "Modular Synthesis of Heparan Sulfate Oligosaccharides for Structure-Activity Relationship Studies," J. Am. Chem. Soc. 2009, 131, 17394.
Atha et al., "Contribution of Monosaccharide Residues in Heparin Binding to Antithrombin III," Biochemistry, vol. 24, pp. 6723-6729 (1985).
Avci et al., "Synthetic oligosaccharides as heparin-mimetics displaying anticoagulant properties," Curr. Pharm. Des., vol. 9, pp. 2323-2335 (2003).
Axelsson et al., "Inactivation of heparan sulfate 2-O-sulfotransferase accentuates neutrolphil infiltration during acute inflammation in mice." Blood, vol. 120, pp. 1742-1751 (2012).

Bailey et al., "Delays during the administration of acetylcysteine for the treatment of paraacetamol overdose." Br. J. Clin. Pharmacol. vol. 62, pp. 1358-1363 (2016).
Balagurunathan et al., Chemoenzymatic Synthesis of Classical and Non-classical Anticoagulant Heparan Sulfate Polysaccharide, J. Biol. Chem., vol. 278, pp. 52613-52621 (2003).
Balagurunathan et al., Enzymatic synthesis of antithrombin III-binding heparan sulfate pentasaccharide, Nat. Biotechnol., vol. 21, pp. 1343-1346 (2003).
Baleux et al. (2009) Nat. Chem. Biol., 5, 743-748.
Beeson et al., "Inhibition of Binding of Malaria-Infected Erythrocytes by a Tetradecasaccharide Fraction from Chondroitin Sulfate A," Infection and Immunity vol. 66 No. 7 pp. 3397-3402 (Year: 1998).
Belot, F. et al., "Syntheses of chondroitin 4- and 6-sulfate pentasaccharide derivatives having a methyl beta-D-glucopyranosiduronic acid at the reducing end" Carbohyd. Res., vol. 326, pp. 88-97. (Year: 2000).
Bernfield et al., "Heparin-Binding Proteins," Annu. Rev. Biochem., vol. 68, pp. 729-777 (1999).
Bianchi et al., "High-mobility group box 1 protein orchestrates responses to tissue damage via inflammation, innate and adaptive immunity, and tissue repair." Immunol. Rev. vol. 280, pp. 74-82 (2017).
Bitter et al. (1962) Anal. Biochem. 4, 330-334.
Bjornsson, Simultaneous Preparation and Quantitation of Proteoglycans by Preciptation with Alcian Blue, Anal. Biochem., vol. 210, pp. 282-291 (1993).
Blieden et al., "A perspective on the epidemiology of acetaminophen exposure and toxicity in the United States." Expert Rev. Clin. Pharmacol. vol. 7, pp. 341-348 (2014).
Bourgeaux et al., "Two-step enzymatic synthesis of UDP-N-acetylgalactosamine." Bioorg. Med. Chem. Lett., vol. 15, pp. 5459-5462 (2005).
Bowman et al., Carbohydrate sulfotransferases: medliators of extracellular Communication, Chemistry & Biology, vol. 6, pp. R9-R22 (Jan. 1999).
Bradbury et al., "Chondroitinase ABC promotes functional recovery after spinal cord injury." Nature, vol. 416, pp. 636-640 (2002).
Brinkmann V, Reichard U, Goosmann C, Fauler B, Uhlemann Y, Weiss DS, et al. Neutrophil extracellular traps kill bacteria. Science. 2004;303:1532-5.
Broun et al., "Catalytic plasticity of fatty acid modification enzymes underlying chemical diversity of plant lipids," Science, vol. 282, pp. 1315-1317 (1998).
Brown et al., "A sulfated carbohydrate epitope inhibits axon regeneration after injury." Proc. Natl. Acad. Sci. USA, vol. 109, pp. 4768-4773 (2012).
Brown et al., Drug Research, "Cardenolide analogues. 11. Improved method for the use of Fetizon's reagent in the synthesis of cardiac glycosides", vol. 31, No. 7, pp. 1059-1064 (1981).
Burkart et al., "Regeneration of PAPS for the Enzymatic Synthesis of Sulfated Oligosaccharides," J. Org. Chem., vol. 65, pp. 5565-5574 (2000).
Cai et al., "Towards the chemoenzymatic synthesis of heparan sulfate oligosaccharides: Oxidative cleavage of p. nitrophenyl group with ceric ammonium salts," Tetra. Lett., vol. 54, No. 33, pp. 4471-1474 (2013).
Capila et al., "Heparin—Protein Interactions," Angew. Chem. Int. Ed., vol. 41, pp. 390-412 (2002).
Carfi et al., "Herpes Simplex Virus Glycoprotein D Bound to the Human Receptor HveA," Molecular Cell, vol. 8, pp. 169-179 (Jul. 2001).
Cassinelli et al., "Old and new applications of non-anticoagulant heparin." International Journal of Cardiology, 212S1 pp. S14-S21 (2016).
Casu et al., Heparin-like compounds prepared by chemical modification of capsular polysaccharide from E. coli K5, Carbohydrate Research vol. 263, pp. 271-28 (1994).
Chan et al., "Regulation of PfEMP1-VAR2CSA translation by a Plasmodium translation-enhancing factor." Nature Microbiology, vol. 2, Article No. 17068 (2017).

(56) References Cited

OTHER PUBLICATIONS

Chen et al., "Enzymatic redesigning of biologically active haparan sulfate," JBC, vol. 280, No. 52, pp. 42817-42825 (2005).
Chen et al., "Using an Enzymatic Combinatorial Approach to Identify Anticoagulant Heparan Sulfate Structures," Chemistry and Biology, Current Biology, London, GB, vol. 14., No. 9, pp. 986-993 (Sep. 19, 2007).
Chen et al., "Biosynthesis of 3-O-sulfated heparan sulfate: unique substrate specificity of heparan sulfate 3-O-sulfotransferase isoform 5," Glycobiology, vol. 13, No. 11, pp. 785-794 (Nov. 2003).
Chen et al., "Sterile inflammation: sensing and reacting to damage." Nat. Immunol. vol. 10, pp. 826-837 (2010).
Chen et al., Towards De Novo Synthesis of Structure-Defined Oligosaccharides with Heparan Sulfate Biosynthetic Enzymes, PhD dissertation,pp. 1-167, (Date Created: Aug. 2008; Date Deposited: Oct. 11, 2010.).
Chen et al., "Tyrosine-Ester Sulfotransferase from Rat Liver: Bacterial Expression and Identificationn," Protein Expression Purif., vol. 3, pp. 421-426 (1992).
Chen, M., et al. (2006) Biochemistry, 45, 12358-12365.
Clark SR, Ma AC, Tavener SA, McDonald B, Goodarzi Z, Kelly MM, et al. Platelet TLR4 activates neutrophil extracellular traps to ensnare bacteria in septic blood. Nat Med. 2007;13:463-9.
Communication of European publication number and information on the application of Article 67(3) EPC corresponding to European Application No. 14812890.3 dated Mar. 31, 2016.
Communication of European publication number corresponding to European Patent application No. 20887629.2 dated Jul. 20, 2022.
Communication of the extended European search report corresponding to European Application No. 14812890.3 dated Dec. 21, 2016.
Conrad, Heparin-Binding Proteins, J. of Medicinal Chemistry, vol. 42, No. 4, pp. 777-778 (1998).
Copeland et al., "Using a 3-O-Sulfated Heparin Octasaccharide to Inhibit the Entry of Herpes Simplex Virus Type 1," Biochemistry, vol. 47, pp. 5774-5783 (2008).
Corrected Notice of Allowability corresponding to U.S. Appl. No. 16/492,858 dated Sep. 20, 2022.
Corrected Notice of Allowance corresponding to U.S. Appl. No. 16/492,858 dated Sep. 20, 2022.
Coutant et al., "2-Deoxy-2-trichloroacetamido-D-glucopyranose derivatives in oligosaccharide synthesis: from hyaluronic acid to chondroitin 4-sulfate trisaccharides" J Chem Soc Perkin Trans 1 (1995) 1573-1581 (Year: 1995).
Crowther et al., "Mechanisms responsible for the failure of protamine to inactivate low-molecular-weight heparin," British Journal of Hematology, vol. 116, pp. 178-186 (2002).
Darden, T.; York, D.; Pedersen, L. C. J. Chem. Phys. 1993, 98, 10089.
Das et al., "Synthesis of Conformationally Locked I-Iduronic Acid Derivatives: Direct Evidence for a Critical Role of the Skew-Boat 2S0 Conformer in the Activation of Antithrombin by Heparin," Chem. Eur. J., vol. 7, No. 22, pp. 4821-4834 (2001).
Davenport, "Review article: Low-molecular-weight heparin as an alternative anticoagulant to unfractionated heparin for routine outpatient haemodialysis treatments," Nephrology, vol. 14, pp. 456-461 (2009).
deAgostini, A. I.; Dong, J.-C.; de Vantery Arrighi, C.; Ramus, M.-A.; Dentand-Quadri, I.; Thanlmann, S.; Ventura, P.; Ibecheole, V.; Monge, F.; Fischer, A.-M.; HajMohammadi, S.; Shworak, N.; Zhang, L.; Zhang, Z.; Linhardt , R. J. "Human Follicular Fluid Heparan Sulfate Contains Abundant 3-O-Sulfated Chains with Anticoagulant Activity," J. Biol. Chem. 2008, 283, 28115.
Decision to Grant corresponding to Japanese Patent Application No. 2016521505 dated Feb. 3, 2020.
Decision to Grant corresponding to Japanese Patent Application No. 2019549419 dated Jul. 11, 2023.
Dementiev et al., "The ternary complex of antithrombin-anhydrothrombin-heparin reveals the basis of inhibitor specificity," Nat. Struct. Biol., vol. 11, pp. 867-863 (2004).

Dooley, T., "Cloning of the human phenol sulfotransferase gene family: three genes implicated in the metabolism of catecholamines, thyroid hormones and drugs," Chemico-Biological Interactions, vol. 109, pp. 29-41 (1998).
Dou et al., "Role of Deacetylase Activity of N-Deacetylase/N-Sulfotransferase 1 in Forming N-Sulfated Domain in Heparan Sulfate", The Journal of Biological Chemistry, vol. 290, No. 33, pp. 20427-20437 (Aug. 14, 2015).
Duncan et al., Biochim. Biophys. Acta, vol. 1671, pp. 34-43 (2004).
Edavettal et al.,, "Crystal Structure and Mutational Analysis of Heparan Sulfate 3-O-Sulfotransferase Isoform 1," J. Biol. Chem., vol. 279, No. 24, pp. 25789-25797 (Jun. 11, 2004).
Edens et al., "Gradient Polyacrylamide Gel Electrophoresis for Determination of Molecular Weights of Heparin Preparations and Low-Molecular-Weight Heparin Derivatives," J. Pharm. Sci., vol. 81, No. 8, pp. 823-827 (Aug. 1992).
Eller et al., "Automated Solid-Phase Synthesis of Chondroitin Sulfate Glycosaminoglycans." Angew. Chem. Int. Ed., vol. 52, pp. 5858-5861 (2013).
Esko et al., "Molecular diversity of heparan sulfate," J. Clin. Invest., vol. 108, pp. 169-173 (2001).
Esko et al., "Order Out of Chaos: Assembly of Ligand Binding Sites in Heparan Sulfate," Annu. Rev. Biochem., vol. 71, pp. 435-471 (2002).
European Search Report corresponding to European Patent Application No. 18764628.6 dated Dec. 2, 2020.
European Search Report corresponding to European Patent Application No. 18873131.9 dated Jul. 12, 2021.
Extended European Search Report Corresponding to European Patent Application No. 19822610.2 dated Mar. 29, 2022.
Falany, C., "Introduction: Changing view of sulfation and the cytosolic Sulfotransferases," vol. 11, The FASEB Journal, pp. 1-2 (Jan. 1997).
Feltracco et al., "Perioperative thrombotic complications in liver transplantation." World J. Gastroenterol., vol. 21, pp. 8004-8013 (2015).
Feng et al., "Characteristics Associated with Liver Graft Failure: The Concept of a Donor Risk Index." Am. J. Transplant., vol. 6, pp. 783-790 (2006).
Feyerabend et al., "Heparan sulfate C5-epimerase is essential for heparin biosynthesis in mast cells," Nat. Chem. Biol., vol. 2, No. 4, pp. 195-196 (Apr. 2006).
Fiser, A; Sali, A Methods Enzymol 2003, 374, 461.
Freeman et al., "The accumulation of circulating histones on heparan sulphate in the capillary glycocalyx of the lungs." Biomater., vol. 34, pp. 5670-5676 (2013).
Fried et al., "Designing a VAR2CSA-based vaccine to prevent placental malaria." Vaccine, vol. 33, pp. 7483-7488 (2015).
Fukuta et al., "Molecular cloning and expression of human chondroitin 6-sulfotransferase," Biochimica et Biophysica Acta, vol. 1399, pp. 57-61 (1998).
Fuster et al., The sweet and sour of cancer: glycans as novel therapeutic targets, Nat. Rev. Cancer, vol. 5, No. 7, pp. 1-27 (Jul. 2005).
Gallagher, "Heparan sulfate: growth control with a restricted sequence menu," J. Clin. Invest., vol. 108, pp. 357-361 (2001).
Gama et al., "Sulfation patterns of glycosaminoglycans encode molecular recognition and activity," Nat. Chem. Biol., vol. 2, No. 9, pp. 467-473 (Sep. 2006).
Ganey et al. "Role of the Coagulation System in Acetaminophen-Induced Hepatotoxicity in Mice." Hepatology, vol. 46(4), pp. 1177-1186 (2007).
Genbank Accession No. AAC40135 dated Jun. 17, 1998.
Genbank Accession No. BAA89247 dated Jan. 29, 2000.
Genbank Accession No. NP_005105 dated May 24, 2014.
Genbank Accession No. NP_006032 dated Feb. 26, 2014.
Genbank Accession No. NP_006033 dated Jan. 26, 2014.
Genbank Accession No. NP_056633 dated May 3, 2014.
Genbank Accession No. NP_056635 dated Mar. 3, 2014.
Goddard-Borger et al., "An Efficient, Inexpensive and Shelf-Stable Diazotransfer Reagent: Imidazole-1-sulfonyl Azide Hydrochloride." Org. Lett., vol. 9, pp. 3797-3800 (2007).

(56) References Cited

OTHER PUBLICATIONS

Gribskov, M., Burgess,R.R. and Devereux,J. (1986) Nucl. Acids Res. 14, 327-334.

Guerrini et al., "Oversulfated chondroitin sulfate is a contaminant in heparin associated with adverse clinical events," Nat. Biotechnol., vol. 26, No. 6, pp. 669-675 (Jun. 2008).

Guerrini, M.; Elli, S.; Mourier, P.; Rudd, T.R.; Gaudesi, D.; Casu, B.; Boudier, C.; Torri, G.; Viskov, C. "An unusual antithrombin-binding heparin octasaccharide with an additional 3-O-sulfated glucosamine in the active pentasaccharide sequence," Biochem. J. 2013, 449, 343.

Guerrini, M.; Mourier, P. A.; Torri, G.; Viskov, C. "Antithrombin-binding oligosaccharides: structural diversities in a unique function?," Glycoconj. J. 2014, 31, 409.

Guimond et al.,"Fibroblast growth factor receptor signaling is dictated by specific heparin sulphate saccharides," Curro. Biol., vol. 9, No. 22 pp. 1343-1346 (1999).

Guo et al., "Changes in substrate specificity of the recombinant form of phenol sulfotransferase IV (tyrosine-ester sulfotransferase)," Chem.-Biol. Interact., vol. 92, pp. 25-31 (1994).

Habuchi et al., The Occurrence of Three Isoforms of Heparan Sulfate 6-O-Sulfotransferase Having Different Specificities for Hexuronic Acid Adjacent to the Targeted N-Sulfoglucosamine, J. Biol. Chem., vol. 275, No. 4, pp. 2859-2868 (Jan. 28, 2000).

Habuchi et al., "Molecular Characterization and Expression of Heparan-sulfate 6-Sulfotransferase—Complete cDNA Cloning in Human and Partial Cloning in Chinese Hamster Ovary Cells," The Journal of Biological Chemistry, vol. 273, No. 15, pp. 9208-9213 (Apr. 10, 1998).

Habuchi et al., "Purification of Chondroitin 6-Sulfotransferase Secreted from Cultured Chick Embryo Chondrocytes," The Journal of Biological Chemistry, vol. 268(29), pp. 21968-21974 (1993).

HajMohammadi, S.; Enjyoji, K.; Princivalle, M.; Christi, P.; Lech, M.; Beeler, D. L.; Rayburn, H.; Schwartz, J. J.; Barzegar, S.; de Agostini, A. I.; Post, M. J.; Rosenberg, R. D.; Shworak, N. W. J. Clin. Invest. 2003, 111, 989.

Hansen, S. U.; Miller, G. J.; Cole, C.; Rushton, G.; Avizienyte, E.; Jayson, G. C.; Gardiner, J. M. Nat Commun 2013, 4:2016, doi:10.1038/ncomms3016.

Harada et al., "Dalteparin, a low molecular weight heparin, attenuates inflammatory responses and reduces ischemia-reperfusion-induced liver injury in rats." Crit. Care Med., vol. 34, Article No. 8, (2006).

Harris et al., Endocytic Function, Glycosaminoglycan Specificity, and Antibody Sensitivity of the Recombinant Human 190-kDa Hyaluronan Receptor for Endocytosis (HARE), J. Biol. Chem., vol. 279, No. 35, p. 36201-36209 (Aug. 27, 2004).

Heard, "Acetylcystein for acetaminophen poisoning." N. Eng. J. Med. vol. 359, pp. 285-292 (2008).

Hernaiz et al., "Enzymatic Modification of Heparan Sulfate on a Biochip Promotes Its Interaction with Antithrombin III," Biochem. Biophys. Res. Commun., vol. 276, pp. 292-297 (2000).

Hirsch et al., Heparin and Low-Molecular-Weight Heparin The Seventh ACCP Conference on Antithrombotic and Thrombolytic Therapy, CHEST, vol. 126, pp. 188S-203S (2004).

Hirsh et al., "Beyond Unfractionated Heparin and Warfarin Current and Future Advances," Circulation, vol. 116, pp. 552-560 (2007).

Holmborn et al., "Heparan Sulfate Synthesized by Mouse Embryonic Stem Cells Deficient in NDST1 and NDST2 Is 6-O-Sulfated but Contains No. N-Sulfate Groups," J. Biol. Chem., vol. 279, No. 41, pp. 42355-42358 (2004).

Hsieh et al., "Chemoenzymatic synthesis and structural characterization of 2-O-sulfated glucuronic acid containing heparan sulfate hexasaccharides." Glycobiology vol. 24, pp. 681-692 (2014).

Hsieh, P.-H.; Thieker, D. F.; Guerrini, M.; Woods, R. J.; Liu, J. Sci Rep 2016, 6, 29602; doi: 10.1038/srep29602.

Hu, Y.-P.; Lin, S.-Y.; Huang, C.-Y.; Zulueta, M. M. L.; Liu, J.-Y.; Chang, W.; Hung, S.-C. Nat Chem 2011, 3, 557.

Huang, C. C.; Meng, E. C.; Morris, J. H.; Pettersen, E. F.; Ferrin, T. E. Nucleic Acids Res. 2014, 42, w478.

Huebener el al., "The HMGB1/RAGE axis triggers neutrophil-mediated injury amplification following necrosis." J. Clin. Invest. vol. 125, pp. 539-550 (2015).

Humphrey, W.; Dalke, A; Schulten, K. J. Mol. Graph. 1996, 14, 33.

Iba et al., "Advance in the management of sepsis-induced coagulopathy and disseminated intravascular coagulation." J. Clin. Med., vol. 8, Article No. 728 (16 pages) (2019).

Ibrahimi et al., "Kinetic Model for FGF, FGFR, and Proteoglycan Signal Transduction Complex Assembly," Biochemistr, vol. 43, pp. 4724-4730 (2004).

Intention to Grant corresponding to European Patent Application No. 11849994.6 dated Apr. 7, 2021.

Intention to Grant corresponding to European Patent Application No. 11849994.6 dated Sep. 1, 2021.

Intention to Grant corresponding to European Patent Application No. 14812890.3 dated Oct. 27, 2021.

International Preliminary Report on Patentability corresponding to International Application No. PCT/US 2018/040774 dated Jan. 16, 2020.

International Preliminary Report on Patentability corresponding to International Application No. PCT/US2019/037993 dated Dec. 22, 2020.

International Preliminary Report on Patentability Corresponding to International Patent Application No. PCT/US 2020/060581 dated May 27, 2022.

International Preliminary Report on Patentability corresponding to International Application No. PCT/US2014/042683 dated Dec. 30, 2015.

International Preliminary Report on Patentability corresponding to International Application No. PCT/US2011/066843 dated Jul. 4, 2013.

International Preliminary Report on Patentability Corresponding to International application No. PCT/US 2018/021986 dated Sep. 10, 2019.

International Preliminary Report on Patentability corresponding to International application No. PCT/US 2018/059152 dated May 14, 2020.

International Search Report and the Written Opinion of the International Searching Authority Corresponding to International Application No. PCT/US 2018/040774 dated Sep. 18, 2018.

International Search Report and the Written Opinion of the International Searching Authority corresponding to International application No. PCT/US 2018/059152 dated Mar. 6, 2019.

International Search Report and Written Opinion of the International Searching Authority Corresponding to International Patent Application No. PCT/US 2020/060581 dated Feb. 11, 2021.

International Search Report corresponding to International Application No. PCT/US2019/037993 dated Oct. 18, 2019.

International Search Report corresponding to International Application No. PCT/US2014/042683 dated Oct. 9, 2014.

International Search Report Corresponding to International application No. PCT/US 2018/021986 dated Aug. 1, 2018.

Jackson et al., "Thromboinflammation: challenges of therapeutically targeting coagulation and other host defense mechanisms." Blood, vol. 133, pp. 906-918 (2019).

Jaeschke et al., "Complement activates Kupffer cells and neutrophils during reperfusion after hepatic ischemia." Am. J. Physiol-Gastroint. Liver Physiol., vol. 264, pp. G801-G809 (1993).

Jaimes et al., "Unfractioned heparin for treatment of sepsis: A randomized clinical trial (The HETRASE Study)." Crit. Care Med., vol. 37, pp. 1185-1196 (2009).

Jemth et al., "Oligosaccharide library-based assessment of heparan sulfate 6-0-sulfotransferase substrate specificity," Journal of Biological Chemistry, vol. 278, No. 27, pp. 24371-24376 (Jul. 4, 2003).

Jin, L.; Abrahams, P.; Skinner, R.; Petitou, M.; Pike, R. N.; Carrell, R. W. Proc. Natl. Acad. Sci. 1997, 94, 14683.

Kakkar et al., "Low Molecular Weight Heparin, Therapy With Dalteparin, and Survival in Advanced Cancer: The Fragmin Advanced Malignancy Outcome Study (Famous)," J. Clin. Oncol., vol. 22, No. 10, pp. 1944-1948 (May 15, 2004).

Kakuta et al., "Heparan sulphate N-sulphotransferase activity: reaction mechanism and substrate recognition," Biochem. Soc. Trans., vol. 31 (pt2), pp. 331-334 (2003).

(56) References Cited

OTHER PUBLICATIONS

Kamimura, K.; Rhodes, J. M.; Ueda, R.; McNeely, M.; Shukla, D.; Kimata, K.; Spear, P. G.; Shworak, N. W.; Nakata, H. J. Cell Biol. 2004, 166, 1069.

Kaneko et al., "Coagulation and fibrinolytic profiles and appropriate use of heparin after living-donor liver transplantation." Clin. Transplant., vol. 19, pp. 804-809 (2005).

Kirschner, K. N.; Yongye, A B.; Tschampel, S. M.; Gonzalez-Outeirino, J.; Daniels, C. R.; Foley, B. L.; Woods, R. J. J. Comput. Chem. 2008, 29, 622.

Kisselev, L., "Polypeptide release factors in prokaryotes and eukaryotes: same function, different structure," Structure, vol. 10, pp. 8-9 (2002).

Kollman, P. A; Massova, I.; Reyes, C.; Kuhn, B.; Hua, S.; Chong, L.; Lee, M.; Lee, T.; Duan, Y.; Wang, W.; Donini, O.; Cieplak, P.; Srinivasan, J.; Case, D. A; Cheatham, T. E. r. Acc. Chem. Res. 2000, 33, 889.

Konishi et al., "Hepatic ischemia/reperfusion: mechanisms of tissue injury, repair, and regeneration." Gene Expr., vol. 17, pp. 277-287 (2017).

Kopec et al., "Fibrin(ogen) drives repair after acetaminophen-induced liver injury via leukocyte aMb2 integrin-dependent upregulation of Mmp12." J. Hepatol. vol. 66, pp. 787-797 (2017).

Kreimann, M.; Brandt, S.; Krauel, K.; Block, S.; Helm, C.; Weitschies, W.; Greinacher, A.; Delcea, M. Blood 2014, in press.

Kreuger et al., Interactions between heparan sulfate and proteins: the concept of specificity, J. Cell Biol., vol. 174, No. 3, pp. 323-327 (Jul. 31, 2006).

Krummenacher et al., "The First Immunoglobulin-Like Domain of HveC Is Sufficient To Bind Herpes Simplex Virus gD with Full Affinity, While the Third Domain Is Involved in Oligomerization of HveC," J. Virol., vol. 73, pp. 8127-8137 (Oct. 1999).

Kuberan et al., "Enzymatic synthesis of antithrombin III-binding heparan sulfate pentasaccharide," Nature Biotechnology, vol. 21, No. 11, 1343-1346 (Nov. 2003).

Kuberan et al., "Rapid Two-Step Synthesis of Mitrin from Heparosan: A Replacement for Heparin," J. Am. Chem. Soc., vol. 125, p. 12424-12425 (2003).

Kuberan et al., The Journal of Biological Chemistry, "Chemoenzymatic Synthesis of Classic and Non-classical Anticoagulant Heparan Sulfate Polysaccharides", 2003, vol. 278, No. 52, pp. 52613-52621 (Year: 2003).

Kubes et al., "Sterile inflammation in the liver." Gastroenterology, vol. 143, pp. 1158-1172 (2012).

Kyte & Doolittle (1982) A Simple Method for Displaying the Hydropathic Character of a Protein. J. Mol Biol, 157: 105-132.

Langdown, J.; Belzar, K. J.; Savory, W. J.; Baglin, T. P.; Huntington, J. A. J. Mo/. Biol. 2009, 386, 1278.

Laremore, T. et al "Ionic liquid matrix for direct UV-MALDI-TOF-MS Analysis of Dermatan Sulfate and Chondroitin Sulfate Oligosaccharides." Anal. Chem., vol. 79, pp. 1604-1610. (Year: 2007).

Laurent et al., "The Molecular-Weight-Dependence of the Anti-Coagulant Activity of Heparin," Biochem. J., vol. 175, pp. 691-701 (1978).

Ledin et al., "Heparan Sulfate Structure in Mice with Genetically Modified Heparan Sulfate Production," J. Biol. Chem., vol. 279, No. 41, pp. 42732-42741 (2004).

Lee, "Acetaminophen toxicity: changing perceptions on a social/medical issue." Hepatology, vol. 46, pp. 966-970 (2007).

Lee, M.K., and Lander, A.D., (1991) Proc. Natl. Acad. Sci. USA 88, 2768-2772.

Li et al., "Biosynthesis of Heparin/Heparan Sulfate cDNA Cloning and Expression of D-Glucuronyl C5-Epimerase From Bovine Lung," J. Biol. Chem., vol. 272, No. 4, pp. 28158-28163 (Oct. 31, 1997).

Li et al., "Enzymatic Synthesis of Homogeneous Chondroitin Sulfate Oligosaccharides." Angew. Chemie., vol. 129(39), pp. 11946-11949 (2017).

Li et al., "Enzymatic synthesis of homogenous chondroitin sulfate e oligosaccharides," Abstract of Glycobiol., vol. 28(12) (2018) [Abstract].

Li J, Su W, and Liu J. "Enzymatic synthesis of homogeneous chondroitin sulfate oligosaccharides." Angew Chem Int Ed. 2017;56:11784-7.

Liliensiek et al., "Receptor for advanced glycation end products (RAGE) regulates sepsis but not the adaptive immune response." J. Clin. Invest. vol. 113, pp. 1641-1650 (2004).

Lin et al., "Colorimetric Determination of the Purity of 39-Phospho Adenosine 59-Phosphosulfate and Natural Abundance of 39-Phospho Adenosine 59-Phosphate at Picomole Quantities," Anal. Biochem., vol. 264, pp. 111-117 (1998).

Lin et al., "Enzymatic Synthesis and Regeneration of 3'-Phosphoadenosine 5'Phosphosulfate (PAPS) for Regioselective Sulfation of Oligosaccharides," J. Am. Chem. So., vol. 117, pp. 8031-8032 (1995).

Lindahl et al., "Regulated Diversity of Heparan Sulfate," The Journal of Biological Chemistry, vol. 273, No. 39, pp. 24979-24982 (Sep. 25, 1998).

Lindahl et al., "Generation of "Neoheparin" from E. coli K5 Capsular Polysaccharide," J. Med. Chem., vol. 48, pp. 349-352 (2005).

Lindahl, U.; Backstrom, G.; Thunberg, L.; Leder, I. G. Proc. Natl. Acad. Sci. 1980, 77, 6551.

Linhardt et al., "Production and Chemical Processing of Low Molecular WQeight Heparins," Seminars in Thrombosis and Hemostasis, vol. 25, Suppl.3, pp. 5-16 (1999).

Linhardt, R. J., J. Med. Chem., vol. 46, pp. 2551-2564 (2003).

Liu et al., "Anticoagulant heparan sulfate: structural specificity and biosynthesis," Appl Microbiol Biotechnol., vol. 74, pp. 263-272 (2007).

Liu et al., "Cell Surface Heparan Sulfate and Its Roles in Assisting Viral Infections," Medicinal Research Reviews, vol. 22, No. 1, pp. 1-25 (2002).

Liu et al., "Characterization of a Heparan Sulfate Octasaccharide that Binds to Herpes Simplex Virus Type 1 Glycoprotein D," The Journal of Biological Chemistry, vol. 277, No. 36, pp. 33456-33467 (Sep. 6, 2002).

Liu et al., "Expression of Heparan Sulfate D-Glucosaminyl 3-O-Sulfotransferase Isoforms Reveals Novel Substrate Specificities," The Journal of Biological Chemistry, vol. 274, No. 8, pp. 5185-5192 (Feb. 19, 1999).

Liu et al., "Heparan Sulfate D-Glucosaminyl 3-O-Sulfotransferase-3A Sulfates N-Unsubstituted Glucosamine Residues," The Journal of Biological Chemistry vol. 274, No. 53, pp. 38155-38162 (Dec. 31, 1999).

Liu et al., "Purification of Heparan Sulfate D-Glucosaminyl 3-O-Sulfotransferase," The Journal of Biological Chemistry, vol. 271, No. 43, pp. 27072-27082 (Oct. 25, 1996).

Liu et al., Chemoenzymatic Design of Heparan Sulfate Oligosaccharides, J Biol Chem, vol. 285, No. 44, pp. 34240-34249 (Oct. 29, 2010).

Liu et al., "Enzymatic Placement of 6-O-Sulfo Groups in Heparan Sulfate," Biochemistry 2011, 50, 4382-4391.

Liu et al., "Lessons learned from the contamination of heparin," Nat. Prod. Rep., vol. 26, pp. 313-321 (2009).

Liu, J. et al., Royal Society of Chemistry, "Chemoenzymatic synthesis of heparan sulfate and heparin", vol. 31, pp. 1676-1685 (Year: 2014).

Loganathan et al., "Structural Variation in the Antithrombin III Binding Site Region and Its Occurrence in Heparin from Different Sources," Biochemistry, vol. 29, pp. 4362-4368 (1990).

Lopin et al., "From Polymer to Size-Defined Oligomers: An Expeditious Route for the Preparation of Chondroitin Oligosaccharides." Angew. Chem. Int. Ed., vol. 45, pp. 2574-2578 (2006).

Lopin-Bon et al., "Stereocontrolled preparation of biotinylated chondroitin sulfate E di-, tetra-, and hexasaccharide conjugates." Carbohydr. Res., vol. 402, pp. 35-43 (2015).

Lu et al., "Innate Immune Regulations and Liver Ischemia-Reperfusion Injury." Trasplantation, vol. 100, pp. 2601-2610 (2016).

Lundbäck et al., "A novel high mobility group box 1 neutralizing chimeric antibody attenuates drug-induced liver injury and postinjury inflammation in mice." Hepatology vol. 64, pp. 1699-1710 (2016).

Ly et al., "The proteoglycan bikunin has a defined sequence." Nat. Chem. Biol., vol. 7, pp. 827-833 (2011).

(56) References Cited

OTHER PUBLICATIONS

Maccarana et al., J. Biol. Chem., vol. 268, pp. 23898-23905 (1993).
Macchione et al., "Synthesis of chondroitin sulfate oligosaccharides using N-tetrachlorophthaloyl and N-trifluoroacetyl galactosamine building blocks," European Journal of Organic Chemistry, pp. 3868-3884 (2014).
Mackman, "Triggers, targets and treatments for thrombosis," Nature, vol. 451, No. 21, pp. 914-918 (Feb. 21, 2008).
Mahe, I.; Chidac, J.; Helfer, H.; Nobel, S. J. Thromb. Haemost. 2016, 14, 2107.
Man et al., "Tolerance of the liver to intermittent pringle maneuver in hepatectomy for liver tumors." JAMA Sirgery, vol. 134, pp. 533-539 (1999).
Marcus et al. Anal. Biochem., vol. 107, pp. 296-304 (1980).
Marshall et al., "A review of the effects of manipulation of the cysteine residues of rat aryl sulfotransferase IV," Chem. Biol. Interact., vol. 109, pp. 107-116 (1998).
Marshall et al., "Control of Activity through Oxidative Modification at the Conserved Residue Cys66 of Aryl Sulfotransferase IV," J. Biol. Chem., vol. 272, No. 14, pp. 9153-9160 (Apr. 14, 1997).
Martinez-Gonzalez et al., "New Challenges for a Second-Generation Low-Molecular-Weight Heparin: Focus on Bemiparin," Expert Rev. Cardiovasc. Ther., vol. 8, No. 5, pp. 625-634 (2010).
Maza et al., "Synthesis of chondroitin/dermatan sulfate-like oligosaccharides and evaluation of their protein affinity by fluorescence polarization." Org. Biomol. Chem., vol. 11, pp. 3510-3525 (2013).
Mazany et al., "Human chondroitin 6-sulfotransferase: cloning, gene structure, and chromosomal localization," Biochimica et Biophysica Acta, vol. 1407, pp. 92-97 (1998).
McGowan, K. E.; Makari, J.; Diamantouros, A.; Bucci, C.; Rempel, P.; Selby, R.; Geerts, W. Blood 2016, 127, 1954.
Miyachi et al., "Syntheses of chondroitin sulfate tetrasaccharide structures containing 4,6-disulfate patterns and analysis of their interaction with glycosaminoglycan-binding protein." Bioorg. Med. Chem. Lett., vol. 25, pp. 1552-1555 (2015).
Miyata et al., "Persistent cortical plasticity by upregulation of chondroitin 6-sulfation." Nat. Neurosci., vol. 15, pp. 414-422 (2012).
Mizumoto et al., "Molecular interactions between chondroitin-dermatan sulfate and growth factors/receptors/matrix proteins." Curr. Opin. Struct. Biol., vol. 34, pp. 35-42 (2015).
Monneau et al., "The sweet spot: how GAGs help chemokines guide migrating cells." J. Leukoc. Biol. Vol. 99, pp. 935-953 (2016).
Moon et al., "Dissecting the substrate recognition of 3-O-suflotransferase for the biosynthesis of anticoagulant heparin," Proceedings of the National Academy of Sciences, vol. 109, No. 14, pp. 5265-5270 ( 2012).
Moon et al., "Structural Analysis of the Sulfotransferase (3-O-Sulfotransferase Isoform 3) Involved in the Biosynthesis of an Entry Receptor for Herpes Simplex Virus 1," J. Biol. Chem., vol. 279, No. 43, pp. 45185-45193 (2004).
Mossanen et al., "Acetaminophen-induced acute liver injury in mice." Lab. Anim. vol. 49, pp. 30-36 (2015).
Mousa, "Drug Discovery and Evaluation: Pharmacological Assays" (ed. Vogel, H.), 393-456 (Springer-Verlag Berlin, Heidelberg, New York (2008).
Mousa, "Heparin and Low-Molecular Weight Heparins in Thrombosis and Beyond," Meth. Mol. Biol., vol. 663, pp. 109-132 (2010).
Mousa, "In Vitro Methods of Evaluating Antithrombotics and Thrombolytics," Meth. Mol. Biol., vol. 663, pp. 1-28 (2010).
Munoz et al., "Enzymatic synthesis of heparin related polysaccharides on sensor chips: Rapid screening of heparin-protein interactions," Biochemical and Biophysical Research Communications, Academic Press Inc., Orlando, FL, US, vol. 339, No. 2, pp. 597-602 (Jan. 13, 2006).
Nadanaka et al., "Characteristic Hexasaccharide Sequences in Octasaccharides Derived from Shark Cartilage Chondroitin Sulfate D with a Neurite Outgrowth Promoting Activity," The Journal of Biological Chemistry, vol. 273(6), pp. 3296-3307 (1998).
Nagano et al., "Chondroitin sulfate protects vascular endothelial cells from toxicities of extracellular histones." Eur. J. Pharmacol., vol. 826, pp. 48-55 (2018).
Nam et al., "Syndecan-1 Limits the Progression of Liver Injury and Promotes Liver Repair in Acetaminophen-Induced Liver Injury in Mice." Hepatology, vol. 66(5), pp. 1601-1615, doi: 10.1002/hep.29265 (2017).
Nastuk et al., "Expression Cloning and Characterization of NSIST, a Novel Sulfotransferase Expressed by a Subset of Neurons and Postsynaptic Targets," The Journal of Neuroscience, vol. 18, No. 18, pp. 7167-7177 (Sep. 15, 1998).
Needleman et al., "A General Method Applicable to the Search for Similarities in the Amino Acid Sequence of Two Proteins," J. Mol. Biol., vol. 48, pp. 443-453 (1970).
Nicola et al., Structure-Function Analysis of Soluble Forms of Herpes Simplex Virus Glycoprotein D., J. Virol., vol. 70, No. 6, pp. 3815-3822 (1996).
Noti et al., "Chemical Approaches to Define the Review Structure-Activity Relationship of Heparin-like Glycosaminoglycans," Chemistry & Biology, vol. 12, pp. 731-756 (Jul. 2005).
Notice of Allowance and Interview Summary corresponding to U.S. Appl. No. 14/898,865 dated Dec. 15, 2017.
Notice of Allowance and Interview Summary corresponding to U.S. Appl. No. 17/254,145 dated Jan. 30, 2023.
Notice of Allowance corresponding to U.S. Appl. No. 17/254,145 dated Dec. 8, 2022.
Notice of Allowance corresponding to U.S. Appl. No. 16/492,858 dated Sep. 12, 2022.
Notice of Allowance corresponding to U.S. Appl. No. 16/492,858 dated Feb. 10, 2023.
Notice of Allowance corresponding to U.S. Appl. No. 13/996,930 dated Aug. 11, 2021.
Notice of Issuance corresponding to Chinese Patent Application No. 201480044429.9 dated May 7, 2021.
Notice of Publication Corresponding to European Patent Application. No. 19822610.2 dated Mar. 31, 2021.
Notice of Publication Corresponding to European Patent application No. 18764628.6 dated Nov. 20, 2019.
Notice of Publication Corresponding to European Patent Application No. 18873131.9 dated Jul. 15, 2020.
Notice of Publication of Application Corresponding to U.S. Appl. No. 16/625,342 dated Oct. 29, 2021.
Notice of Publication of Application Corresponding to U.S. Appl. No. 17/254,145 dated Aug. 27, 2021.
Notification Concerning of Transmittal of International Preliminary Report on Patentability for International Application No. PCT/US2006/018778 (dated Nov. 24, 2007).
Notification of Transmittal of the International Search Report and the Written Opinion of the International Searching Authority, or the Declaration for International Application No. PCT/US06/18778 (dated Feb. 21, 2007).
Notification of Transmittal of the International Search Report and the Written Opinion of the International Searching Authority, or the Declaration corresponding to International Application No. PCT/US2008/008945 (dated Feb. 20, 2009).
Notification of Transmittal of the International Search Report and the Written Opinion of the International Searching Authority, or the Declaration corresponding to International Application No. PCT/US2011/066843 dated Aug. 22, 2012.
Oduah et al., "Heparin: Past, present, and future." Pharmaceuticals (Basel), vol. 9, Article No. 38 (2016).
Office Action (Decision of Rejection) corresponding to Chinese Patent Application No. 20180020095.X dated Dec. 1, 2022.
Office Action (Final) corresponding to U.S. Appl. No. 16/625,342 dated Nov. 4, 2022.
Office Action (Restriction Requirement) corresponding to U.S. Appl. No. 16/625,342 dated Dec. 16, 2021.
Office Action (Restriction Requirement) corresponding to U.S. Appl. No. 17/254,145 dated Nov. 26, 2021.
Office Action (Restriction Requirement) corresponding to U.S. Appl. No. 16/492,858 dated Jun. 30, 2021.
Office Action corresponding to Chinese Patent Application No. 201880020095.X dated Jun. 8, 2022.

(56) References Cited

OTHER PUBLICATIONS

Office Action corresponding to Chinese Patent Application No. 201480044429.9 dated Aug. 30, 2018.
Office Action corresponding to Chinese Patent Application No. 201480044429.9 dated Apr. 9, 2019.
Office Action corresponding to Chinese Patent Application No. 201480044429.9 dated Mar. 3, 2020.
Office Action corresponding to Chinese Patent Application No. 201880020095.X dated Sep. 22, 2021.
Office Action corresponding to Chinese Patent Application No. 2018800850125 dated Jan. 20, 2023.
Office Action corresponding to Chinese Patent Application No. 201880020095.X dated Apr. 18, 2023.
Office Action corresponding to Chinese patent Application No. 202310342719.2 dated May 8, 2023.
Office Action corresponding to European Patent Application No. 11849994.6 dated May 24, 2018.
Office Action corresponding to European Patent Application No. 11849994.6 dated Jan. 22, 2020.
Office Action corresponding to European Patent Application No. 14812890.3 dated Jun. 23, 2020.
Office Action corresponding to Japanese Patent Application No. 2019-549419 dated Dec. 23, 2022.
Office Action corresponding to Japanese Patent Application No. 2016-521505 dated Jul. 19, 2018.
Office Action corresponding to Japanese Patent Application No. 2016-521505 dated Jun. 21, 2019.
Office Action corresponding to Japanese Patent Application No. 2019-549419 dated Mar. 22, 2022.
Office Action corresponding to U.S. Appl. No. 12/178,434 dated Oct. 28, 2011.
Office Action corresponding to U.S. Appl. No. 12/178,434 dated Apr. 19, 2011.
Office Action corresponding to U.S. Appl. No. 12/178,434 dated Jan. 26, 2011.
Office Action corresponding to U.S. Appl. No. 16/492,858 dated Jan. 13, 2022.
Office Action corresponding to U.S. Appl. No. 16/625,342 dated Mar. 21, 2022.
Office Action corresponding to U.S. Appl. No. 17/254,145 dated Feb. 16, 2022.
Office Action corresponding to U.S. Appl. No. 13/996,930 dated Oct. 8, 2015.
Office Action corresponding to U.S. Appl. No. 13/996,930 dated May 26, 2016.
Office Action corresponding to U.S. Appl. No. 13/996,930 dated Dec. 21, 2017.
Office Action corresponding to U.S. Appl. No. 13/996,930 dated Jul. 30, 2018.
Office Action corresponding to U.S. Appl. No. 13/996,930 dated Nov. 22, 2019.
Office Action corresponding to Japanese Patent Application No. 2020-544568 dated Jan. 10, 2023.
Official Action corresponding to U.S. Appl. No. 11/920,319 dated Apr. 28, 2010.
Official Action corresponding to U.S. Appl. No. 14/898,865 dated Mar. 23, 2017.
Oliveira et al., "Neutrophils: a cornerstone of liver ischemia and reperfusion injury." Lab. Invest., vol. 98, pp. 51-62 (2018).
Ong et al., "Expression Cloning of a Human Sulfotransferase that Directs the Synthesis of the HNK-1 Glycan on the Neural Cell Adhesion Molecule and Glycolipids," The Journal of Biological Chemistry, vol. 273, No. 9, pp. 5190-5195 (Feb. 27, 1998).
Onufriev, A; Bashford, D .; Case, D. A Proteins 2004, 55, 383.
Ornitz et al., "Receptor Specificity of the Fibroblast Growth Factor Family," J. Biol. Chem., vol. 271, No. 25, pp. 15292-15297 (1996).
Ouyang et al., "Molecular Cloning and Expression of Human and Mouse Tyrosylprotein Sulfotransferase-2 and a Tyrosylprotein Sulfotransferase Homologue in Caenorhabditis elegans," The Journal of Biological Chemistry, vol. 273, No. 38, pp. 24770-24774 (Sep. 18, 1998).
Ozawa et al., "Nucleotide sequence of a full-length cDNA (PST-1) for aryl sulfotransferase from rat liver," Nucleic Acids Res., vol. 18, No. 13, p. 4001 (1990).
Park et al., "Cell surface heparan sulfate proteoglycans: selective regulators of ligand-receptor encounters." J. Biol. Chem. vol. 275, pp. 29923-29926 (2000).
Patel, V. N .; Lombaert, I. M.A.; Cowherd, S. N.; Shworak, N.; Xu, Y.; Liu, J.; Hoffman, M. P. Developmental Cell 2014, 29, 662.
Pempe, et al., "Probing Structural Selectivity of Synthetic Heparin Binding to Stabilin Protein Receptors," Journal of Biol. Chem., vol. 287, No. 25, pp. 20774-20783 (Jun. 15, 2012).
Petitou et al., "A Synthetic Antithrombin III Binding Pentasaccharide Is Now a Drug! What Comes Next?" Angew. Chem. Int. Ed., vol. 43, pp. 3118-3133 (2004).
Petitou et al., "Synthesis of thrombin-inhibiting heparin mimetics without side effects." Nature, vol. 398, pp. 417-422 (Apr. 1, 1999).
Pettersen, E. F.; Goddard, T. D.; Huang, C. C.; Couch, G. S.; Greenblatt, D. M.; Meng, E. C.; Ferrin, T. E. J. Comp. Chem. 2004, 25, 1605.
Pierce et al., "Inflammatory response to trauma: implications for coagulation and resuscitation." Curr. Opin. Anesthesio., vol. 27, pp. 246-252 (2014).
Pinhal et al., "Enzyme interactions in heparan sulfate biosynthesis: Uronosyl 5-epimerase and 2-O-sulfotransferase interact in vivo.," Proc. Natl. Acad. Sci. U. S. A., vol. 98, No. 23, pp. 12984-12989 (Nov. 6, 2001).
Proudfoot et al., "Glycosaminoglycan binding and oligomerization are essential for the in vivo activity of certain chemokines." Proc. Natl. Acad. Sci. USA vol. 100, pp. 1885-1890 (2003).
Pulsipher et al., "Directing Neuronal Signaling through Cell-Surface Glycan Engineering." J. Am. Chem. Soc., vol. 136, pp. 6794-6797 (2014).
Pye et al., "Heparan Sulfate Oligosaccharides Require 6-O-Sulfation for Promotion of Basic Fibroblast Growth Factor Mitogenic Activity," J. Biol. Chem., vol. 273, No. 36, pp. 22936-22942 (Sep. 4, 1998).
Raman, R.; Venkataraman, G.; Ernst, S.; Sasisekharan, R. Proc. Natl. Acad. Sci. 2003, 100, 2357.
Razi et al., "Structural and functional properties of heparin analogues obtained by chemical sulphation of *Escherichia coli* K5 capsular polysaccharide," Biochem. J., vol. 389, pp. 465-472 (1995).
Reizes et al., "Transgenic Expression of Syndecan-1 Uncovers a Physiological Control of Feeding Behavior by Syndecan-3," Cell, vol. 106, pp. 105-116 (Jul. 13, 2001).
Rohrmann et al., "Two N-acetylgalactosaminyltransferase are involved in the biosynthesis of chondroitin sulfate," European Journal of Biochemistry, vol. 148, pp. 463-469 (1985).
Roman-Blas et al., "The combined therapy with chondroitin sulfate plus glucosamine sulfate or chondroitin sulfate plus glucosamine hydrochloride does not improve joint damage in an experimental model of knee osteoarthritis in rabbits." Eur. J. Pharmacol., vol. 794, pp. 8-14 (2017).
Rosenberg et al., "Heparan Sulfate Proteoglycans of the Cardiovascular System Specific Structures Emerge But How Is Synthesis Regulated?" J. Clin. Invest., vol. 99, No. 9, pp. 2062-2070 (May 1997).
Saeki et al., "Molecular Cloning, Expression, and Characterization of a Novel Mouse Liver SULTIBI Sulfotransferase," J. Biochem., vol. 124, pp. 55-64 (1998).
Sala et al., "UDP-N-trifluoroacetylglucosamine as an alternative substrate in N-acetylglucosaminyltransferase reactions", Carbohydrate Research, vol. 306, pp. 127-136 (1998).
Saribas et al., "Production of N-sulfated 1-38 polysaccharides using yeast-expressed N- deacetylase/N-sulfotransferase-1 (NDST-I)," Glycobiology, vol. 14, pp. 1217-1228 (2004).
Sarris et al., "Inflammatory chemokines direct and restrict leukocyte migration within live tissues as glycan-bound gradients." Curr. Biol. vol. 22, pp. 2375-2382 (2012).
Sasisekharan et al., "Roles of Heparan-Sulphate Glycosaminoglycans in Cancer," Nat. Rev. Cancer, vol. 2, pp. 521-528 (Jul. 2002).

(56) References Cited

OTHER PUBLICATIONS

Sattelle, B. M.; Almond, A. Glycobiology 2011, 21, 1651.

Sattelle, B. M.; Hansen, S. U.; Gardiner, J. M.; Almond, A. J Am Chem Soc 2010, 132, 13132.

Schroeder et al., "Protamine neutralization of low molecular weight heparins and their oligosaccharide components," Anal Bioanal Chem, vol. 399, pp. 763-771 (2011).

Schwartz et al., "Virogenic BrdU and BrdU-sensitive DNA sequences are disproportionately concentrated in the template-active chromatin of rat embryo cells," Nuc Acids Res., vol. 6, No. 2, pp. 745-755 (Feb. 1979).

Schworer, R.; Zubkova, O. V.; Turnbull, J. E.; Tyler, P. C. Chem. Eur. J. 2013, 19, 6817.

Sheng et al., "Influenced of Phenylalanines 77 and 138 on the Stereospecifity of Aryl Sulfotransferase IV," Drug Metabol. Dispos., vol. 32, No. 5, pp. 559-565 (2004).

Sheng et al., "The Dominating Role of N-Deacetylase/N-Sulfotransferase 1 in Forming Domain Structures in Heparan Sulfate," The Journal of Biological Chemistry, vol. 286, No. 22, pp. 19768-19776 (Jun. 3, 2011).

Shiori et al., "Sequence determination of synthesized chondroitin sulfate dodecasaccharides." Glycobiology, vol. 26, pp. 592-606 (2016).

Shively et al., "Formation of Anhydrosugars in the Chemical Depolymerization of Heparin," Biochemistry, vol. 15, No. 18, pp. 3932-3942 (1976).

Shriver et al., "Glycomics: A Pathway to a Class of New and Improved Therapeutics," Nat. Rev. Drug Discov., vol. 3, pp. 863-873 (Oct. 2004).

Shukla et al., "A Novel Role for 3-O-Sulfated Heparan Sulfate in Herpes Simplex Virus 1 Entry," Cell, vol. 99, pp. 13-22 (Oct. 1, 1999).

Shukla et al., "Herpes viruses and heparan sulfate: an intimate relationship in aid of viral entry," The Journal of Clinical Investigation, vol. 108, No. 4, pp. 503-510 (Aug. 2001).

Shworak et al., "Molecular Cloning and Expression of Mouse and Human cDNAs Encoding Heparan Sulfate D-Glucosaminyl 3-O-Sulfotransferase," The Journal of Biological Chemistry, vol. 272, No. 44), pp. 28008-28019 (1997).

Singh, A; Tessier, M. B.; Pederson, K.; Wang, X.; Venot, A P.; Boons, G.- J.; Prestegard, J. H.; Woods, R. J. Can. J. Chem. 2016, 10.1139/cjc.

Sismey-Ragatz, et al., "Chemoenzymatic Synthesis with Distinc Pasteurella Heparosan Synthases," J. Biol. Chem., vol. 282, No. 39, pp. 28321-28327 (Jul. 11, 2007).

Smeds et al., "Substrate specificities of mouse heparan sulphate glucosaminyl 6-O-sulphotransferases," Biochem. J, vol. 372, pp. 371-380 (2003).

Smith et al., "Comparison of Biosequences," Adv. Appl. Math, vol. 2, pp. 482-489 (1981).

Solera et al., "Chondroitin sulfate tetrasaccharides: synthesis, three-dimensional structure and interaction with midkine." Chemistry, vol. 22, pp. 2356-2369 (2016).

Stabler et al., "Chondroitin sulphate inhibits NF-κB activity induced by interaction of pathogenic and damage associated molecules." Osteoarthritis and Cartilage, vol. 25, pp. 166-174 (2017).

STN record for Chen et al., dissertation, "Towards de novo synthesis of structure-defined oligosaccharides with heparan sulfate u biosynthetic enzymes", entered into STN: Apr. 20, 2009. 1 page.

Sugigura et al., "Molecular dissection of placental malaria protein VAR2CSA interaction with a chemo-enzymatically synthesized chondroitin sulfate library." Glycoconj. J., vol. 33, pp. 985-994 (2016).

Sugigura et al., "Sequential synthesis of chondroitin oligosaccharides by immobilized chondroitin polymerase mutants." Glycoconj. J., vol. 25, pp. 521-530 (2008).

Sugiura et al., "Baculovirus Envelope Protein ODV-E66 Is a Novel Chondroitinase with Distinct Substrate Specificity." J. Biol. Chem., vol. 286, pp. 29026-29034 (2011).

Sugiura et al., "Construction of a Chondroitin Sulfate Library with Defined Structures and Analysis of Molecular Interactions." J. Biol. Chem., vol. 287, pp. 43390-43400 (2012).

Sugumaran et al., "Simultaneous Sulfation of endogenous Chondroitin Sulfate and Chondroitin-derived Oligosaccharides" The Journal of Biological Chemistry vol. 261 No. 27 pp. 12659-12664 (Year: 1986).

Sundaram, M. et al., "Rational design of low-molecular weight heparins with improved in vivo activity," Proc. Natl. Acad. Sci., vol. 100, No. 2, pp. 651-656 (Jan. 21, 2003).

Supplemental Notice of Allowability and Interview Summary corresponding to U.S. Appl. No. 14/898,865 dated Jan. 12, 2018.

Szajek et al., "The US regulatory and pharmacopeia responses to the global heparin contamination crisis." Nat. Biotechnol. vol. 34, pp. 625-630 (2016).

Takagaki et al., "Enzymatic Reconstruction of a Hybrid Glycosaminoglycan Containing 6-Sulfated, 4-Sulfated, and Unsulfated N-Acetylgalactosamine" Biochemical and Biophysical Research Communications vol. 258 pp. 741-744 (Year: 1999).

Tamura et al., "Synthesis of chondroitin sulfate E octasaccharide in a repeating region involving an acetamide auxiliary." Carbohydr. Res., vol. 343, pp. 39-47 (2008).

Tecle, E.; Diaz-Balzac, C. A.; Bulow, H. E. G3 (Bethesda) 2013, 3, 541.

Teng et al., "Molecular functions of syndecan-1 in disease." Matrix Biol., vol. 31, pp. 3-16 (2012).

Thacker, B. E.; Seamen, E.; Lawrence, R.; Parker, M. W.; Xu, Y.; Liu, J.; Vander, K. C. W.; Eska, J. D. ACS Chem. Biol. 2016, 11, 971.

Thompson et al., "CLUSTAL W: improving the sensitivity of progressive multiple sequence alignment through sequence weighting, position-specific gap penalties and weight matrix choice," Nucleic Acids Res., vol. 22, No. 22, pp. 4673-4680 (1994).

Tohu et al., Anti-Xa and Anti-lla Drugs Alter International Normalized Ratio Measurements: Potential Problems in the Monitoring of Oral Anticoagulants Clin. Appl. Thrombos Hemostas, vol. 10, pp. 301-309 (2004).

Tsau, C.; Ito, M.; Gromova, A.; Hoffman, M. P.; Meech, R.; Makarenkova, H. P. Development 2011, 138, 3307.

Tsung et al., "HMGB1 release induced by liver ischemia involves Toll-like receptor 4-dependent reactive oxygen species production and calcium-mediated signaling." J. Exp. Med., vol. 204, pp. 2913-2923 (2007).

Tsung et al., "The nuclear factor HMGB1 mediates hepatic injury after murine liver ischemia-reperfusion." J. Exp. Med., vol. 201, pp. 1135-1143 (2005).

Uchimura et al., "Molecular Cloning and Characterization of an N-Acetylglucosamine-6-O-sulfotransferase," The Journal of Biological Chemistry, vol. 273, No. 35, pp. 22577-22583 (Aug. 28, 1998).

Vann et al., "The Structure of the Capsular Polysaccharide (K5 Antigen) of Urinary-Tract-Infective *Escherichia coli* 010 : K5 : H4 A Polymer Similar to Desulfo-Heparin," Eur. J. Biochem, vol. 116, pp. 359-364 (1981).

Venereau et al., "HMGB1 as biomarker and drug target." Pharmacol. Res. vol. 111, pp. 534-544 (2016).

Wang et al., "*E. coli* K5 fermentation and the Preparation of Heparosan, a Bioengineered Heparin Precursor," Biotechnol. Bioeng, vol. 107, No. 7, pp. 968-977 (Dec. 15, 2010).

Wang et al., "Edothelial heparan sulfate deficiency impairs L-selectin- and chemokine-mediated neutrophil trafficking during inflammatory responses." Nat. Immunol. vol. 6, pp. 902-910 (2005).

Weber et al., "Renal dysfunction in liver transplant recipients: Evaluation of the critical issues." Liver Transplant., vol. 18, pp. 1290-1301 (2012).

Weitz et al., "Beyond heparin and warfarin: the new generation of anticoagulants," Expert Opin. Investig. Drugs, vol. 16, No. 3, pp. 271-282 (2007).

Weitz, "Potential of new anticoagulants in patients with cancer," Thromb. Res., vol. 125 (Suppl 2), pp. S30-S35 (2010).

Wildhagen et al., "Nonanticoagulant heparin prevents histone-mediated cytotoxicity in vitro and improves survival in sepsis." Blood vol. 123, pp. 1098-1101 (2014).

(56) References Cited

OTHER PUBLICATIONS

Willis et al., "Examination of the Kinetics of Herpes Simplex Virus Glycoprotein D Binding to the Herpesvirus Entry Mediator, Using Surface Plasmon Resonance," J. Virol., vol. 72, pp. 5938-5947 (Jul. 1998).
Wishart et al., "A single mutation converts a novel phosphotyosine binding domain into a dual-specificity phosphatase," J. Biol. Chem., vol. 270, No. 45, pp. 26782-26785 (1995).
Witkowski et al., "Conversion of b-ketoacyl synthase to a Malonyl Decarboxylase by replacement of the active cysteine with glutamine," Biochemistry, vol. 38, pp. 11643-11650 (1999).
Written Opinion corresponding to International Application No. PCT/US2019/037993 dated Oct. 18, 2019.
Written Opinion of the International Searching Authority Corresponding to International Application No. PCT/US 2018/021986 dated Aug. 1, 2018.
WuDunn et al., "Initial interaction of herpes simplex virus with cells is binding to heparan sulfate," J. Virol., vol. 63, No. 1, pp. 52-58 (1989).
Xia et al., "Heparan Sulfate 3-O-Sulfotransferase Isoform 5 Generates Both an Antithrombin-binding Site and an Entry Receptor for Herpes Simplex Virus, Type 1," J. Biol. Chem., vol. 277, No. 40, Pp. 37912-37919 (2002).
Xu et al., "Characterization of heparan sulphate 3-O-sulphotransferase isoform 6 and its role in assisting the entry of herpes simplex virus type 1," Biochem. J., vol. 385, pp. 451-459 (2005).
Xu et al., Chemoenzymatic Synthesis of Homogeneous Ultralow Molecular Weight Heparins, Science, vol. 334, pp. 498-501 (Oct. 2011).
Xu et al., "Heparan sulfate is essential for high mobility group protein 1 (HMGB1) signaling by the receptor for advanced glycation end products (RAGE)." J. Biol. Chem. vol. 286, pp. 41736-41744 (2011).
Xu et al., "Homogeneous low-molecular-weight heparins with reversible anticoagulant activity." Nat. Chem. Biol. vol. 10, pp. 248-250 (2014).
Xu et al., Synthetic oligosaccharides can replace animal-sourced low-molecular weight heparins Sci. Transl. Med. vol. 9, eaan5954 (2017).
Xu J, Zhang X, Monestier M, Esmon NL, and Esmon CT. Extracellular histones are mediators of death through TLR2 and TLR4 in mouse fatal liver injury. J Immunol. 2011;187:2626-31.
Xu J, Zhang X, Pelayo R, Monestier M, Ammollo CT, Semeraro F, et al. Extracellular histones are major mediators of death in sepsis. Nat Med. 2009;15:1318-21.
Xu, D. et al., "Engineering sulfotransferases to modify heparan sulfate," Nat Chem Biol, vol. 4, No. 3, pp. 200-202 (Mar. 2008).
Xu, D.; Esko, "Demystifying Heparan Sulfate-Protein Interactions," J. Annu Rev Biochem. 2014, 83, 129.
Xu, D.; Olson, J.; Cole, J. N.; van Wijk, X. M.; Brinkmann, V.; Zychlinsky, A.; Nizet, V.; Eska, J. D.; Chang, Y. C. Infect. Immun. 2015, 83, 3648.
Xu, et al., "Homogeneous low-molecular-weight heparins with reversible anticoagulant activity," Nat Chem Biol., vol. 10, pp. 248-252 (2014).
Xue et al., "Impact of donor binding on polymerization catalyzed by KfoC by regulating the affinity of enzyme for acceptor." Biochim. Biophys. Acta, vol. 1860, pp. 844-855 (2016).
Yang et al. Effects of 3' -phosphoadenosine 5'-phosphate on the activity and folding of phenol sulfotransferase. Chem.-Biol. Interact. 109: 129-135 (1998).

Yang et al., "An Approach to Synthesize Chondroitin Sulfate-E (CS-E) Oligosaccharide Precursors." J. Organic Chem., vol. 83, pp. 5897-5908 (2018).
Yang et al., "Middle region of the Borrelia burgdorferi surface-located protein 1 (Lmp1) interacts with host chondroitin-6-sulfate and independently facilitates infection." Cell Microbiology, vol. 18, 97-110 (2016).
Yang et al., "Two Phenol Sulfotransferase Species from One cDNA: Nature of the Differences," Protein Expression Purif, vol. 8, pp. 423-429 (1996).
Yang, "Inflammation plays a dual role in acetaminophen hepatotoxicity," Translational Medicine Journal, vol. 5, No. 3, pp. 129-133 (Jun. 2016).
Yang, J.; Hsieh, P.; Liu, X.; Zhou, W.; Zhang, X.; Zhao, J.; Xu, Y.; Zhang, F.; Linhardt, R. J.; Liu, J. Chem Comm 2017, 53, 1743.
Yang, Z.; Lasker, K.; Schneidman-Duhovny, D.; Webb, B.; Huang, C. C.; Pettersen, E. F.; Goddard, T. D.; Meng, E. C.; Sali, A; Ferrin, T. E. J. Struct. Biol. 2012, 179, 269.
Yoshinari et al., "Molecular Cloning, Expression, and Enzymatic Characterization of Rabbit Hydroxysteroid Sulfotransferase AST-RB2 (ST2A8)," J. Biochem., vol. 123, pp. 740-746 (1998).
Yu et al., "Highly Efficient Chemoenzymatic Synthesis of Beta1-3-Linked Galactosides," Chemical Communications, vol. 46(40), pp. 7507-7509 (2010).
Yusa et al., "N-Linked Oligosaccharides on Chondroitin 6-Sulfotransferase-1 Are Required for Production of the Active Enzyme, Golgi Localization, and Sulfotransferase Activity toward Keratan Sulfate." J. Biol. Chem., vol. 281, pp. 20393-20403 (2006).
Zhang et al., "6-O-Sulfotransferase-1 Represents a Critical Enzyme in the Anticoagulant Heparan Sulfate Biosynthetic Pathway*," J. Biol. Chem., vol. 276, pp. 42311-42321 (2001).
Zhang et al., "Solution Structures of Chemoenzymatically Synthesized Heparin and Its Precursors," J. Am. Chem. Soc., vol. 130, pp. 12998-13007 (2008).
Zhang et al., "The Effect of Precursor Structures on the Action of Glucosaminyl 3-O-Sulfotransferase-1 and the Biosynthesis of Anticoagulant Heparan Sulfate," J. Biol. Chem., vol. 276, No. 31, pp. 28806-28813 (2001).
Zhao et al. "Enzymatic route to preparative-scale synthesis of UDP-GlcNAc/GalNAc, their analogues and GDP-fucose," Nat. Protoc., vol. 5, No. 4, pp. 636-646 (2010).
Zhou et al. "Expression of heparin sulfate sulfotransferases in Kluyveromyces lactis and preparation of 3'-phsphoadenosie-5'-phosphosulfate," Glycobiology, vol. 21, No. 6, pp. 771-780 (2011).
Zitvogel et al., "Decoding cell death signals in inflammation and immunity." Cell, vol. 140, pp. 798-804 (2010).
Zong, C.; Huang, R.; Condac, E.; Chiu, Y.; Xiao, W.; Li, Z. Q.; Lu, W.; Ishihara, M.; Wang, S.; Ramiah, A.; Stickney, M.; Azadi, P.; Amster, I. J.; Moremen, K. W.; Wang, L.; Sharp, J. S.; Boons, G.-J. J. Am. Chem. Soc. 2016, 138, 13059.
Office Action (Notice of Reasons for Rejection) corresponding to Japanese Patent Application No. 2020-570916 dated Jun. 20, 2023.
Office Action corresponding to Chinese Patent Application No. 2019800446973 dated Jul. 7, 2023. .
Office Action corresponding to Chinese Patent Application No. 202080092892 dated Jun. 21, 2023.
Office Action corresponding to European Patent Application No. 18873131.9-1112 dated Aug. 14, 2023.
Office Action corresponding to U.S. Appl. No. 16/625,342 dated Jun. 15, 2023.
Shiver et al., (2012) "Heparin and Heparan Sulfate: Analyzing Structure and Microheterogeneity," Handb Exp. Pharmacol. (207): pp. 159-176.
Office Action Corresponding to Japanese Patent Application serial No. 2020-544568 dated Sep. 26, 2023.

* cited by examiner

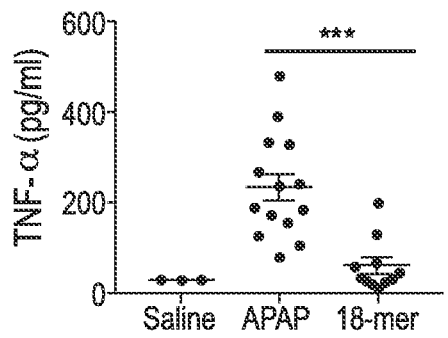
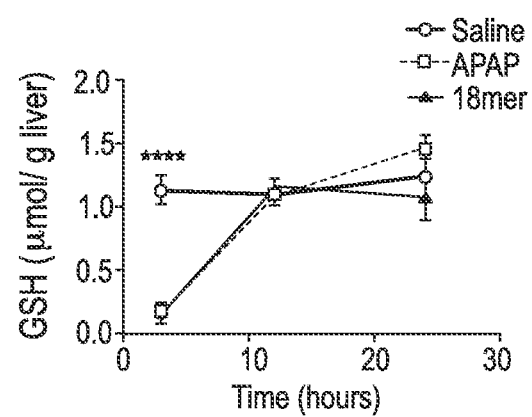
FIG. 6A
FIG. 6B
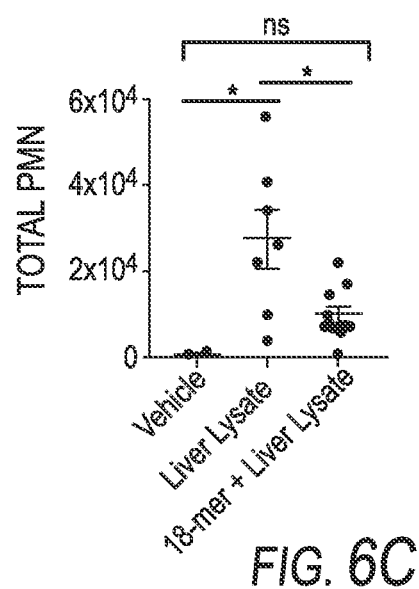
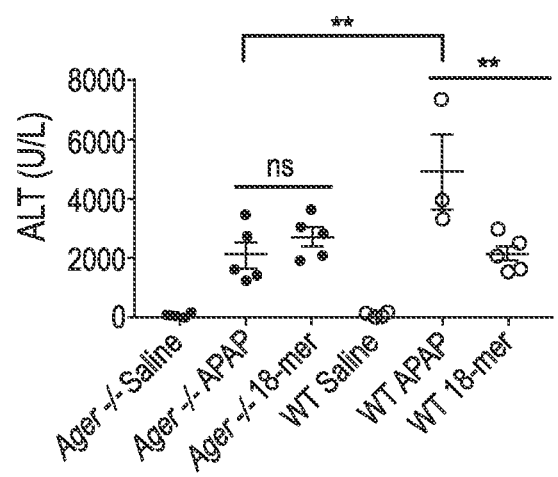
FIG. 6C
FIG. 6D

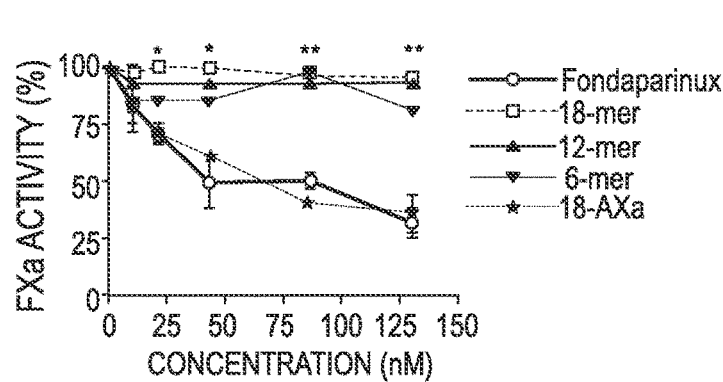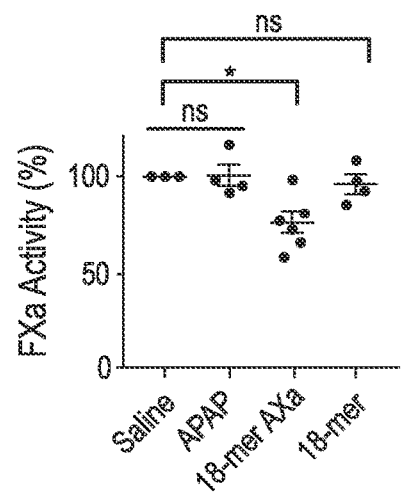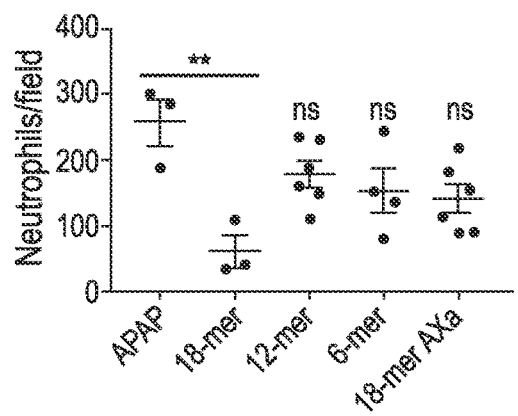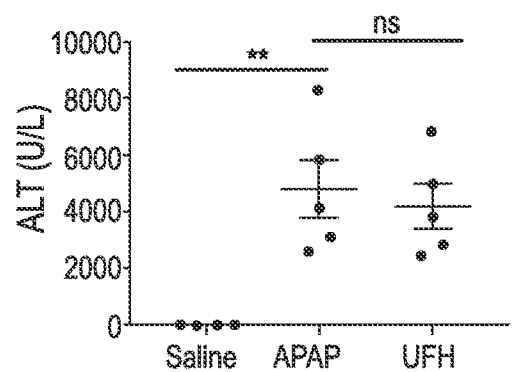
FIG. 8A
FIG. 8B
FIG. 8C
FIG. 8D

SULFATED OLIGOSACCHARIDES HAVING ANTI-INFLAMMATORY ACTIVITY

CROSS-REFERENCE TO RELATED APPLICATIONS

This application is a 35 U.S.C. Section 371 national phase application of PCT International Application Serial No. PCT/US2018/059152, filed Nov. 5, 2018, which claims benefit of U.S. Provisional Patent Application Ser. No. 62/581,443, filed Nov. 3, 2017, herein incorporated by reference in its entirety.

TECHNICAL FIELD

Disclosed herein in some embodiments are new sulfated heparan sulfate oligosaccharide compounds having anti-inflammatory activity. For example, in some embodiments it is observed that the compounds display a protective effect on drug-induced liver damage. While it is not desired to be bound by any particular theory of operation, the compounds likely inhibit the interaction of HMGB1/RAGE, a key signaling interaction involved in sterile inflammatory injury. This discovery can be applied for a wide range of diseases that are caused by over reaction of inflammation responses.

BACKGROUND

Sterile inflammation is a natural process that initiates tissue repair in response to cellular damage. However, exaggerated inflammation after an initial insult often damages surrounding healthy tissues and is a key contributor to many disease processes. High mobility group box 1 (HMGB1) is a DNA binding protein that regulates transcription and is released from the nucleus during necrotic cell death (Zitvogel, 2010; Chen, 2010). Extracellularly, HMGB1 is a damage associated molecular pattern (DAMP) protein that acts as a pro-inflammatory molecule, orchestrating migration and activation of inflammatory cells to the injury site (Bianchi, 2017). HMGB1-dependent inflammation has been associated with ischemia-reperfusion and drug-induced liver injury (Huebener, 2015).

Acetaminophen (APAP), also known as paracetamol, is a widely used analgesic and is the active pharmaceutical ingredient of Tylenol®. Ingestion of a supratherapeutic dose causes acute liver failure (ALF) (Heard, 2008). The misuse of Vicodin® or Percocet®, co-formulations of opioids and APAP, can also cause ALF. In the US, nearly 50% of drug-induced liver injury has been attributed to APAP toxicity (Lee, 2007), which accounts for ~80,000 emergency room visits annually (Blieden, 2014). The mechanism for APAP toxicity begins with its metabolic conversion to the reactive chemical species, N-acetyl-p-benzoquinone imine (NAPQI), which causes hepatocyte necrosis. (Tacke, 2015). Necrotic hepatocytes release HMGB1 which drives chemotaxis of neutrophils through the receptor for advanced glycation end-products (RAGE), activating sterile inflammation and amplifying liver injury (Huebener 2015).

However, additional compositions and methods for treating inflammation in subject in need thereof remain a need in the art.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this summary does not list or suggest all possible combinations of such features.

In some embodiments, provided herein are small molecule compounds having an anti-inflammatory property, the small molecule compound comprising a non-anticoagulant heparan sulfate oligosaccharide molecule, optionally wherein the non-anticoagulant heparan sulfate oligosaccharide molecule is configured to interact with a high mobility group box 1 (HMGB1) protein in a manner sufficient to affect an interaction between the HMGB1 protein and a receptor for advanced glycation end products (RAGE). The oligosaccharide molecule can comprise about 10 to about 20 saccharide units, or about 12 to about 18 saccharide units. The oligosaccharide molecule can comprise about 18 saccharide units.

In some embodiments, provided herein is a small molecule compound comprising a disaccharide structure unit as shown:

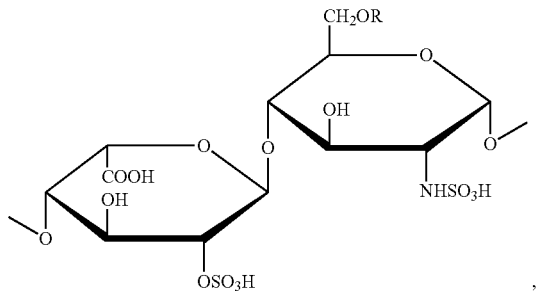

wherein R=—H or —SO$_3$H. The disaccharide structure unit can be selected from the group consisting of non-anticoagulant heparin, non-anticoagulant low-molecular weight heparin, and O-desulfated heparin (ODSH). In some embodiments, the oligosaccharide molecule protects against liver injury in vivo. In some embodiments, the oligosaccharide molecule decreases neutrophil infiltration in vivo. In some embodiments, the oligosaccharide molecule decreases inflammation in vivo.

Provided herein are methods of treating a subject, comprising providing a subject to be treated, wherein the subject is suffering from inflammation, and administering to the subject a non-anticoagulant heparan sulfate oligosaccharide molecule having an anti-inflammatory property, optionally wherein the non-anticoagulant heparan sulfate oligosaccharide molecule is configured to interact with a high mobility group box 1 (HMGB1) protein in a manner sufficient to affect an interaction between the HMGB1 protein and a receptor for advanced glycation endproducts (RAGE). In some embodiments, the subject suffers from any injury resulting in increased inflammation. In some embodiments, the subject suffers from liver injury. In some embodiments, the subject in need of treatment is a subject suffering from an overdose of Paracetamol (APAP). In some embodiments, the subject in need of treatment is a human subject. In some embodiments, the small molecule compound comprises a disaccharide structure unit selected from the group consisting of non-anticoagulant heparin, non-anticoagulant low-molecular weight heparin, and O-desulfated heparin (ODSH). In some embodiments, the oligosaccharide molecule comprises about 10 to about 20 saccharide units, or about 12 to about 18 saccharide units. In some embodiments, the oligosaccharide molecule comprises about 18 saccharide units. Administration of the oligosaccharide molecule can decrease neutrophil infiltration in the subject. Administration of the oligosaccharide molecule can decrease inflammation in the subject. Administration of the oligosaccharide molecule can protect against liver damage and multi-organ system failure in the subject. In some aspects, the subject to be treated suffers from drug-induced inflammation.

In some aspects, provided herein are methods of treating Paracetamol (APAP) overdose in a subject, the method comprising providing a subject in need of treatment for APAP overdose, administering to the subject a non-anticoagulant heparan sulfate oligosaccharide molecule having an anti-inflammatory property, optionally wherein the non-anticoagulant heparan sulfate oligosaccharide molecule is configured to interact with a high mobility group box 1 (HMGB1) protein in a manner sufficient to affect an interaction between the HMGB1 protein and a receptor for advanced glycation endproducts (RAGE), wherein damage from the APAP overdose in the subject is mitigated. The treatment for the APAP overdose in the subject can in some embodiments be effective between 0 hours and 24 hours after the overdose, or at least within 12 hours after the overdose. The treatment for the APAP overdose in the subject can comprise protection against liver injury and/or multi-organ system failure. The treatment for the APAP overdose in the subject can comprise a decrease in neutrophil infiltration in the subject. The treatment for the APAP overdose in the subject can comprise blocking the interaction between the HMGB1 protein and RAGE. In some aspects, the small molecule compound comprises a disaccharide structure unit as shown:

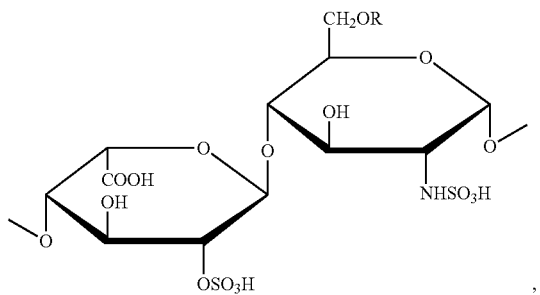

wherein R=—H or —SO$_3$H. The small molecule compound can comprise a disaccharide structure unit is selected from the group consisting of non-anticoagulant heparin, non-anticoagulant low-molecular weight heparin, and O-desulfated heparin (ODSH). The oligosaccharide molecule comprises about 10 to about 20 saccharide units, or about 12 to about 18 saccharide units. In some aspects, the oligosaccharide molecule comprises about 18 saccharide units.

Accordingly, it is an object of the presently disclosed subject matter to provide sulfated heparan sulfate oligosaccharide compounds having anti-inflammatory activity and methods for making and using the same.

This and other objects are achieved in whole or in part by the presently disclosed subject matter. Further, an object of the presently disclosed subject matter having been stated above, other objects and advantages of the presently disclosed subject matter will become apparent to those skilled in the art after a study of the following description, Drawings and Examples.

BRIEF DESCRIPTION OF THE DRAWINGS

The presently disclosed subject matter can be better understood by referring to the following figures. The components in the figures are not necessarily to scale, emphasis instead being placed upon illustrating the principles of the presently disclosed subject matter (often schematically). In the figures, like reference numerals designate corresponding parts throughout the different views. A further understanding of the presently disclosed subject matter can be obtained by reference to an embodiment set forth in the illustrations of the accompanying drawings. Although the illustrated embodiment is merely exemplary of systems for carrying out the presently disclosed subject matter, both the organization and method of operation of the presently disclosed subject matter, in general, together with further objectives and advantages thereof, may be more easily understood by reference to the drawings and the following description. The drawings are not intended to limit the scope of this presently disclosed subject matter, which is set forth with particularity in the claims as appended or as subsequently amended, but merely to clarify and exemplify the presently disclosed subject matter.

For a more complete understanding of the presently disclosed subject matter, reference is now made to the following drawings in which:

FIGS. 6A-6D are graphical depictions of data showing biological parameters of APAP overdosed mice;

FIGS. 8A-8D are graphical depictions of data showing the protective effects of 6-mer, 12-mer, 18-mer and 18-mer AXa oligosaccharide;

DETAILED DESCRIPTION

Figure 1A:
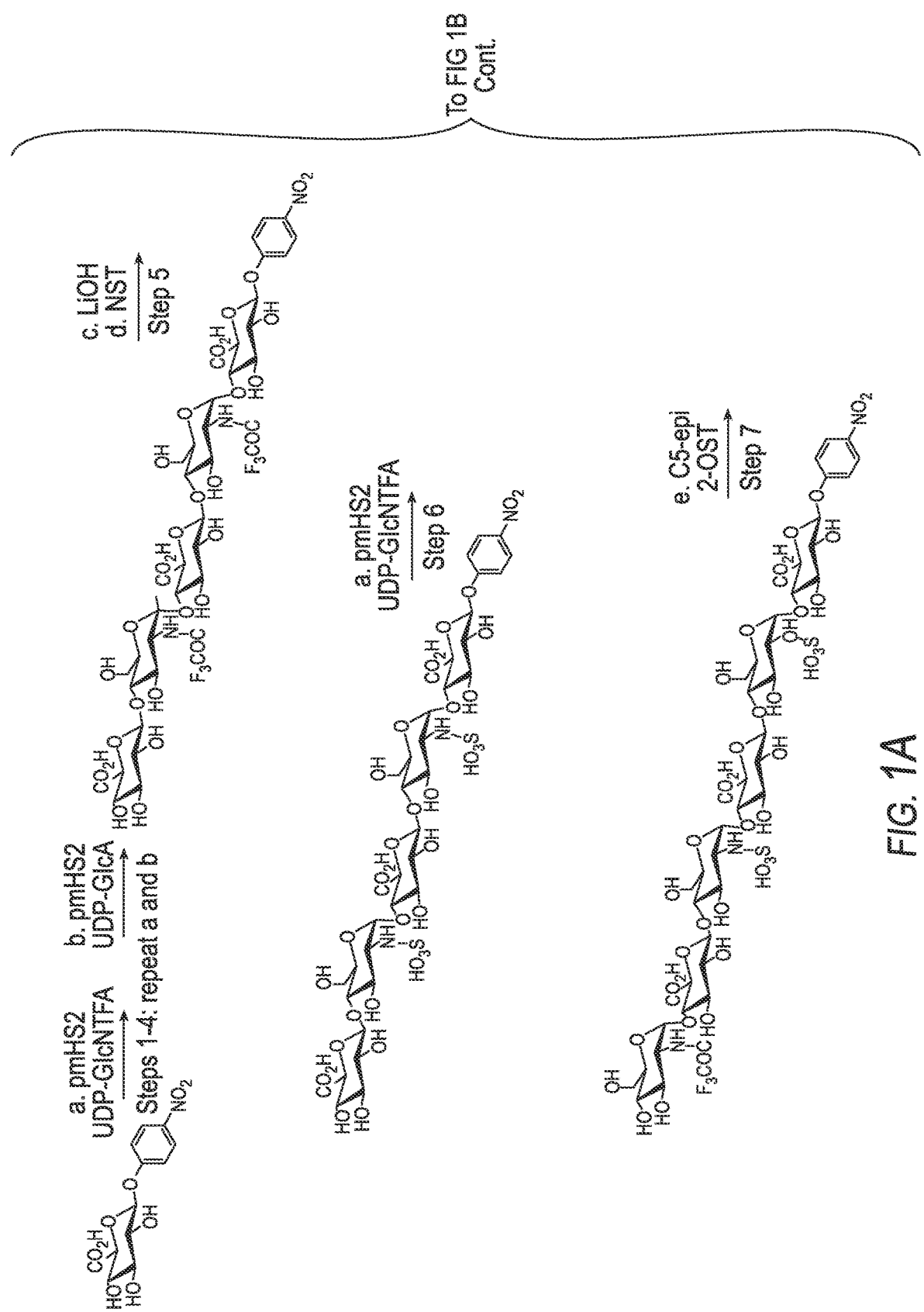
FIGS. 1A-1G are schematic illustrations of a chemoenzymatic synthetic pathway for the synthesis of 18-mer oligosaccharides.
Figure 1B:
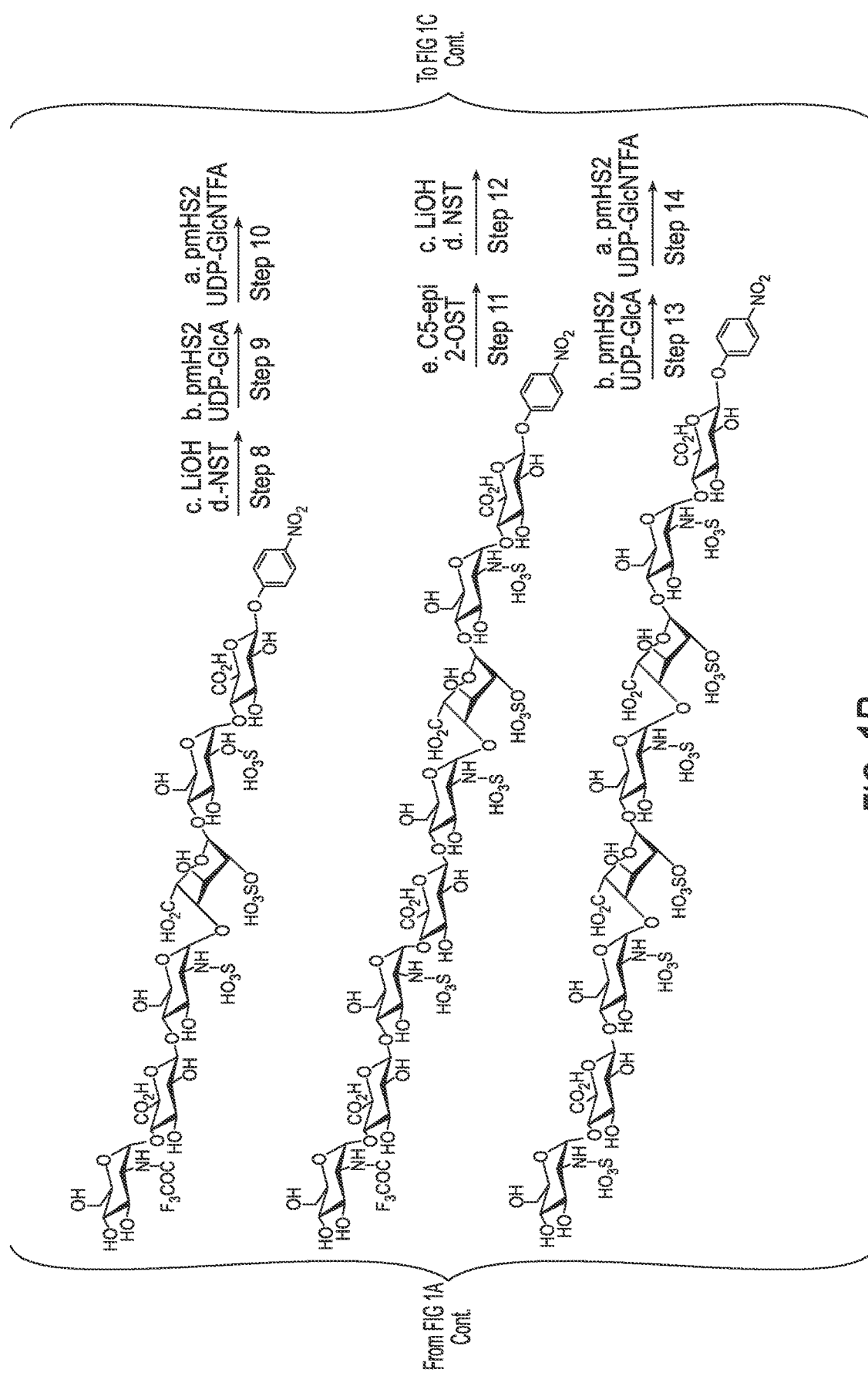
Figure 1C:
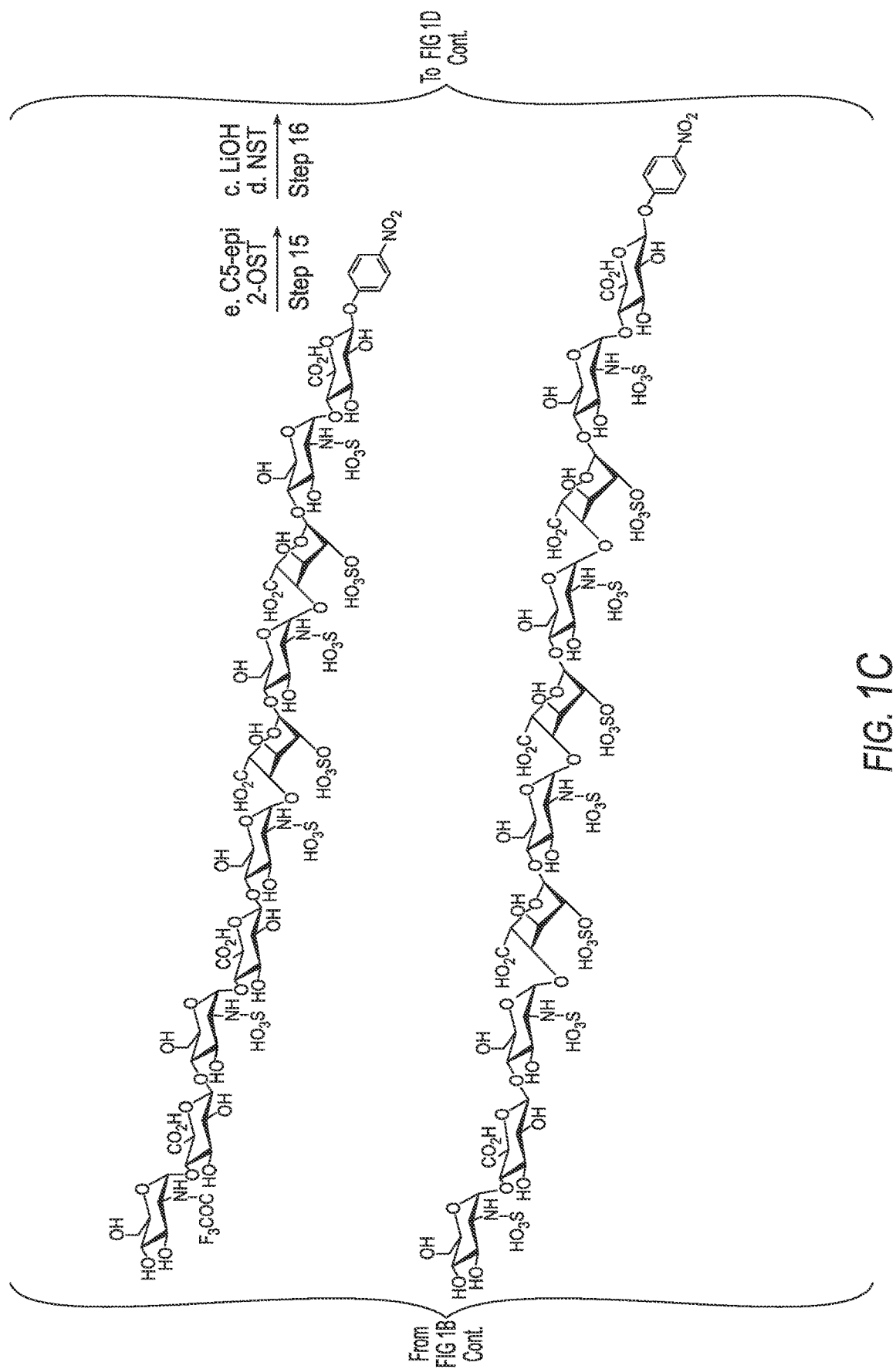
Figure 1D:
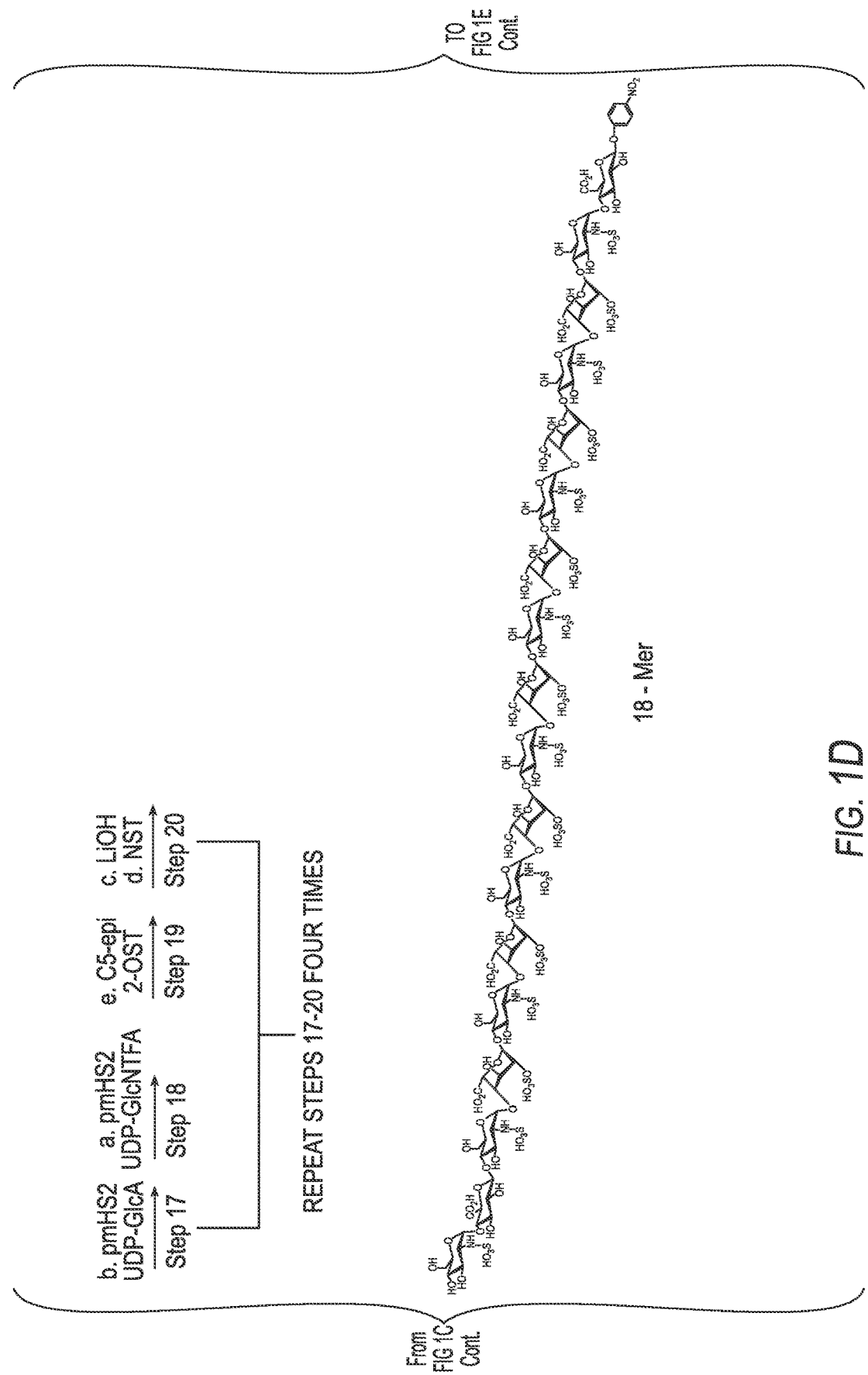
Figure 1E:
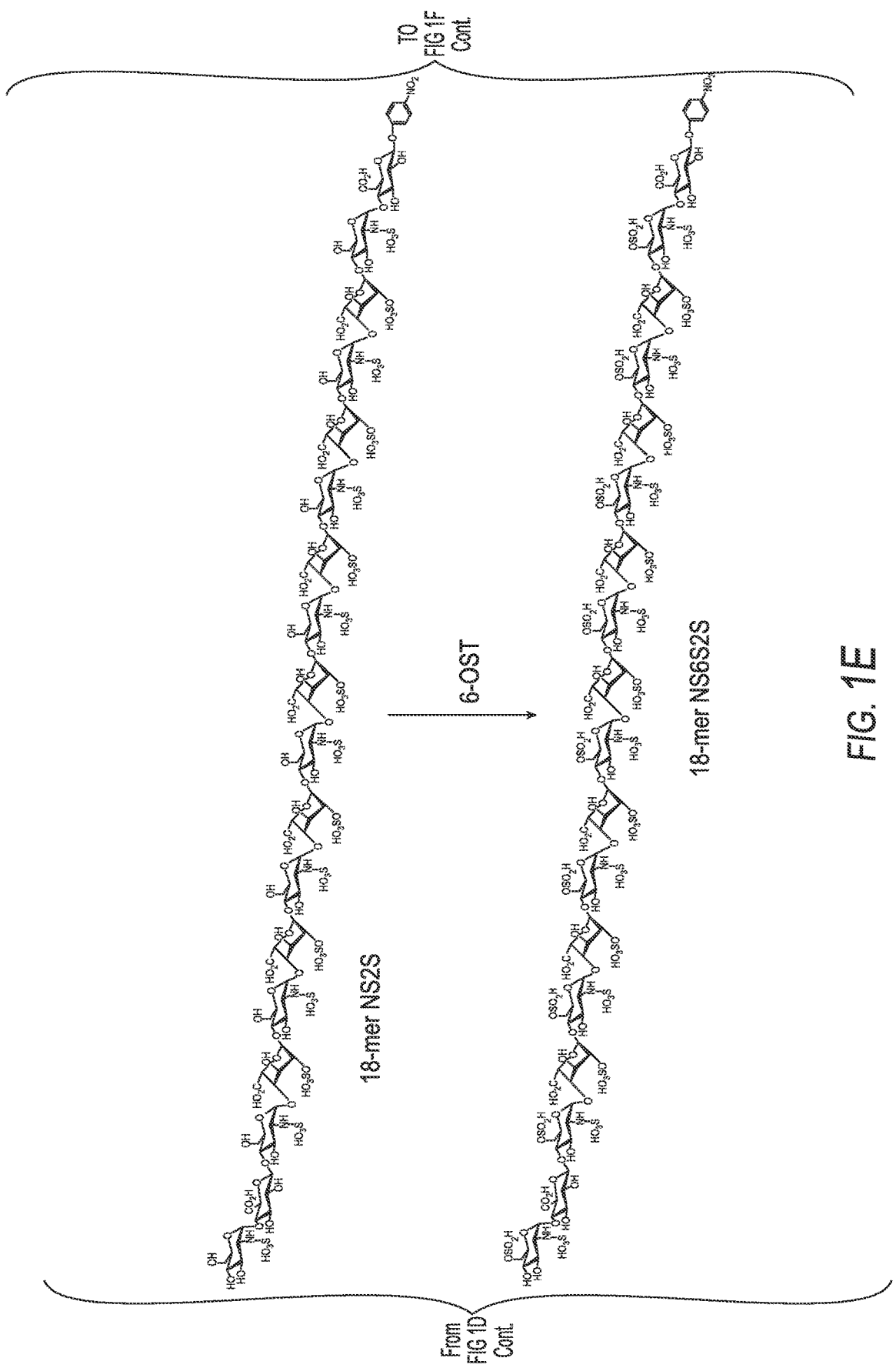
Figure 1F:
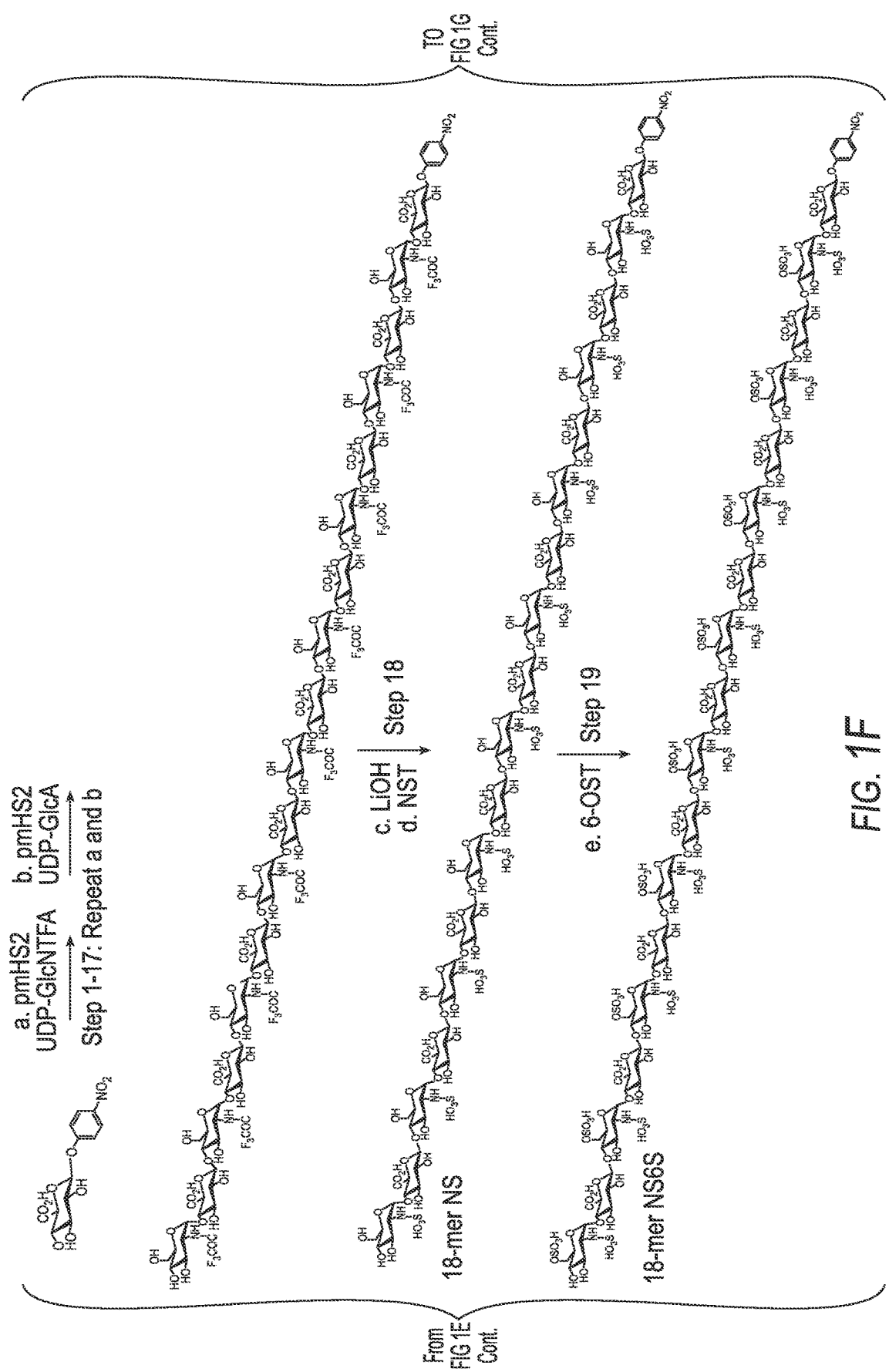
Figure 1G:
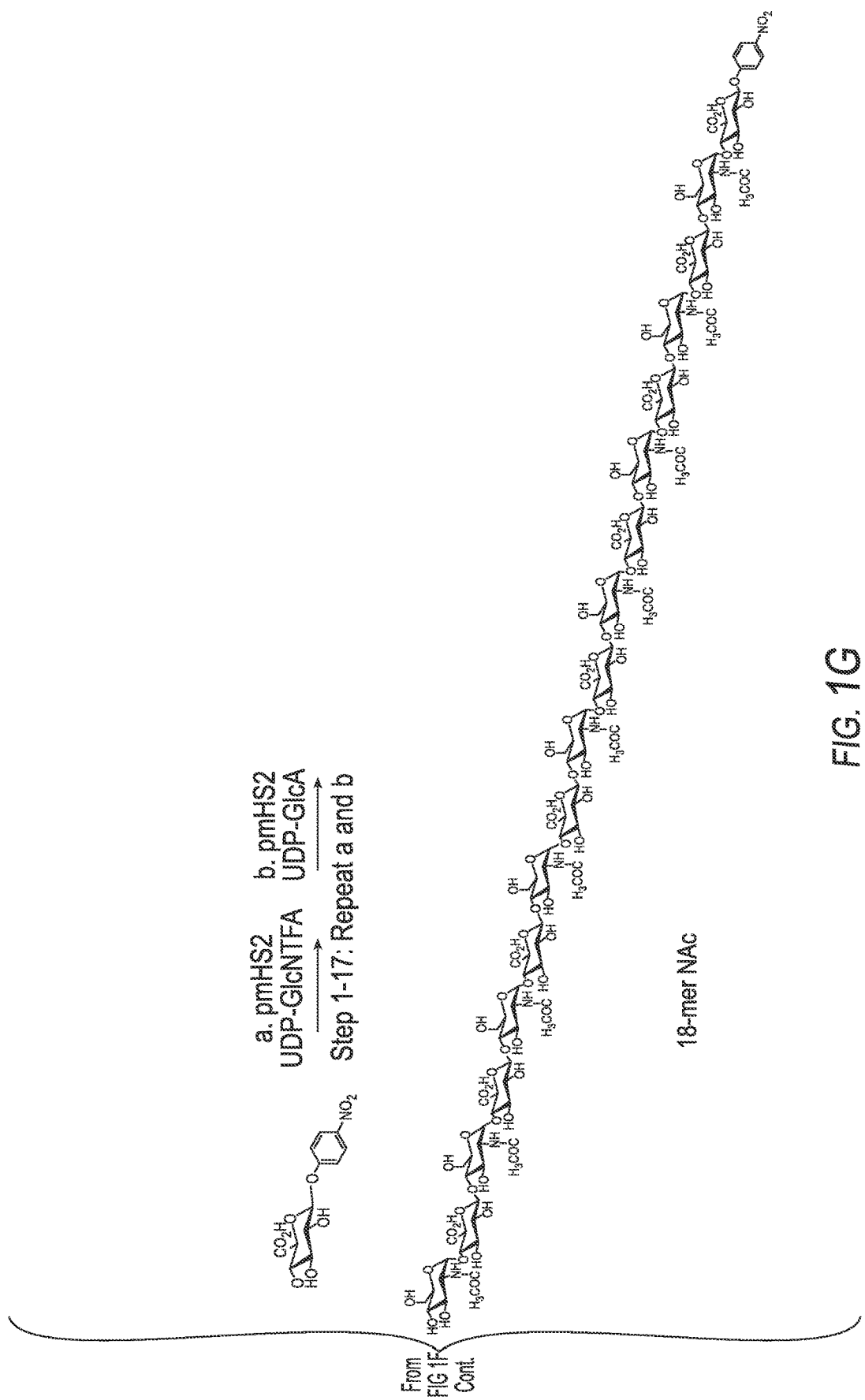
Figure 2:
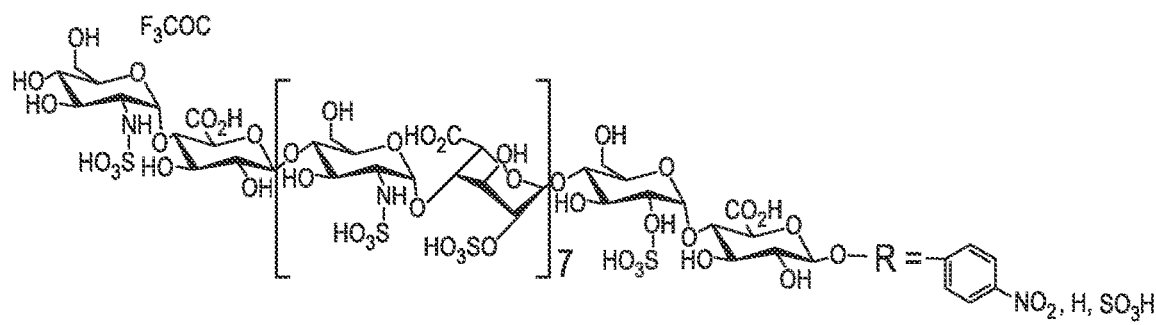
FIG. 2 is a schematic illustration of a chemical structure of an 18-mer oligosaccharide as disclosed herein.

The presently disclosed subject matter now will be described more fully hereinafter, in which some, but not all embodiments of the presently disclosed subject matter are described. Indeed, the presently disclosed subject matter can be embodied in many different forms and should not be construed as limited to the embodiments set forth herein; rather, these embodiments are provided so that this disclosure will satisfy applicable legal requirements.

Heparan sulfate (HS) is a sulfated polysaccharide abundantly present on cell surface and in extracellular matrix. Many DAMPs, including HMGB1, are HS-binding proteins (Xu, 2011). HS participates in various aspects of inflammation including chemokine presentation and neutrophil transendothelial migration (Proudfoot, 2003; Wang, 2005; Axelsson, 2013; and Sarris, 2012). HS is comprised of disaccharide repeating units of glucuronic acid (GlcA) or iduronic acid (IdoA) linked to glucosamine residues that carry sulfo groups. The chain length and sulfation pattern of HS determine its biological functions (Gama, 2006). In accordance with aspects of the presently disclosed subject matter, synthesis of a specially designed HS octadecasaccharide (18-mer) to exploit the anti-inflammatory effect is provided. The 18-mer protects APAP-induced acute liver failure through neutralizing the pro-inflammatory activity of HMGB1 in a murine model. The results presented offer a new chemical space to curb HMGB1-mediated inflammatory diseases.

In some embodiments, a small molecule compound with anti-inflammatory properties is disclosed. In some embodiments, the small molecule compound comprises a non-anticoagulant heparan sulfate oligosaccharide molecule with anti-inflammatory properties. In some embodiments, the non-anticoagulant heparan sulfate oligosaccharide molecule is configured to interact with a high mobility group box 1 (HMGB1) protein in a manner sufficient to affect an interaction between the HMGB1 protein and a receptor for advanced glycation endproducts (RAGE).

In some embodiments, a small molecule compound in accordance with the presently disclosed subject matter comprises, or can be part of a composition comprising, a disaccharide structure unit as shown:

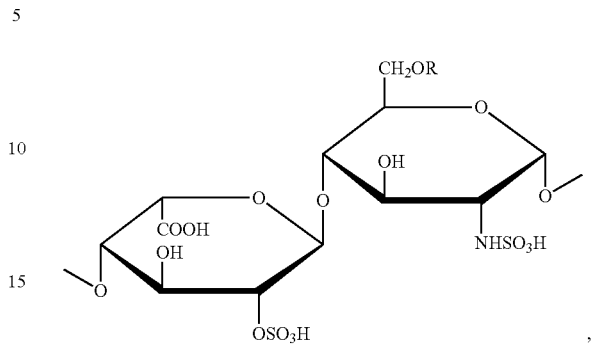

wherein R=—H or —SO$_3$H.

By way of example and not limitation, this disaccharide composition can be found in non-anticoagulant heparin, non-anticoagulant low-molecular weight heparin or O-desulfated heparin (ODSH). A composition in accordance with the presently disclosed subject matter can comprise a non-anticoagulant heparin, non-anticoagulant low-molecular weight heparin or O-desulfated heparin (ODSH).

In some embodiments, the oligosaccharide molecule comprises about 10 to about 20 saccharide units, or about 12 to about 18 saccharide units. In some embodiments, the oligosaccharide molecule comprises about 18 saccharide units. In some embodiments, generic structures of heparan sulfate oligosaccharides displaying anti-inflammatory effects comprise:

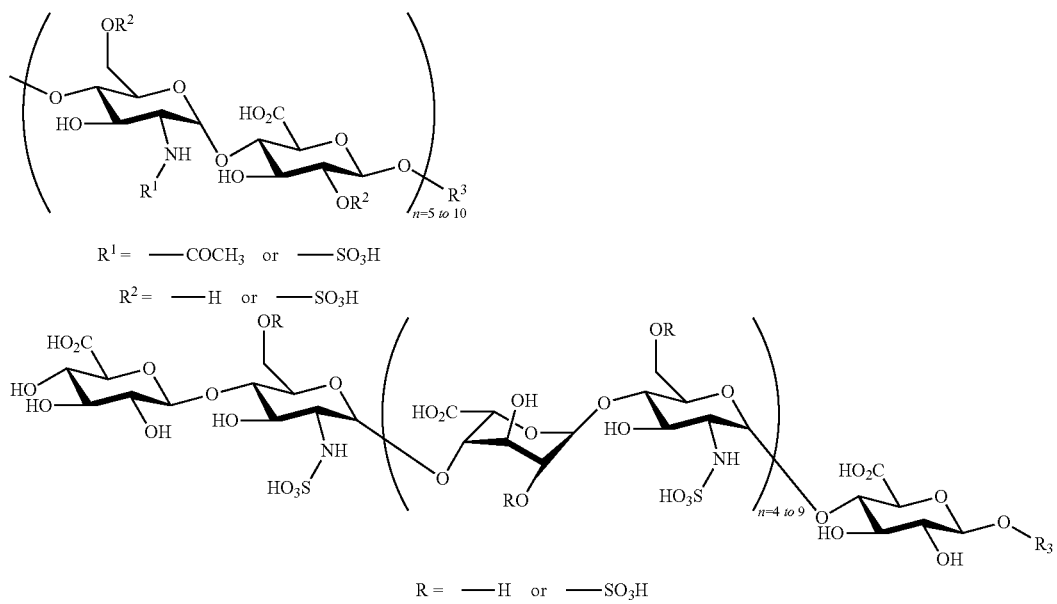

wherein R$^3$ is H or a detectable tag. In some embodiments, the detectable tag comprises para-nitrophenyl.

In some embodiments, the oligosaccharide molecule comprises one of the following structures:

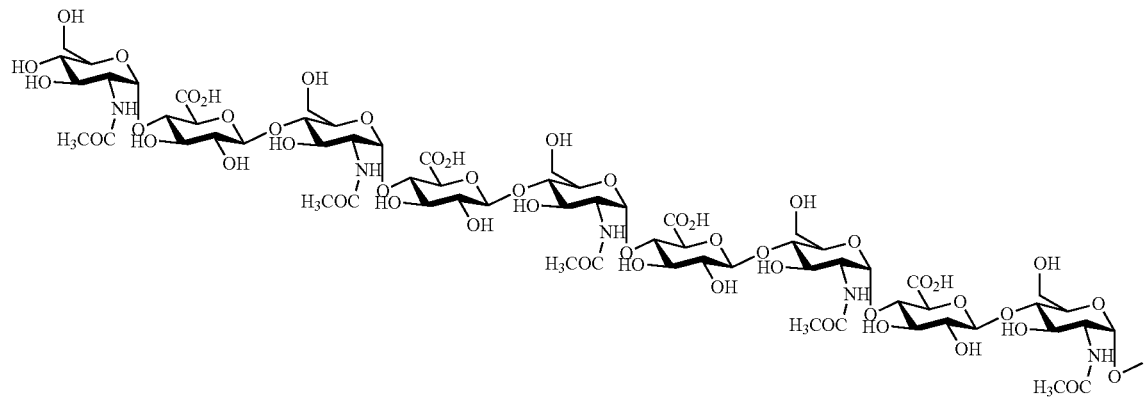
Structure 1 (NAc)
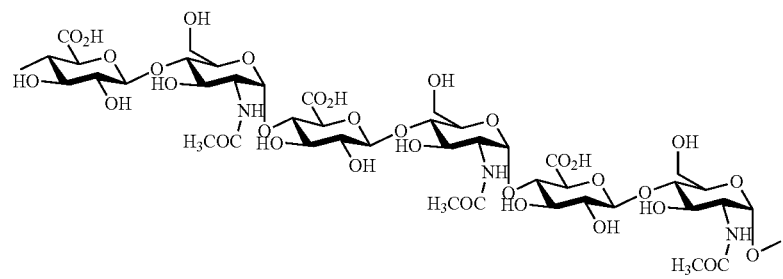
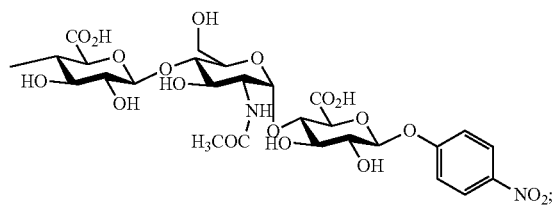
Structure 2 (NS)
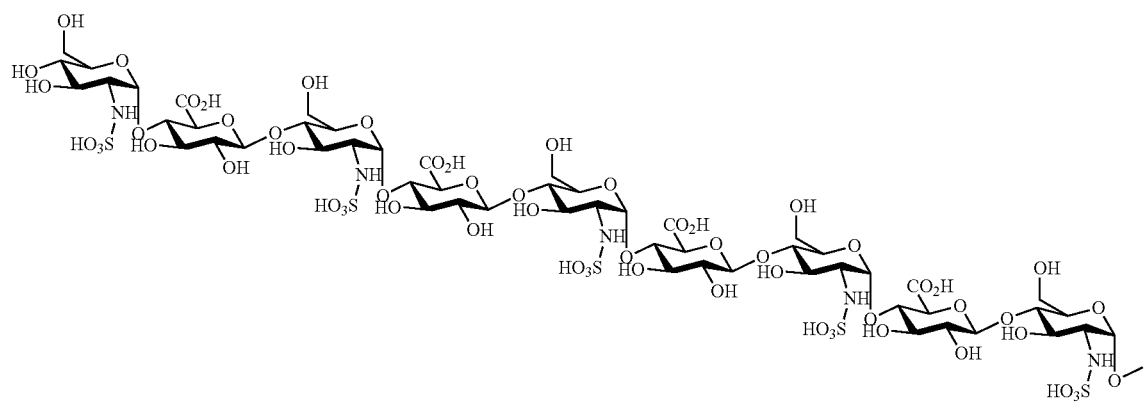
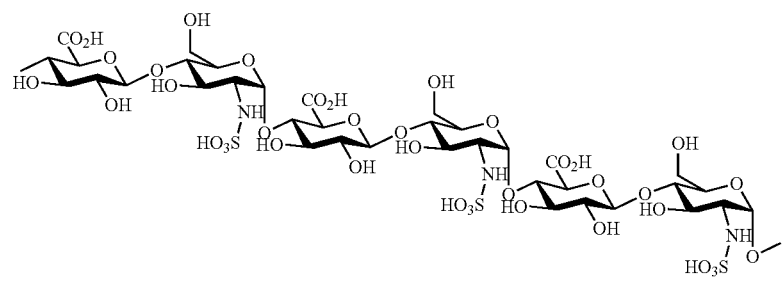

-continued
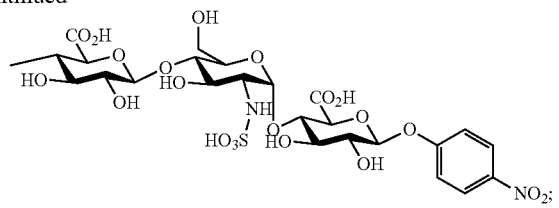
Structure 3 (NS6S)
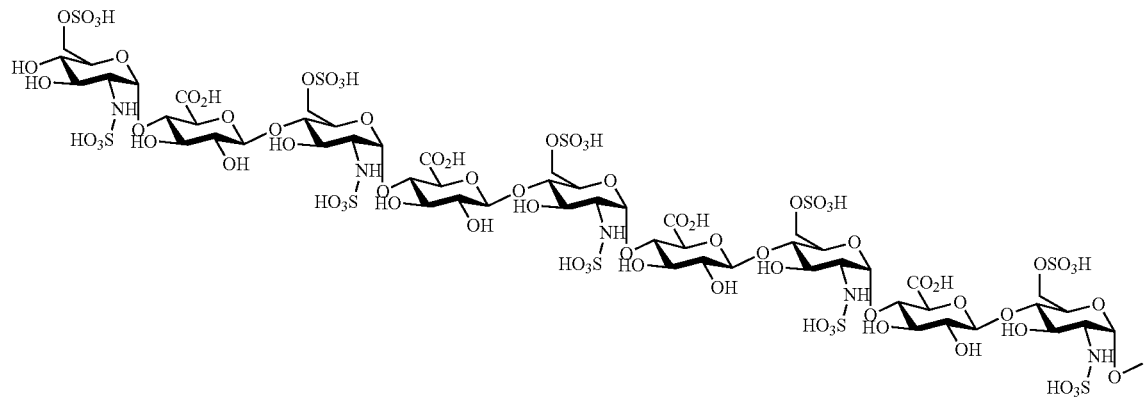
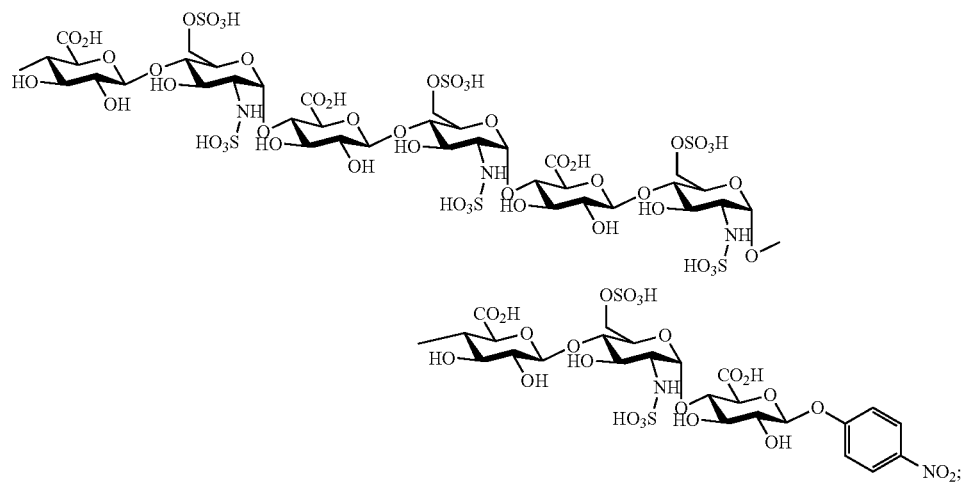
Structure 4 (NS2S)
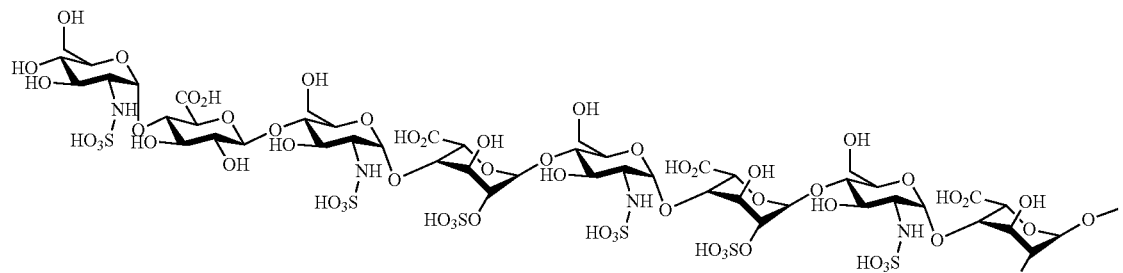
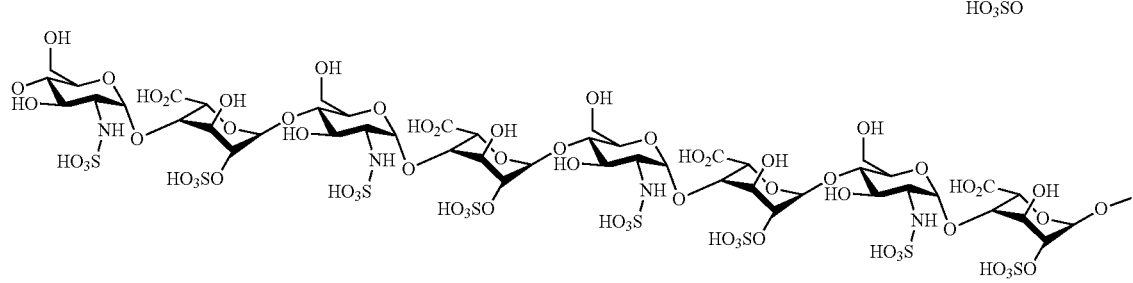

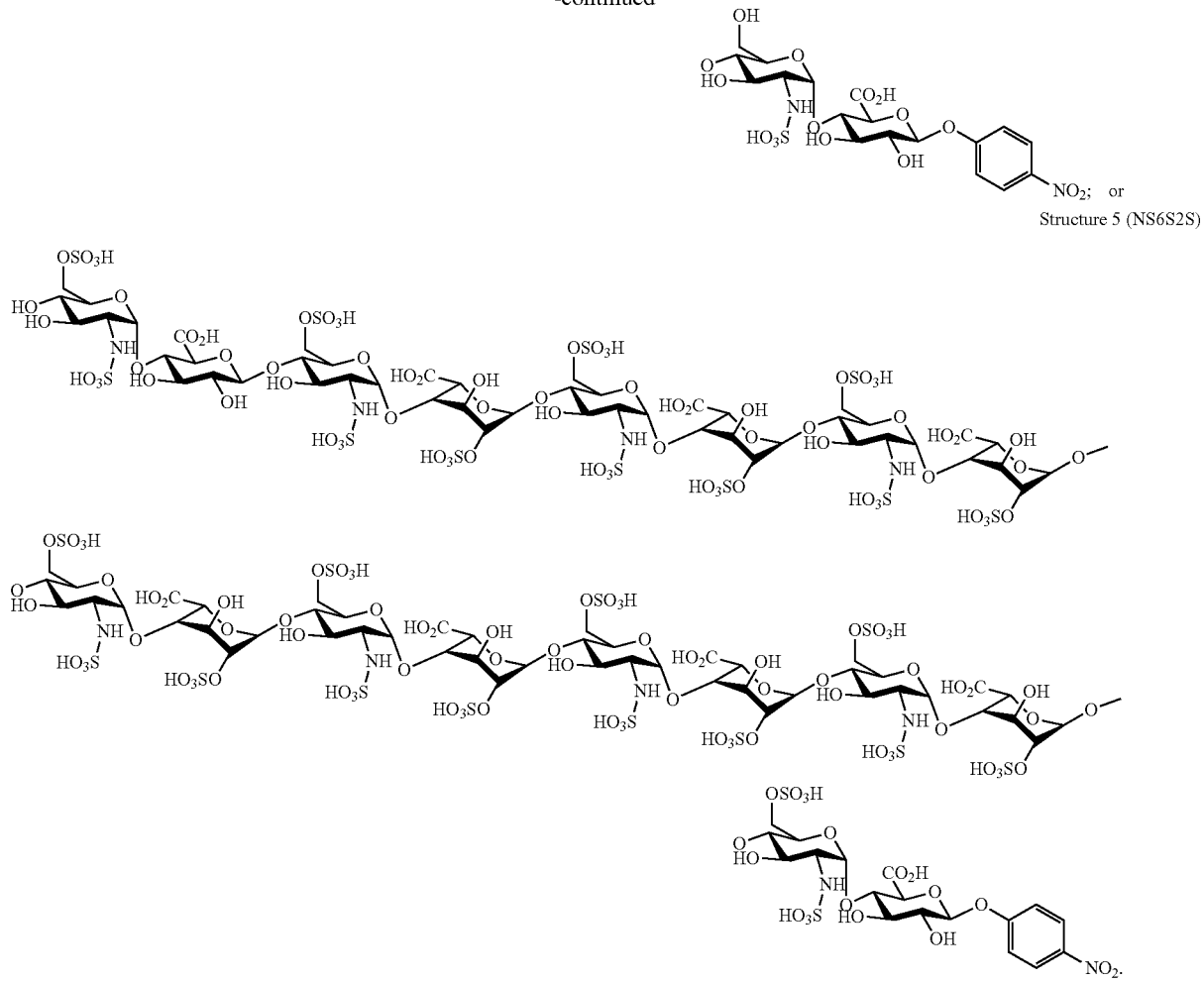

The compositions of the presently disclosed subject matter comprise in some embodiments a composition that includes a pharmaceutically acceptable carrier. Any suitable pharmaceutical formulation can be used to prepare the compositions for administration to a subject. In some embodiments, the composition and/or carriers can be pharmaceutically acceptable in humans.

For example, suitable formulations can include aqueous and non-aqueous sterile injection solutions that can contain anti-oxidants, buffers, bacteriostatics, bactericidal antibiotics, and solutes that render the formulation isotonic with the bodily fluids of the subject; and aqueous and non-aqueous sterile suspensions that can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are sodium dodecyl sulfate (SDS), in one example in the range of 0.1 to 10 mg/ml, in another example about 2.0 mg/ml; and/or mannitol or another sugar, for example in the range of 10 to 100 mg/ml, in another example about 30 mg/ml; and/or phosphate-buffered saline (PBS).

It should be understood that in addition to the ingredients particularly mentioned above, the formulations of this presently disclosed subject matter can include other agents conventional in the art having regard to the type of formulation in question. For example, sterile pyrogen-free aqueous and non-aqueous solutions can be used.

Methods of treating a subject are also provided in accordance with the presently disclosed subject matter, including but not limited to methods that treat conditions comprising inflammation. The therapeutic methods of the presently disclosed subject matter can comprise administering to the subject a non-anticoagulant heparan sulfate oligosaccharide molecule. In some embodiments, the non-anticoagulant heparan sulfate oligosaccharide molecule is configured to interact with a high mobility group box 1 (HMGB1) protein in a manner sufficient to affect an interaction between the HMGB1 protein and a receptor for advanced glycation endproducts (RAGE).

In some embodiments, the oligosaccharide molecule protects against liver injury in vivo. In some embodiments, the oligosaccharide molecule decreases neutrophil infiltration in vivo. In some embodiments, the oligosaccharide molecule decreases inflammation in vivo.

In some embodiments, the subject is suffering from inflammation. In some embodiments, the subject suffers from any injury resulting in increased inflammation. In some embodiments, the subject suffers from liver injury. In some embodiments, the subject in need of treatment is a subject suffering from an overdose of Paracetamol (acetaminophen or APAP).

In some embodiments, the subject treated in the presently disclosed subject matter is desirably a human subject, although it is to be understood the methods described herein are effective with respect to all vertebrate species (e.g., mammals, birds, etc.), which are intended to be included in the term "subject."

More particularly, provided herein is the treatment of mammals, such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Thus, the methods described herein include the treatment of livestock, including, but not limited to, domesticated swine (pigs and hogs), ruminants, horses, and the like.

In some embodiments, the oligosaccharide molecule decreases neutrophil infiltration in the subject. In some embodiments, the administration of the oligosaccharide molecule decreases inflammation in the subject. In some embodiments, the administration of the oligosaccharide molecule protects against liver damage and multi-organ system failure in the subject. In some embodiments, the subject to be treated suffers from drug-induced inflammation. In some embodiments, damage from the APAP overdose in the subject is mitigated.

In some embodiments, the treatment for the APAP overdose in the subject is effective between 0 hours and 24 hours after the overdose, or in some embodiments at least within 12 hours after the overdose, and in some embodiments within 6 hours after overdose. In some embodiments, the treatment for the APAP overdose in the subject comprises protection against liver injury and/or multi-organ system failure. In some embodiments, the treatment for the APAP overdose in the subject comprises a decrease in neutrophil infiltration in the subject. In some embodiments, the treatment for the APAP overdose in the subject comprises blocking the interaction between the HMGB1 protein and RAGE.

In some embodiments, a small molecule compound in accordance with the presently disclosed subject matter comprises a disaccharide structure unit as shown:

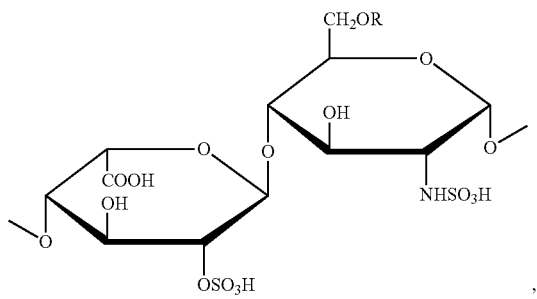

wherein R=—H or —SO$_3$H.

By way of example and not limitation, this disaccharide structure unit can be found in non-anticoagulant heparin, non-anticoagulant low-molecular weight heparin or O-desulfated heparin (ODSH). A composition employed in accordance with the presently disclosed methods can comprise a non-anticoagulant heparin, non-anticoagulant low-molecular weight heparin or O-desulfated heparin (ODSH). In some embodiments, the composition protects against liver injury in vivo, e.g., provides hepatoprotection in vivo. In some embodiments, the oligosaccharide molecule decreases neutrophil infiltration in vivo. In some embodiments, the subject suffers from liver injury. In some embodiments, the subject in need of treatment is a subject suffering from an overdose of Paracetamol (acetaminophen or APAP).

In some embodiments, the oligosaccharide molecule comprises about 10 to about 20 saccharide units, or about 12 to about 18 saccharide units. In some embodiments, the oligosaccharide molecule comprises about 18 saccharide units. In some embodiments, generic structures of heparan sulfate oligosaccharides displaying anti-inflammatory effects comprise:

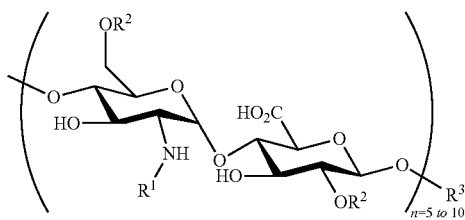

R$^1$ = —COCH$_3$ or —SO$_3$H

R$^2$ = —H or —SO$_3$H

-continued
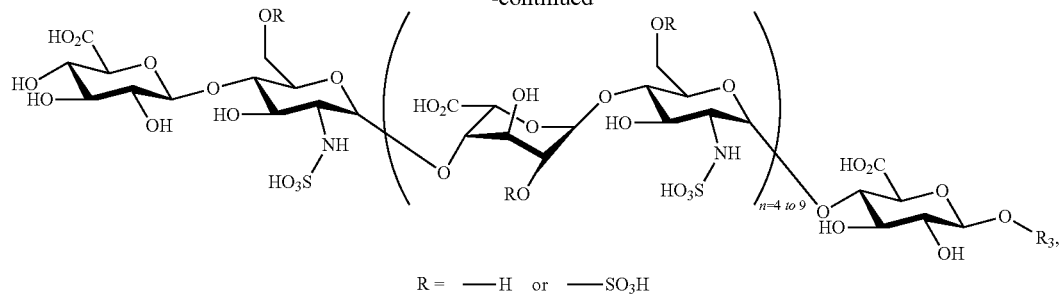
R = —H or —SO₃H
wherein $R^3$ is H or a detectable tag. In some embodiments, the detectable tag comprises para-nitrophenyl.
In some embodiments, the oligosaccharide molecule comprises one of the following structures:
Structure 1 (NAc)
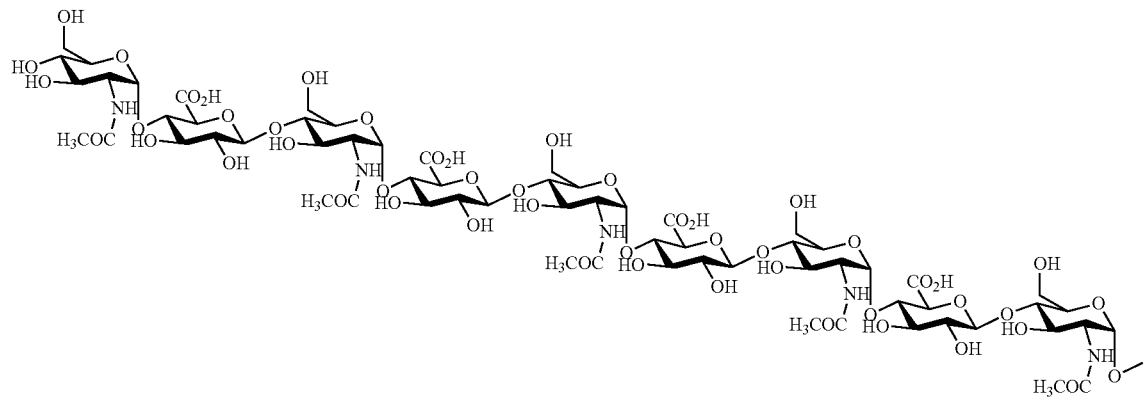
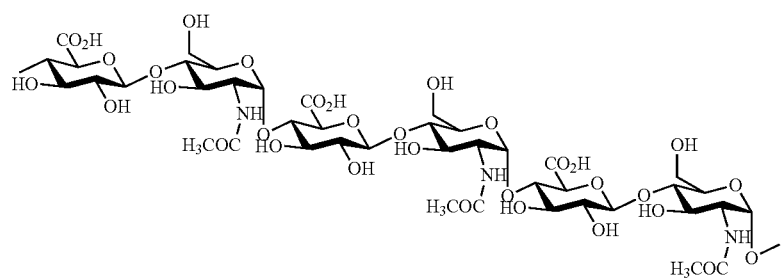
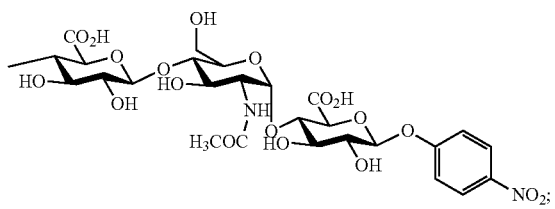

-continued
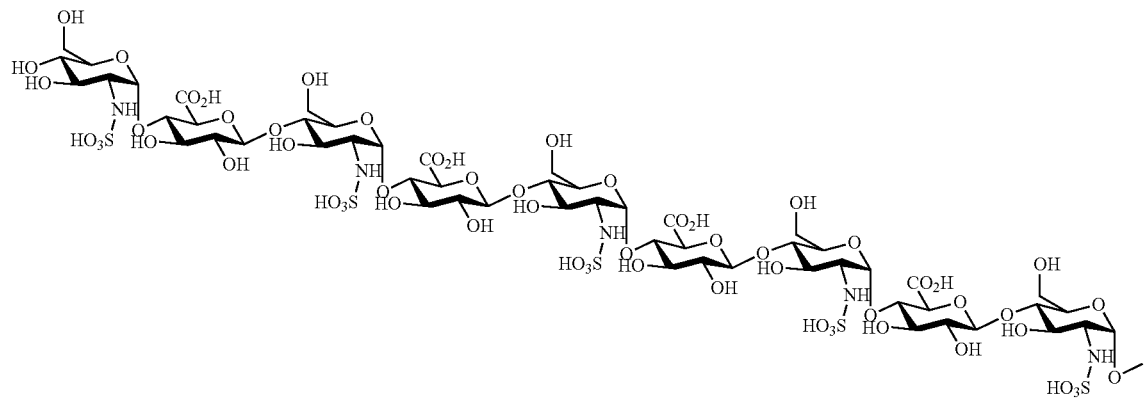
Structure 2 (NS)
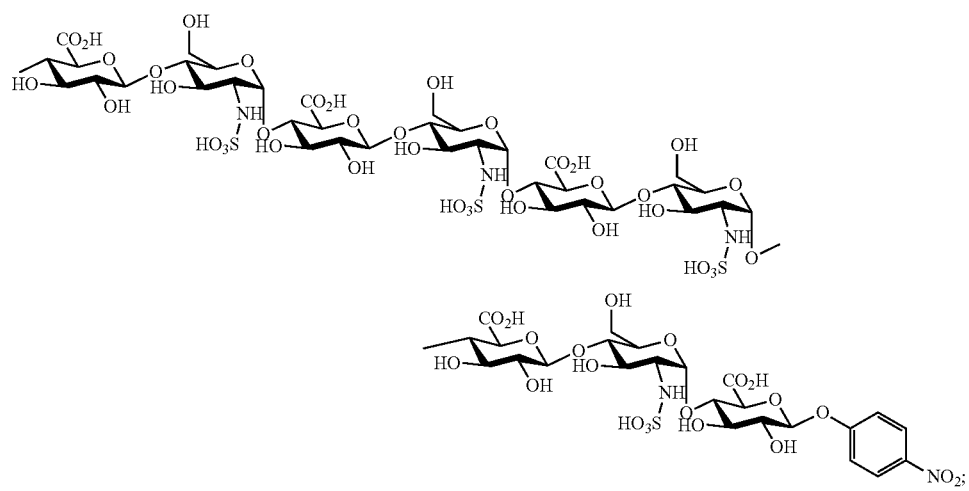
Structure 3 (NS6S)
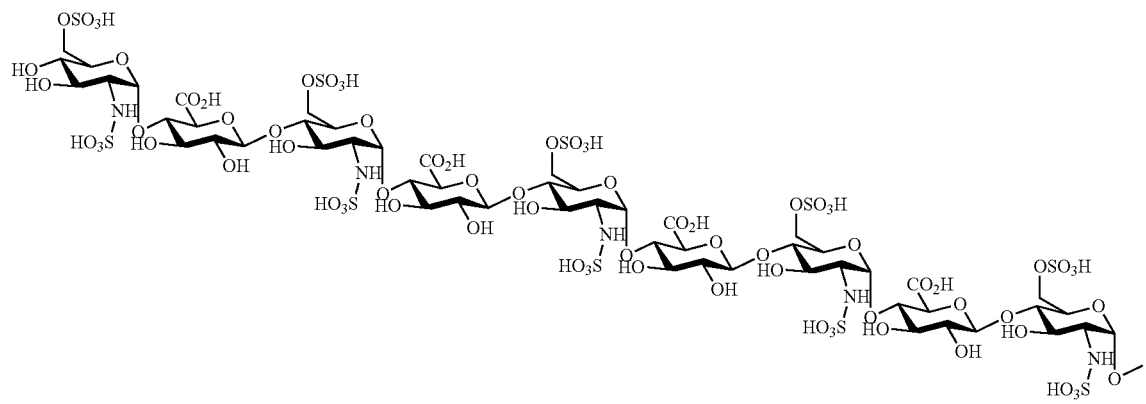
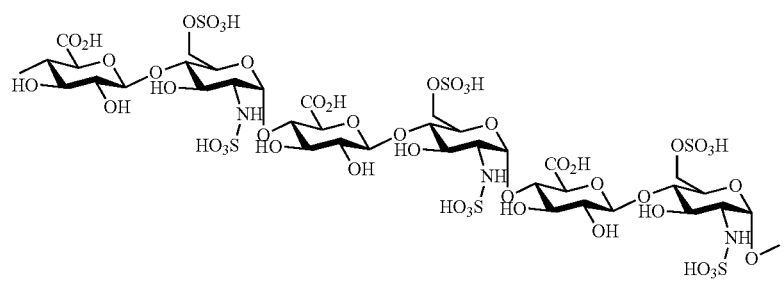

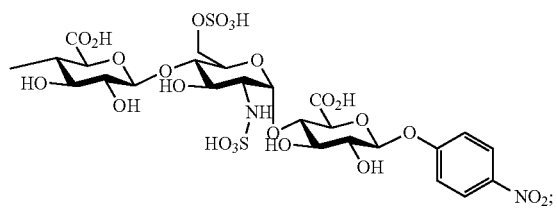
Structure 4 (NS2S)
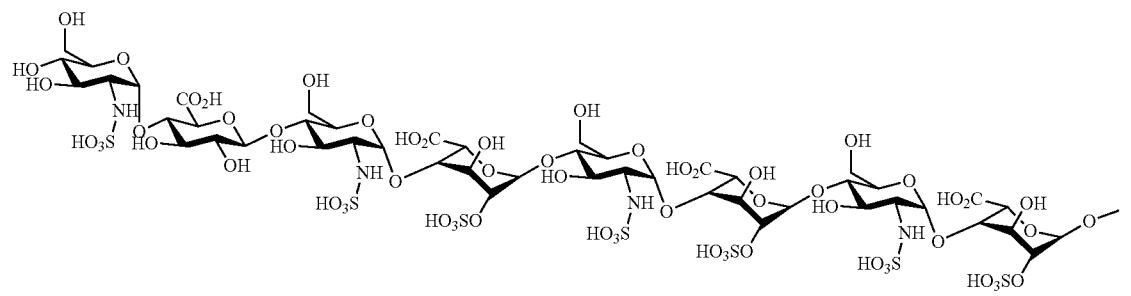
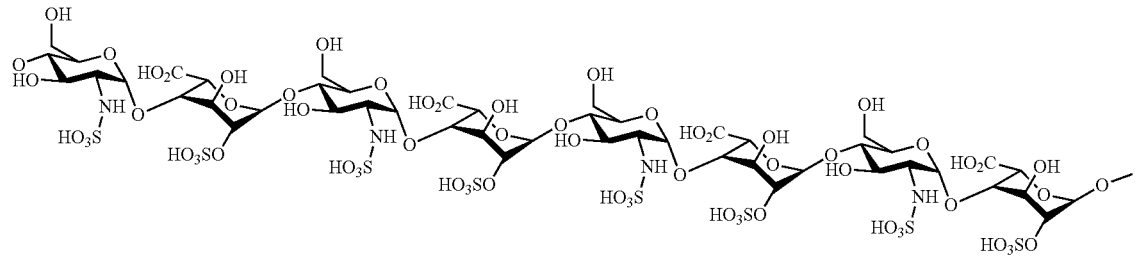
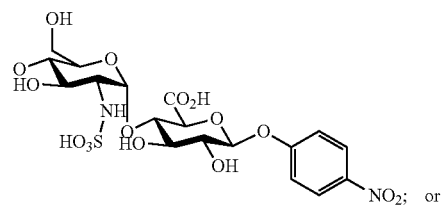
Structure 5 (NS6S2S)
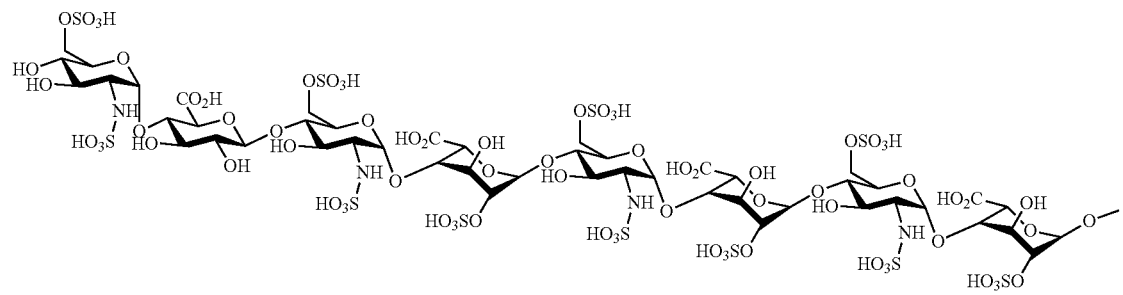
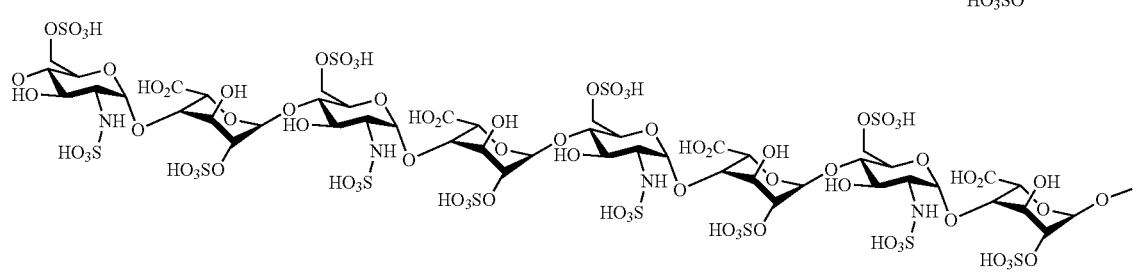

-continued

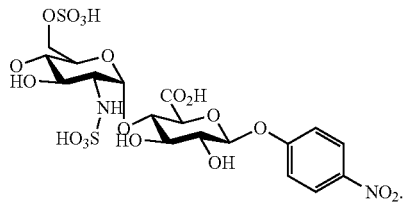

Definitions

The terminology used herein is for the purpose of describing particular embodiments only and is not intended to be limiting of the presently disclosed subject matter.

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one skilled in the art. While the following terms are believed to be well understood by one of ordinary skill in the art, the following definitions are set forth to facilitate explanation of the presently disclosed subject matter.

The term "non-anticoagulant" and phrase "without anticoagulant" used in this application describes presently disclosed subject matter having less than or equal to about 50 units/mg anticoagulant activity where the anticoagulant activity is attributed to inhibition of Factor Xa and/or Factor IIa.

In describing the presently disclosed subject matter, it will be understood that a number of techniques and steps are disclosed. Each of these has individual benefit and each can also be used in conjunction with one or more, or in some cases all, of the other disclosed techniques.

Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

Following long-standing patent law convention, the terms "a", "an", and "the" refer to "one or more" when used in this application, including the claims. Thus, for example, reference to "a unit cell" includes a plurality of such unit cells, and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of a composition, mass, weight, temperature, time, volume, concentration, percentage, etc., is meant to encompass variations of in some embodiments ±20%, in some embodiments ±10%, in some embodiments ±5%, in some embodiments ±1%, in some embodiments ±0.5%, and in some embodiments 0.1% from the specified amount, as such variations are appropriate to perform the disclosed methods or employ the disclosed compositions.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel_characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

EXAMPLES

The following examples are included to further illustrate various embodiments of the presently disclosed subject matter. However, those of ordinary skill in the art should, in light of the present disclosure, appreciate that many changes can be made in the specific embodiments which are disclosed and still obtain a like or similar result without departing from the spirit and scope of the presently disclosed subject matter.

Example 1

Acetaminophen/paracetamol (APAP) overdose is the leading cause of drug-induced acute liver failure (ALF) in the US and Europe. The progression of the disease is attributed to sterile inflammation induced by the release of high mobility group box 1 (HMGB1). A specific, effective and safe approach to neutralize the pro-inflammatory activity of HMGB1 is highly desirable. Disclosed herein in some embodiments is a HS octadecasaccharide (18-mer) that displays potent hepatoprotection by targeting to HMGB1. Investigation of the role of endogenous syndecan-1 in response to APAP overdose substantiated the mechanism for 18-mer's protection. The presently disclosed data suggest that 18-mer potentiates the host anti-inflammation effect mediated by syndecan-1. Finally, it is demonstrated that 18-mer administered six hours after APAP overdose is still protective, and therefore offers a therapeutic advantage over N-acetyl cysteine for late-presenting patients. Synthetic HS opens a new approach for the treatment of ALF and other HMGB1-involved inflammatory diseases A series of novel sulfated heparan sulfate oligosaccharide compounds were synthesized. In particular, chemoenzymatic synthesis was employed to obtain a pure HS/heparin-like oligosaccharide without anticoagulant activity One exemplary compound, termed 18-mer NS2S, was used for in depth in vivo studies in mice. 18-mer NS2S significantly decreased injury in the context of acetaminophen (APAP)-induced acute liver failure. Although it is not desired to be bound by any particular theory of operation, the mechanism of action of 18-mer NS2S likely involves the HMGB1/RAGE. 18mer NS2S treatment is still effective 6 hours after APAP overdose in mice whereas the clinically used antidote, NAC, loses effectiveness at this time. Additional description of these observations can be found in the Examples that follow.

Chemoenzymatic synthesis was used to generate novel, pure oligosaccharide compounds without anticoagulant activity. Representative synthetic routes are disclosed in the Examples that follow. A series of 18-mer compounds and one 12-mer, and one 6-mercompound were used in vivo. One exemplary 18-mer NS2S was shown to be protective against liver injury in vivo. In this example, 18-mer NS2S significantly increases the survival rate in vivo. 18-mer NS2S decreases neutrophil infiltration. RAGE knockout mice were observed to be insensitive to 18-mer NS2S's protective effects. This observation supports that delayed treatment after acetaminophen (APAP) overdose is possible.

Example 2

Materials and Methods

Study Design

This study was designed to synthesize a HS octadecasaccharide (18-mer) and evaluate its anti-inflammatory effect in an APAP-induced liver failure murine model. The chemoenzymatic synthesis of two HS 18-mers, including 18-mer NS2S (nonanticoagulant compound; referred to as 18-mer) and 18-mer AXa (anticoagulant compound) is demonstrated herein. The structures of two 18-mers were confirmed using both nuclear magnetic resonance (NMR) and high resolution mass spectroscopy (MS). Demonstration of the binding between HMGB1 and biotinylated 18-mer and 18-mer AXa was achieved using avidin-agarose column followed by western analysis. HMGB1 binds to 18-mer and 18-mer AXa in nanomolar ranges as determined by surface plasmon resonance (SPR). The hepatoprotection effect of the synthesized 18-mers was evaluated in a well-established APAP-induced liver failure murine model. The liver damage was assessed by two methods, including the plasma ALT level and examination of hematoxylin and eosin (H&E) stained liver sections. The inflammation responses after APAP overdose were assessed by determining the neutrophil migration to the injury sites. Factor Xa (FXa) activity was used as a surrogate to assess the anticoagulant activity of 18-mers, 12-mer and 6-mer in both in vitro and in vivo experiments. The number of animals in the tested groups and controls groups as well as statistical analysis are presented in the figure legends. Anonymous patient ALF plasma samples were obtained from the Acute Liver Failure Study Group (ALFSG) biorepository (of the National Institute of Diabetes and Digestive and Kidney Diseases, Bethesda, Maryland, United States of America) to determine the plasma level of shed syndecan-1. The analyses were stopped after analyzing 31 patient samples as a clear statistical difference between healthy control group (n=11) and AFL patients was observed.

Expression of HS Biosynthetic Enzymes

A total of nine enzymes was used for the synthesis, including NST, $C_5$-epi, 2-OST, 6-OST-1, 6-OST-3, 3-OST-1, 3-OST-5, and pmHS2. All enzymes, with the exception of $C_5$-epi and 2-OST, were expressed in E. coli and purified by appropriate affinity chromatography as described previously (Renpeng et al., 2010; Xu et al., 2008). Recombinant $C_5$-epi and 2-OST were expressed in insect cells using the Ba-to-Bac baculovirus expression approach (from Invitrogen) to obtain high expression levels (19). Three enzyme co-factors, including 3'-phosphoadenosine 5'-phosphosulfate (PAPS), uridine 5'-diphosphoglucuronic acid (UDP-GlcA), uridine 5'-diphospho N-trifluoroacetyl glucosamine (UDP-GlcNTFA), were all synthesized in-house using enzymatic approaches as described previously (Nam, 2017).

Synthesis of Non-Biotinyated 18-Mer AXa

The synthesis of 18-mer AXa was initiated from 18-mer. Two enzymatic modifications were added, including 6-O-sulfotransferases (6-OST) modification and 3-O-sulfotransferase isoform 1 (3-OST-1) modification. In the 6-O-sulfation step, the 18-mer (0.5 mM) was incubated in a buffer containing MES (50 mM, pH 7.0), 6-OST-1 (50 µg ml$^{-1}$), 6-OST-3 (50 µg ml$^{-1}$) and PAPS (1.5 equiv. of 6-hydroxyl group amount) at 37° C. overnight in 60 ml. The product was then purified by Q-Sepharose column for the subsequent 3-O-sulfation step.

The 3-O-sulfation step was completed by 3-OST-1 enzyme. The 6-O-sulfated 18-mer (0.5 mM) was incubated in a solution containing MES (50 mM) buffer (pH 7.0), 3-OST-1 (20 µg ml$^{-1}$) and PAPS (0.675 mM) in 20 ml at 37° C. for 2 hours. The product was purified by Q-Sepharose column. During the synthesis, the products were monitored by HPLC using a DEAE-NPR column (4.6 mm×75 mm, from Tosoh).

The synthesis of non-biotinylated 6-mer and non-biotinylated 12-mer was completed using the enzymatic method, and was reported previously (Xu, 2017).

Conversion of Nonbiotinylated Oligosaccharides to Biotinyated Oligosaccharides

Four nonbiotinylated oligosaccharides, 6-mer, 12-mer, 18-mer and 18-mer AXa, were converted to biotinylated counterparts. 6-mer, 12-mer, 18-mer and 18-mer AXa with a pNP tag (5-10 mg) and 0.5 mg Pd/C were dissolved in 20 mM NaOAc, pH 5.0 in a total volume of 4 ml. Reaction mixture was vacuumed and refilled with $H_2$ three times. The reaction was then incubated at room temperature for 4 h. After that, it was filtered to remove charcoal. The filtered solution was adjusted to pH 8.5 using 500 mM $Na_2HPO_4$. Succinimidyl 6-azidohexanoate (20 molar equivalent of starting oligosaccharides) was added and incubated at 37° C. overnight. Reaction was purified by DEAE-HPLC column to generate azido tagged oligosaccharides. PBS (pH7.4) buffer was bubbled with $N_2$ for 5 min to prepare the sample solution of 0.1M $CuSO_4$, 0.1M Tris(3-hydroxypropyl-trazolylmethyl)amine (THPTA) (Sigma, Burlington, Massachusetts, United States of America), 0.15M sodium ascorbate, 0.01M azido tagged oligosaccharides and 0.02 M biotin-PEG$_4$-alkyne (Sigma). The mixture of 400 µl THPTA and 80 µl $CuSO_4$ was vortexed, then 160 µl sodium ascorbate, 200 µl azido tagged oligomers and 200 µl biotin-PEG4-alkyne was added and bubbled with $N_2$ for 2 min, then incubated at 37° C. overnight. The reaction was purified by DEAE-HPLC column to generate biotinylated products. The reactions were monitored using HPLC and MS.

HPLC Analysis

Both DEAE-NPR HPLC and polyamine-based anion exchange (PAMN)-HPLC were used to analyze the purity of the products. The elution conditions for the HPLC analysis were described elsewhere (Renpeng et al., 2010). Briefly, for DEAE-HPLC method, the column TSK gel DNA-NPR (4.6×75 mm, from Tosoh Bioscience) was eluted with a linear gradient of NaCl in 20 mM sodium acetate buffer (pH 5.0) from 0 to 1M for 60 min at a flow rate of 0.4 ml $min^{-1}$. As for PAMN-HPLC, the column (Polyamine II-HPLC, 4.6×250 mm, from YMC) was eluted with a linear gradient of $KH_2PO_4$ from 0 to 1M for 40 min then remained at 1M for 30 min at a flow rate of 0.5 ml $min^{-1}$.

MS Analysis of Oligosaccharides

The low-resolution analyses were performed at a Thermo LCQ-Deca. Oligosaccharides were directly diluted in 200:1 of mixture of $MeOH/H_2O$ (9:1, vol/vol). A syringe pump (Harvard Apparatus) was used to introduce the sample by direct infusion (50 µl $min^{-1}$). Experiments were carried out in negative ionization mode. Synthetic nonsulfated oligosaccharides were diluted in 200 µl of $H_2O$ with the electrospray source set to 5 kV and 275° C. Sulfated oligosaccharides were diluted in 200 µl of 10 mM ammonium bicarbonate with the electrospray source set to 3 kV and 150° C. The automatic gain control was set to $1×10^7$ for full scan MS. The MS data were acquired and processed using Xcalibur 1.3.

High resolution ESI-MS analysis was conducted on Thermo LTQ XL Orbitrap (Breman, Germany) under the following conditions. A Luna hydrophilic liquid interaction chromatography (HILIC) column (2.0×50 $mm^2$, 200 Å, Phenomenex, Torrance, California, United States of America) was used to separate the oligosaccharide mixture. Mobile phase A was 5 mM ammonium acetate prepared with high performance liquid chromatography (HPLC) grade water. Mobile phase B was 5 mM ammonium acetate prepared in 98% HPLC grade acetonitrile with 2% of HPLC grade water. After injection of 5.0 µl 12-mer mixture (1.0 µg $µl^{-1}$) through an Agilent 1200 autosampler, HPLC binary pump was used to deliver the gradient from 3% A to 80% A over 10 min at a flow rate of 250 µl $min^{-1}$. The LC column was directly connected online to the standard electrospray ionization source of LTQ-Orbitrap XL Fourier transform (FT) mass spectrometer (MS) (Thermo Fisher Scientific, San-Jose, California, United States of America). The optimized parameters, used to prevent in-source fragmentation, included a spray voltage of 4.2 kV, a capillary voltage of −40 V, a tube lens voltage of −50 V, a capillary temperature of 275° C., a sheath flow rate of 40, and an auxiliary gas flow rate of 20. External calibration of mass spectra routinely produced a mass accuracy of less than 3 ppm. All FT mass spectra were acquired at a resolution of 60,000 with 200-2000 Da mass range.

LC/MS Disaccharide Analysis of Human Plasma Samples

Pooled individual plasma samples of healthy control subjects and APAP-ALF patients were digested in 300 µl digestion buffer (50 mM ammonium acetate containing 2 mM calcium chloride adjusted to pH 7.0). Recombinant heparin lyase I, II, III (pH optima 7.0-7.5) and recombinant chondroitin lyase ABC (10 mU each, pH optimum 7.4) were added to each sample and mixed well. The samples were all placed in a water bath at 37° C. for 12 h, after which enzymatic digestion was terminated by removing the enzymes by centrifugation. The filter unit was washed twice with 250 µl distilled water and the filtrates, containing the disaccharide products, were dried by vacuum centrifuge. The dried samples were AMAC-labeled by adding 10 µl of 0.1 M 2-aminoacridone (AMAC) in DMSO/acetic acid (17/3, vol/vol) incubating at room temperature for 10 min, followed by adding 10 µl of 1 M aqueous sodium cyanoborohydride and incubating for 1 h at 45° C. A mixture containing all 17-disaccharide standards purchased from Iduron (UK) prepared at 0.5 ng $µl^{-1}$ was similarly AMAC-labeled and used for each run as an external standard. After the AMAC-labeling reaction, the samples were centrifuged, and each supernatant was recovered. LC was performed on an Agilent 1200 LC system at 45° C. using an Agilent Poroshell 120 ECC18 (2.7 µm, 3.0×50 mm) column. Mobile phase A was 50 mM ammonium acetate aqueous solution, and the mobile phase B was methanol. The mobile phase passed through the column at a flow rate of 300 µl $min^{-1}$. The gradient was 0-10 min, 5-45% B; 10-10.2 min, 45-100% B; 10.2-14 min, 100% B; 14-22 min, 100-5% B. Injection volume is 5 µl. A triple quadrupole mass spectrometry system equipped with an ESI source (Thermo Fisher Scientific) was used as a detector. The online MS analysis was at the Multiple Reaction Monitoring (MRM) mode. MS parameters: negative ionization mode with a spray voltage of 3000 V, a vaporizer temperature of 300° C., and a capillary temperature of 270° C.

NMR Analysis

The NMR spectra of 18-mer and 18-mer AXa were obtained on Bruker 800 MHz standard-bore NMR spectrometer with TopSpin 2.1.6 software (Bruker, Billerica, Massachusetts, United States of America). Samples (3.0 to 6.0 mg) were each dissolved in 0.4 ml of 99.9% $D_2O$ centrifuged at 5000×g for 1 min and lyophilized. The process was repeated twice and the final sample was dissolved in 0.45 mL of 99.99% $D_2O$. 1H spectroscopy, $^1H$-$^1H$ correlated spectroscopy (COSY), $^1H$-$^{13}C$ heteronuclear single quantum coherence spectroscopy (HSQC), $^1H$-$^1H$ total correlation spectroscopy (TOCSY) and $^1H$-$^1H$ nuclear Overhauser effect spectroscopy (NOESY) experiments were all carried out at 298 K.

Expression of HMGB1

The complete open reading frame of human HMGB1 was cloned into pcDNA3.1(+)-C-6His (GenScript, Piscataway, New Jersey, United States of America). Transfection was performed using FectoPRO transfection reagent (Polyplus transfection). Recombinant HMGB1-his was produced in 293-freestyle cells (Thermo Fisher Scientific) at 31° C. Purification of HMGB1-his from cell lysate was carried out using Ni Sepharosem 6 Fast Flow gel (GE Healthcare, Little Chalfont, England) followed by Superdex200 gel filtration chromatography. After purification, HMGB1-his was >99% pure as determined by SDS-PAGE followed by silver staining. Endotoxin removal was performed using Detoxi-Gel (Thermo Fisher Scientific) and the final endotoxin level was <0.1 EU/µg protein by a Chromogenic LAL Endotoxin Assay (GenScipt, Piscataway, New Jersey, United States of America). The recombinant HMGB1-his had both cytokine and chemokine activities, which were assessed by a cell signaling assay and an air pouch assay (described in detail below), respectively.

Removal of Endotoxin from HS Oligosaccharides

Endotoxin was removed from HS oligosaccharides by using a 50 ml centrifugal filter unit (Amicon Ultra-15, Ultracel-100k; Merck Millipore, Darmstadt, Germany) at 4,000 rpm for 30 min. The process was repeated three times by refilling the filter insert with 1 ml of endotoxin-free water each time. The filtered solution was collected. The level of endotoxin was measured using the Limulus Amebocyte Lysate (LAL) kit (Associated of Cape Cod Inc.). The LAL test was performed by adding 100 µl of reconstituted Pyrotell (sensitivity 0.03 endotoxin units ml$^{-1}$) to 100 µl of 0.1 mg ml$^{-1}$ HS oligosaccharides in sterile saline which is the concentration used for animal injections. The Pyrotell and HS oligosaccharides were added to a 10 mm×75 mm depyrogenated glass reaction tube (Associates of Cape Cod Inc.) and incubated at 37° C. for 1 h. At the end of the incubation time, the tubes were inverted. If a gel clot forms, the sample is positive for endotoxin. If the sample remains in solution, the negative result implies that any endotoxin in the sample is below the sensitively of Pyrotell. All HS oligosaccharides solutions tested negative.

Histology/Immunohistochemistry

Liver tissues were fixed in 10% neutral buffered formalin for 24 h at room temperature, paraffin-embedded, and sectioned. Liver sections (4 µm) were stained with hematoxylin-eosin (H&E) or immunostained with monoclonal antibodies anti-neutrophil (Abcam, Ab 2557, NIMP-R14) (Abcam, Cambridge, United Kingdom) or anti-syndecan-1 (StemCell Technologies, 60035, done 281.2) (StemCell Technologies, Vancouver, Canada) and goat anti-rat biotinylated secondary antibodies (Abcam). For fibrin(ogen) staining, polydonal anti-fibrin(ogen) (Dako of Agilent, Santa Clara, California, United States of America) was used followed by goat anti-rabbit biotinylated secondary antibody (Sigma). Embedding, sectioning and H&E staining were performed at the Animal Histopathology and Laboratory Medicine Core Facility at UNC Chapel Hill. H&E analyses were performed by the Translational Pathology Laboratory Core Facility at UNC Chapel Hill using Aperio ImageScope Software (Leica Biosystems, Concord, Canada). IHC images were captured using an HD camera attached to a bright field microscope (Leica DM 1000 LED, Leica Microsystems Inc., IL, USA) and were processed using ImageJ. For neutrophil quantitation, five 100× images were randomly selected for each sample and the average neutrophils-field were reported.

Mouse Models of Inflammation: Peritonitis and Air Pouch

Two models were used to study in vivo neutrophil migration: peritonitis and an air pouch inflammation model. For the peritonitis model, 30 mg of liver lysate was injected into the peritoneal cavity of the mouse in the absence or presence of 20 µg of 18-mer. After 20 h, the mice were euthanized via inhalation of isofluorane and the peritoneal cavity was washed with 10 ml of ice cold PBS. The peritoneal lavage was used to determine neutrophil migration using flow cytometry.

In the air pouch technique, 3 ml of sterile air is injected under the skin on the back of the mouse. Three days later, the pouch is refilled with sterile air. On the sixth day, 5 µg of recombinant HMGB1 in the absence or presence of 22.3 µg of 18-mer were injected into the air pouch. Control mice were injected with 2 mg ml$^{-1}$ BSA in PBS. After 4 hours, mice were euthanized by isofluorane inhalation and the air pouch was washed with PBS only. The lavage was used to determine neutrophil migration using flow cytometry.

Flow Cytometry

Peritoneal and air pouch lavages were stained with fluorescently labeled antibodies against Ly-6G/Ly-6C (monoconal anti-mouse RB6-8C5, PE-Cy7, eBioscience) and Cd11b (monodonal anti-mouse M1/70, FITC, eBioscience). Samples were run on a Strategdim S1000Exi flow cytometer.

Immunoblot

Liver lysate was prepared by snap freezing tissue in liquid nitrogen at the time of sacrifice. The tissue was mechanically homogenized in buffer containing 200 mM MES, 500 mM phosphate, and 1 mM EDTA at pH 6 followed by three rounds of freeze thawing. The lysed sample were centrifuged at 10000×g for min at 4° C. Biotinylated HS oligosaccharides (final concentration 15 µM) were mixed with 100 µl of fresh liver lysate (~12.5 mg) and incubated overnight at 4° C. Pierce High Capacity Streptavidin Agarose (Thermo Fisher Scientific) was used to isolated biotinylated HS oligosaccharide bound complexes. After washing with 50 mM MES, 50 mM NaCl pH 6, samples were eluted with LDS buffer. Eluted samples were separated using NuPAGE 4-12% Bis-tris protein gels and assayed using anti-HMGB1 antibody (Abcam, rabbit monoclonal EPR3507) and goat anti-rabbit HRP (Abcam).

Preparation of $^{38}$S-Labeled HS and Binding Studies to Recombinant HMGB1

[$^{35}$S]HS was prepared using [$^{35}$S]PAPS (4×10$^7$ cpm) and N-sulfotransferase (NST) (100 µg ml$^{-1}$), and HS from bovine kidney in 50 mM MES in a total volume of 2 ml. The [$^{35}$S]HS (1.35×10$^5$ cpm) was incubated with 1 µg of recombinant HMGB1 in 50 mM MES, 70 mM NaCl, 10 mM imidazole at pH 6 and incubated at room temperature for 30 min. 5 µg chromatin immunoprecipitation grade anti-HMGB1 (Abcam) was added and incubated for 1 h at 4° C. Reaction mixtures were purified using Dynabeads Protein A (Thermo) and eluted in a buffer containing 25 mM Tris, 150 mM NaCl at pH 7.5. The eluted samples were measured for [$^{35}$S] counts using a liquid scintillation analyzer (Packard; GMI, Ramsey, Minnesota, United States of America). [$^{35}$S] HS in the absence of recombinant HMGB1 serves as a negative control.

Surface Plasmon Resonance

The biotinylated HS 18-mers (18-mer and 18-mer AXa) were immobilized to streptavidin (SA) sensor chips (BIAcore, GE Healthcare, Uppsala, Sweden) based on the manufacturer's protocol. In brief, 20 µl of biotinylated HS oligosaccharides were injected over flow cells 2,3, and 4 (FC2, FC3, and FC4) of the SA chip at a flow rate of 10 µl min$^{-1}$. The successful immobilization of biotinylated oligosaccharides were confirmed by the observation of a 563, 823, 505, 553 and 176 resonance unit (RU) increase, respectively on the SA chip. The control flow cell (FC1) was prepared by 1 min injection with saturated biotin.

Recombinant HMGB1 was diluted in 0.01 M HEPES, 0.15 M NaCl, 3 mM EDTA, and 0.005% surfactant P20 at pH 7.4. Recombinant HMGB1 at concentrations of 1000, 500, 250, 125 and 63 nM were injected at a flow rate of 30 µl min$^{-1}$. At the end of the recombinant HMGB1 injection, the same buffer was flowed over the SA surface to facilitate dissociation. After a 3 min dissociation time, the SA surface was regenerated by injecting 30 µl of 2 M NaCl. The response was monitored as a function of time (sensogram) at 25° C. The sensograms of various recombinant HMGB1 concentrations were globally fitted with 1:1 Langmuir model. SPR measurements were performed on a BIAcore 3000 operated using BIAcore 3000 control and BIAevaluation software (version 4.0.1)

APAP-ALF Patient Plasma

APAP-ALF patient plasmas, containing 1.8 mg ml$^{-1}$ EDTA, were obtained from the Acute Liver Failure Study Group (ALFSG) biorepository (of the National Institute of Diabetes and Digestive and Kidney Diseases, Bethesda, Maryland, United States of America). Details on the study design and collection methods are described previously (35).

Briefly, starting in 1998, adult patients who met the inclusion and exclusion criteria were enrolled in the ALFSG Registry. Plasma samples were obtained on admission to the Registry. In this study, only the plasma from APAP-overdosed patients was analyzed. Clinical data including the estimated quantity of APAP ingested, estimated time from ingestion to hospitalization, intentionality of overdose and patient demographics (age, gender, race, comorbidities, etc.), were not revealed for this study. Plasma syndecan-1 levels were measured using an ELISA kit (Human syndecan-1 ELISA, CellSciences, Newburyport Massachusetts, United States of America) according to the manufacturer's protocol. Plasma HMGB1 levels were measured using an HMGB1 ELISA according the manufacturer's protocol. Plasma ALT levels were measured using ALT Infinity Reagent.

Determination of the In Vitro and Ex Vivo Anti-FXa Activity

Assays were based on a previously published method (19). Briefly, human FXa (Enzyme Research Laboratories, South Bend, Indiana, United States of America) was diluted to 50 U ml$^{-1}$ with PBS. The chromogenic substrate S-2765 (Diapharma, West Chester, Ohio, United States of America) was diluted to 1 mg ml$^{-1}$ in water. For in vitro studies, Fondaparinux and HS oligosaccharides (18-, 12-, 6-, and 18-mer AXa) were dissolved in PBS at various concentrations (11-131 nM). 16 µl of sample was incubated with 60 µl of 35 µl ml$^{-1}$ antithrombin (Cutter Biologics) for 2 min at room temperature. Next, 100 µl of FXa was added and incubated for 4 min at room temperature. 30 µl of S-2765 substrate was added and the absorbance of the reaction mixture was measured at 405 nm continuously for 5 min. PBS serves as a control sample. The maximum slope for each sample was convert to percent FXa activity by dividing by the maximum slope for the control sample.

For ex vivo studies, mouse plasma collected 24 h post-APAP overdose in mice treated with APAP only, 18-mer, and 18-mer AXa were used and the same protocol was following.

Statistical Analysis

All data are expressed as mean SEM. Statistical significance between experimental and control groups were analyzed by two-tailed unpaired Student t test, between multiple groups by one-way ANOVA followed by Dunnett's or Tukey's multiple comparison's test, and Kaplan-Meier survival curves by log-rank test using GraphPad Prism software (version 7.03; GraphPad Software, Inc., LaJolla, California, United States of America).

Example 3

Synthesis of HS 18-Mer

The synthesis of 18-mer was completed according to the chemoenzymatic method published previously (17, 31). Briefly, heparosan synthase-2 (PmHS2) from *Pasteurella multocida* was used to elongate the monosaccharide, GlcA-pNP, to appropriate sized backbones. The backbone was then subjected to the modification of N-sulfotransferase (NST), C$_5$-epimerase (C$_5$-epi), and 2-O-sulfotransferase (2-OST). There were five major steps involved in the overall synthesis, including Step a (elongation step to add GlcNTFA), Step b (elongation step to add GlcA), Step c (detrifluoroacetylation using LiOH), step d (N-sulfation step), step e (2-O-sulfation/epimerization) (FIGS. 1A-1G).

Step a was to elongate the oligosaccharide backbone to the desired size, involving the addition of GlcNTFA residue. Briefly, GlcA-pNP (3.2 mM) was dissolved in buffer containing Tris (25 mM, pH 7.2), MnCl$_2$ (5 mM), pmHS2 (60 µg ml$^{-1}$) and UDP-GlcNTFA (4.5 mM), then incubated at 30° C. overnight. The total reaction volume was 4 L. A C$_{18}$-column (3×15 cm, or 120 g, Biotage) was used for purification with gradient elution method (0-100% methanol in H$_2$O, 0.1% trifluoroacetic acid, 5 ml min$^1$).

Step b was to elongate with a GlcA residue. A disaccharide (3.2 mM) was dissolved in a buffer containing Tris (25 mM, pH 7.2), MnCl$_2$ (5 mM), pmHS2 (30 µg ml$^{-1}$) and UDP-GlcA (1.5 mM), then incubated at 30° C. overnight. The total reaction volume was 3 l. A C$_{18}$-column (3×15 cm, or 120 g, Biotage) was used for purification as described above.

Step c was to convert a GlcNTFA residue to a GlcNH$_2$ residue under alkaline conditions. The detrifluoroacetylation of oligosaccharide (13 mM) was conducted in 0.1 M LiOH under ice bath for 0.5 h. The products were monitored by electrospray ionization mass spectrometry (ESI-MS). After the reaction was completed, the pH was immediately adjusted to 7.0 using hydrochloric acid (1 M).

Step d was to convert a GlcNH$_2$ residue to a GlcNS residue using NST enzyme. In one example, the detrifluoroacetylated tetrasaccharide (1.3 mM, GlcNH$_2$-GlcA-GlcNH$_2$-GlcA-pNP) incubated with N-sulfotransferase (32 µg mi) and PAPS (1.5 equiv. of free amino group amount) in a solution containing 2-(N-morpholino) ethanesulfonic acid (MES, 50 mM) pH 7.0 at 37° C. overnight in a reaction volume of 5.6 L.

Step e was to convert an internal GlcA residue to an IdoA2S residue and involves both C$_5$-epimerase and 2-O-sulfotransferase (2-OST). For example, the oligosaccharide GlcNTFA-GlcA-GlcNS-GlcA-GlcNS-GlcA-pNP (1.2 mM) was incubated in a solution containing Tris (25 mM) buffer (pH 7.5) and semi-purified C$_5$-epimerase (3 µg ml), 2-OST (6.5 µg ml$^{-1}$) and PAPS (1.8 mM) at 37° C. overnight in a reaction volume of 4.9 L.

The sulfated products were purified using Q-Sepharose fast flow column (from GE Healthcare Life Science) and eluted with a linear gradient 0-100% 2 M NaCl in 20 mM NaOAc-HOAc, pH 5.0 in 3 h. Different sizes of Q-Sepharose columns and salt gradients were chosen based on the binding affinity of the product and reaction scale.

At every elongation synthesis step, the products were monitored by Shimadzu HPLC equipped with a polyamine II column (4.6 mm×250 mm, from YMC). The structures of the intermediates from each step were characterized by electrospray ionization mass spectrometry (ESI-MS).

Example 4

Mouse Model of APAP Liver Injury

All animal experiments were approved by the Institutional Animal Care and Use Committee of University of North Carolina at Chapel Hill (Chapel Hill, North Carolina, United States of America) and the IACUC of the University at Buffalo (Buffalo, New York, United States of America). Ager$^{-/-}$ mice were originally gifted by Dr. Angelika Bierhaus (University of Heidelberg, Heidelberg, Germany) (32). C57BL/6J or Ager$^{-/-}$ mice were fasted overnight (12-15 h) to deplete glutathione stores before APAP (Sigma) administration. Fresh APAP was dissolved in warm (~50° C.) sterile 0.9% sodium chloride solution (sterile saline), cooled to 37° C., and injected intraperitoneal at 400 or 600 mg kg$^{-1}$. In some experiments, mice were injected subcutaneously at 30 min post-APAP with 9.5 µM HS oligosaccharide in ~200

µl sterile saline and again at 12 hours post-APAP with 4.75 µM HS oligosaccharide in ~100 µl or equivalent volumes of sterile saline.

To compare the 18-mer's effectiveness to N-acetyl cysteine (NAC), 300 mg kg$^{-1}$ NAC at pH 7.5 in sterile saline was injected intraperitoneal 30 min post-APAP. In a separate experiment, 300 mg kg$^{-1}$ NAC or 0.34 mg/kg 18-mer were administered 6 h post-APAP, then at 18 h post-APAP, 0.17 mg kg$^{-1}$ 18-mer was administered to the 18-mer treated group. At 24 h post-APAP, mice were euthanized and blood and liver tissue were collected.

In the survival study (600 mg kg$^{-1}$ APAP), mice were injected 30 min post-APAP with 0.4 mg kg$^{-1}$ 18-mer followed by repeat injections every 12 h or equivalent volumes of sterile saline for 96 h.

Example 5

Evaluation of APAP-Induced Liver Injury

Plasma ALT was measured using the ALT Infinity reagent (Thermo Fisher Scientific) following the manufacturer's instructions. Plasma TNF-α was measured using Mouse TNF-α DuoSet Kit (R&D Systems, Minneapolis, Minnesota, United States of America) according to the manufacturer's instructions. Plasma HMGB1 levels were determined using HMGB1 ELISA Kit (Tecan US of Tecan Trading AG, Mannedorf, Switzerland) according to the manufacturer's instructions. Plasma syndecan-1 levels were determined using Mouse Syndecan-1 ELISA (CellSciences) according to manufacturer's instructions. Hepatic GSH levels were determined using Glutathione Assay Kit (Cayman Chemicals, Ann Arbor, Michigan, United States of America) according to the manufacturer's instructions.

Example 6

18-Mers Significantly Decrease Liver Injury 36 Hours after APAP Overdose

Similar to the above examples, C57Bl/6J male mice, at about 10 weeks of age and about 25 grams of body weight, were overdoses with acetaminophen (APAP; 400 mg/kg) via intraperitoneal injection at time 0 hr.

Mice received repeat subcutaneous injections of 18-mers 30 minutes, 12 hours and 24 hours after APAP. The mice were sacrificed via cervical dislocation, blood was drawn from the vena cava, and liver tissue was harvested for histology. Alanine aminotransferase (ALT) was used as a biomarker for liver injury. Tumor necrosis factor-α (TNF-α) was used as a marker for inflammation. Hematoxylin and Eosin staining (H&E) was used as the histological staining technique to quantitate regions of tissue necrosis.

The resulting data showed that all 18-mer compounds (Table 1) decreased plasma ALT levels. Although all 18-mers tested were effective, the NS2S sulfation pattern provided the most consistent decrease in ALT (largest difference of means compared to APAP control), results of which are presented in Table 1.

TABLE 1

| Comparison | N APAP; N = 19 | Difference of Means | P |
|---|---|---|---|
| 18mer NS2S | 17 | 2928 | <0.001 |
| 18mer NS6S | 17 | 2261 | <0.001 |
| 18mer NS6S2S | 14 | 1779 | <0.001 |
| 18mer NS | 12 | 1682 | <0.001 |
| 18mer NAc | 7 | 1356 | 0.014 |

Example 7

Results and Discussion

HS isolated from natural sources is highly complex mixtures with different polysaccharide chain lengths and sulfation patterns. Lack of structurally homogeneous HS oligosaccharides, especially long HS oligosaccharides that display similar functions of full length HS, hampers the efforts to exploit the interests of HS as a therapeutic agent (Liu, 2014). We have recently developed a chemoenzymatic method to synthesize HS oligosaccharides with excellent efficiency (Xu, 2011, Xu 2014, Xu, 2017). Here, HS oligosaccharides, including 323 mg of an HS otadecasaccharide (18-mer), were synthesized (FIGS. 1A-1G and FIG. 2). This represents one of the longest HS oligosaccharides synthesized to date. The structure of 18-mer was confirmed by high resolution mass spectrometry and NMR. The purity was determined to be >98% by high resolution anion exchange high-performance liquid chromatography.

Figure 3A:
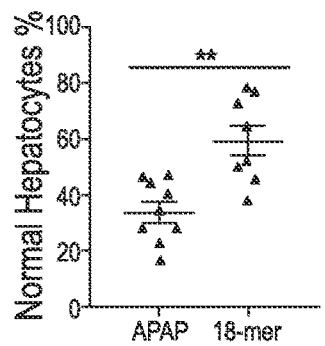
FIGS. 3A through 3D are graphical depictions of data showing the effects of an 18-mer oligosaccharide on liver injury after APAP overdose.
Figure 3B:
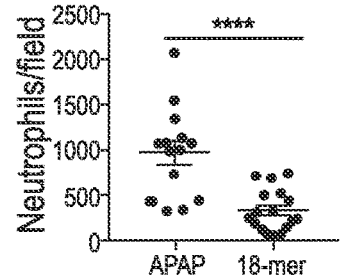
Figure 3C:
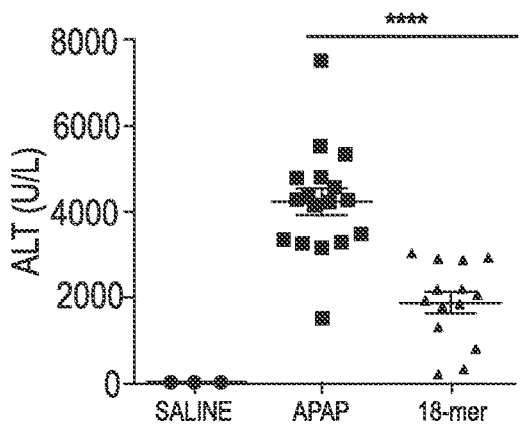
Figure 3D:
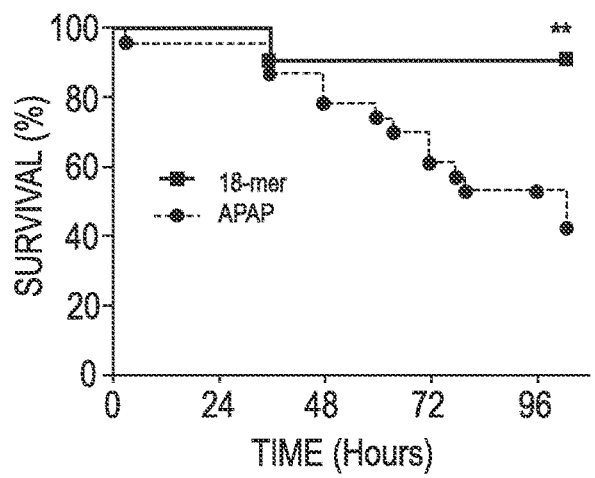

The hepatoprotective effects of 18-mer were examined in an APAP-induced ALF murine model. Mice treated with 18-mer after APAP overdose had significantly healthier livers than APAP control mice as indicated by a higher population of normal hepatocytes (FIG. 3A) and a lower plasma level of alanine aminotransferase (ALT), a biomarker of liver damage (FIG. 3C). 18-mer treatment showed reduced neutrophil infiltration into the liver and decreased plasma levels of tissue necrosis factor α (TNF-α) (FIGS. 3B and 6A), suggesting attenuation of local and systemic inflammation. 18-mer also decreased mortality following a lethal APAP overdose (600 mg kg$^1$), resulting in 90% survival at 96 hours compared to 42% survival in the control group (FIG. 3D). Hepatic glutathione (GSH) levels in APAP control and 18-mer treated mice were essentially the same during the course of the studies (FIG. 6B). GSH levels decrease as NAPQI forms (Tacke, 2015; Nam, 2017), therefore the data suggest that 18-mer does not affect the metabolic conversion of APAP to the cytotoxic intermediate, NAPQI. These results demonstrate that 18-mer ameliorates liver injury by reducing the inflammatory responses rather than by affecting APAP metabolism.

Figure 4A:
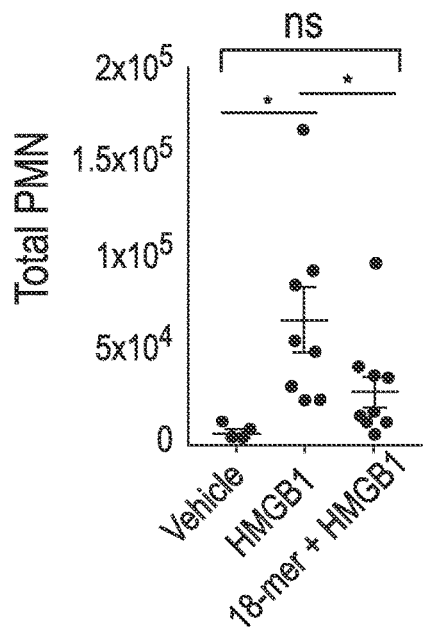
FIGS. 4A through 4D are graphical depictions of data showing 18-mer oligosaccharide targeting HMGB1 to decrease inflammation, FIG. 4E show symbolic structures of HS oligosaccharides.
Figure 4B:
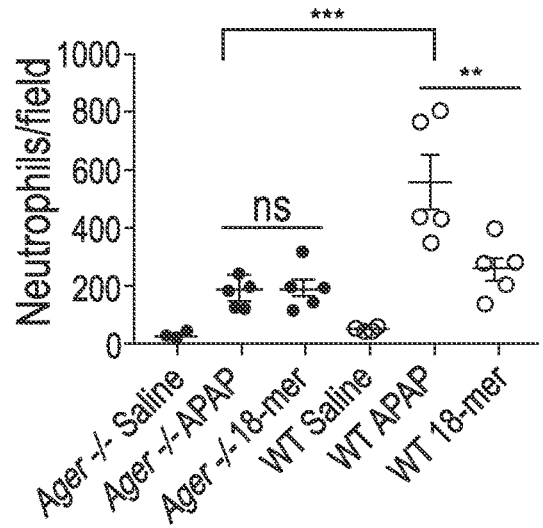

Two lines of evidence suggest that 18-mer targets HMGB1 to reduce inflammation after APAP overdose. First, we discovered that 18-mer diminishes the HMGB1-mediated neutrophil infiltration in two in vivo models. In an air pouch model, injection of recombinant HMGB1 induced extensive neutrophil infiltration (FIG. 4A), an effect that was significantly reduced by co-administration of 18-mer. 18-mer also reduced neutrophil infiltration in a peritonitis model induced by liver lysate (FIG. 6C), a process known to be mediated by HMGB1(4). Second, RAGE knockout mice, or Ager$^{-/-}$ mice, were used to demonstrate that 18-mer targets the HMGB1/RAGE axis. Because the interaction of HMGB1 and RAGE is essential for the pro-inflammatory response in APAP overdose (Huebener, 2015), the hepatoprotective effect of 18-mer is expected to be dependent on the presence of RAGE. Hepatic neutrophil infiltration was increased, and the increase was significantly greater in wild type (WT) than Ager$^{-/-}$ mice after APAP overdose (FIG. 4B). 18-mer treated Ager$^{-/-}$ mice failed to show a decrease in neutrophil infiltration, while WT mice responded to 18-mer treatment (FIG. 4B). Furthermore, 18-mer treatment in Ager$^{-/-}$ mice was incapable of lowering the ALT level (FIG. 6D). This data suggest that 18-mer lost its protective effect in the absence of RAGE.

Figure 4C:
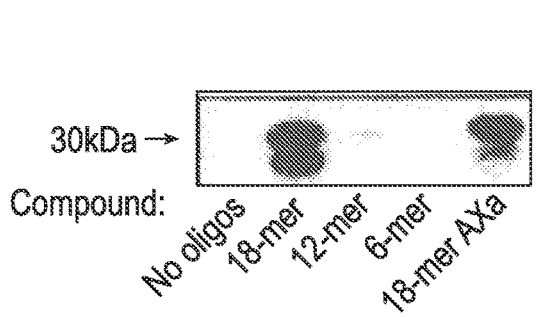
Figure 4D:
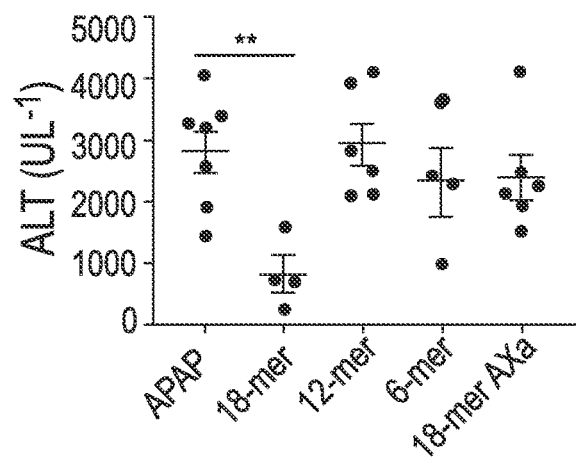
Figure 4E:
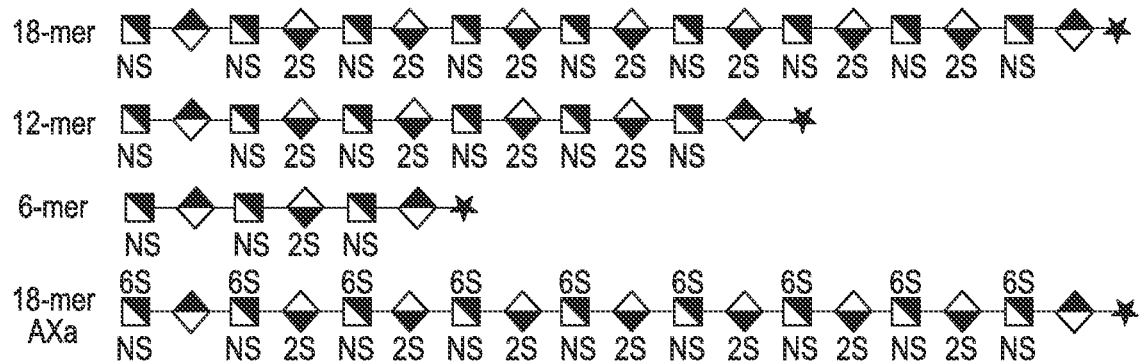
FIG. 4F is a legend for FIG. 4E.
Figure 4F:
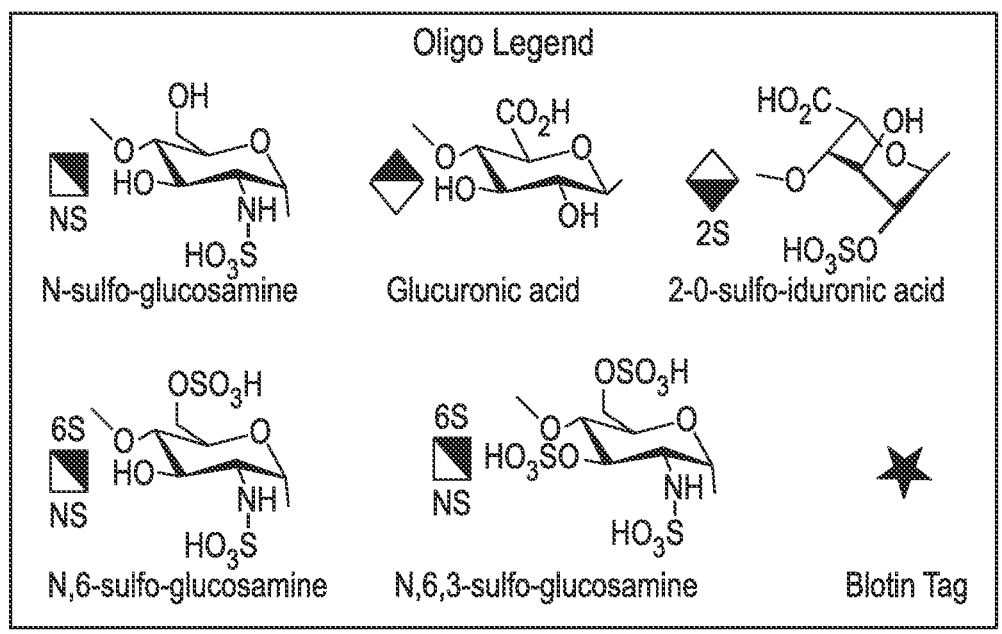
Figure 7:
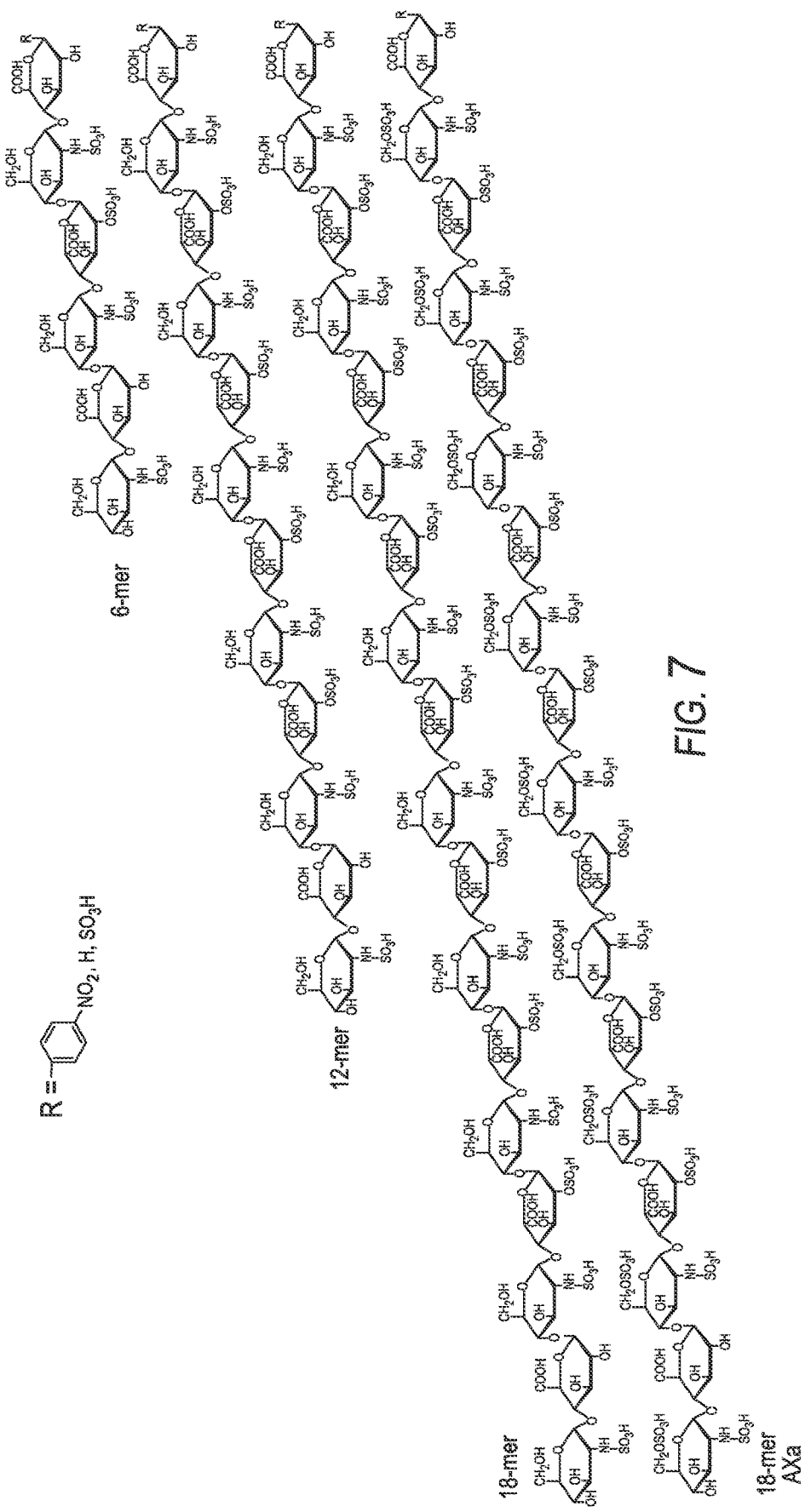
FIG. 7 is a schematic of the chemical structures of biotinylated and non-biotinylated oligosaccharides: 6-mer, 12-mer, 18-mer and 18-mer AXa.

Structure-activity relationship studies were conducted to examine binding to HMGB1 and protection in the APAP model using different forms of HS. Four biotinylated oligosaccharides were synthesized, including 6-, 12-, and two 18-mers (FIG. 4E) (for structures and characterization see FIG. 7). Among these, 6-, 12—and 18-mer varied only in chain length but not in sulfation pattern. These oligosaccharides are non-anticoagulant because they lack anti-factor Xa activity. 18-mer AXa is a highly sulfated anticoagulant octadecasaccharide that possesses potent anti-factor Xa activity (FIGS. 8A and 8B). The 18-mer and 18-mer AXa, but not the 6-mer or 12-mer, were observed to bind HMGB1 from mouse liver lysate, suggesting that there is a minimum chain length requirement for binding (FIG. 4C). The HMGB1-binding constants ($K_D$) were determined to be 186 nM (for 18-mer) and 65 nM (18-mer AXa) by surface plasmon resonance, yet only the 18-mer displayed the hepatoprotective effects as measured by ALT (FIG. 4D) and by neutrophil infiltration (FIG. 8C). It is apparent that the lack of hepatoprotection from the 6—and 12-mer correlates with the inability to bind HMGB1. However, the 18-mer AXa, while capable of binding HMGB1, also lacked hepatoprotection. This may be due to its anticoagulant activity since anticoagulant unfractionated heparin also lacked hepatoprotection after APAP-overdose (FIG. 8D). Kopec and colleagues have reported that fibrin is required to activate liver repair after APAP overdose (20). Administering 18-mer AXa reduces fibrin formation, and thus, results in loss of hepatoprotection.

Figure 5A:
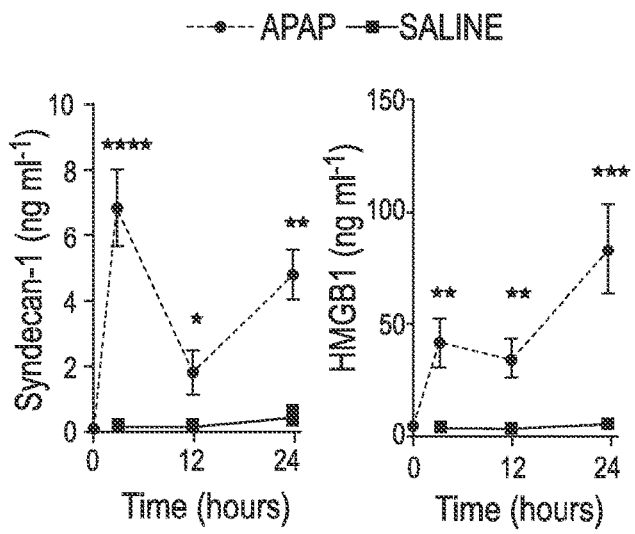
FIGS. 5A through 5D are graphical depictions of data showing the effects of delayed 18-mer oligosaccharide treatment on APAP overdose.
Figure 5B:
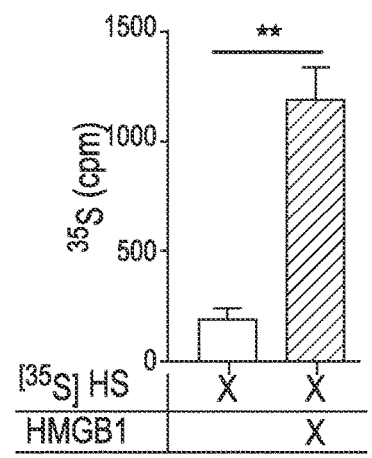
Figure 5C:
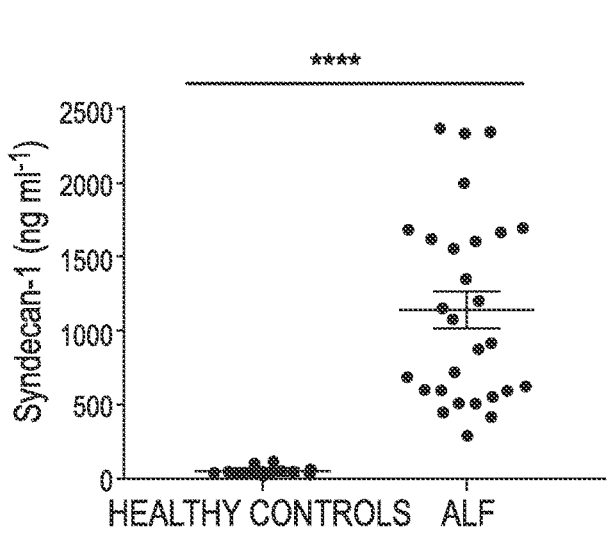
Figure 9A:
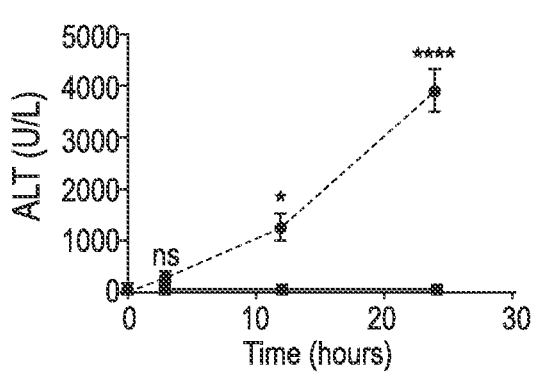
FIGS. 9A and 9B are graphical depictions of data showing APAP overdose results in increased levels of ALT, migrating neutrophils and shed syndecan-1.
Figure 9B:
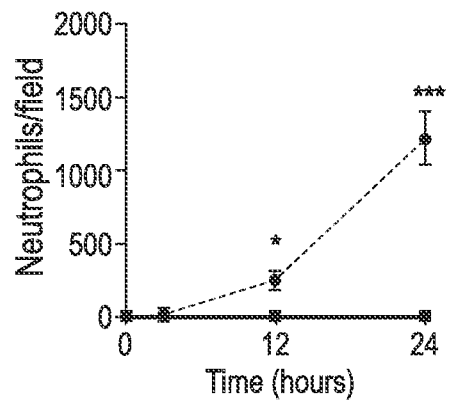
Figure 10A:
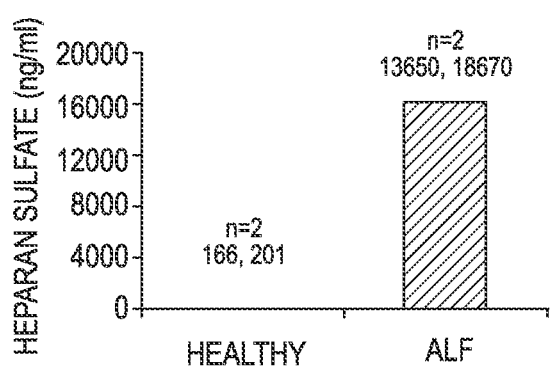
FIGS. 10A through 10C are graphical depictions of data based on the analysis of syndecan-1 from ALF patients and the plasma concentration of ALT and HMGB1 in ALF patients.
Figure 10B:
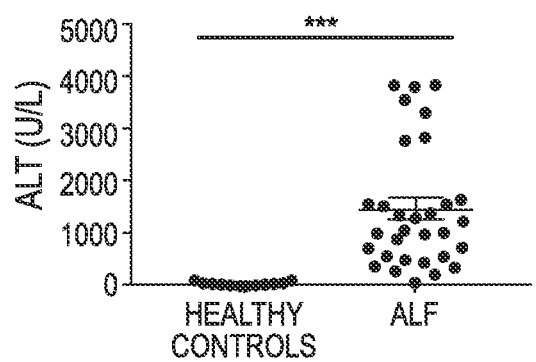
Figure 10C:
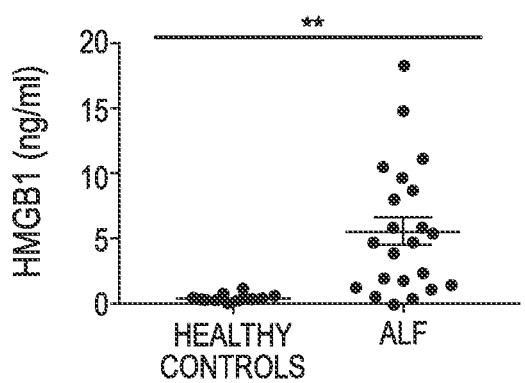

To further understand the protective role of 18-mer, the role of syndecan-1, a major HS proteoglycan present on hepatocytes, was investigated in response to APAP overdose. Syndecan-1 comprises a core protein attached with HS chains and is shed from the cell surface by matrix metalloproteases in pathological conditions (Park, 2000). Higher but fluctuating levels of plasma syndecan-1 were observed over a period of 24 hours after APAP overdose in mice (FIG. 5A). Concurrently, plasma levels of HMGB1 (FIG. 5A), ALT and hepatic neutrophil infiltration increased over time (FIGS. 9A and 9B). Loss of cell surface syndecan-1 was confirmed by immunostaining liver section. Using $^{35}$S-labeled HS from bovine kidney as a surrogate molecule for the HS chains on shed syndecan-1, we demonstrated that HMGB1 binds to HS (FIG. 5B), which is consistent with a previous report using HS from different sources (9). These results suggest that shed syndecan-1 binds to HMGB1 through its HS chains. A significant increase in plasma syndecan-1 levels was also observed from patients with APAP-induced ALF (FIG. 5C). Notably, shed syndecan-1 levels in APAP-ALF patients were about 200-fold higher than in APAP overdosed mice as measured by core protein analysis. HS chain analysis confirmed the heightened levels of shed syndecan-1 in ALF patients (FIG. 10A). HMGB1 and ALT in APAP-ALF patients were also higher than the healthy control group (FIGS. 10B and 10C), consistent with a previous report (22).

The relationship between syndecan-1 shedding and HMGB1 release in humans and mice after APAP overdose underscores an endogenous protective pathway. Syndecan-1 sheds after the initial insult and neutralizes the pro-inflammatory activities of HMGB1, thereby limiting sterile inflammation. Indeed, syndecan-1$^{-/-}$ mice are more susceptible to APAP-induced ALF than WT animals (Nam, 2017). During extensive APAP damage, it is likely that shed syndecan-1 is inadequate to neutralize all HMGB1, and the addition of 18-mer, a mimetic of HS on syndecan-1, provides further protection.

Figure 5D:
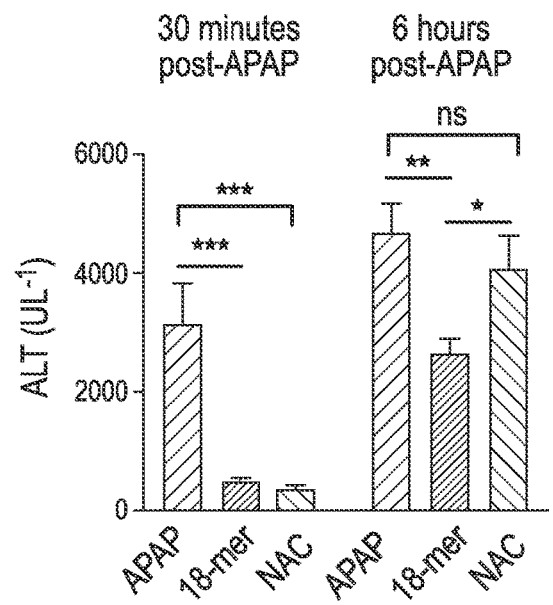

Since sterile inflammation occurs after NAPQI-induced cell damage, we examined the possibility of further delaying 18-mer treatment after APAP overdose. N-acetyl-cysteine (NAC) is a NAPQI-neutralizing antioxidant that is the standard of care for the treatment of APAP overdose. However, NAC treatment is only effective if given within 8 hours of APAP ingestion (Bailey, 2016). While NAC loses its protective effect when administered at six hours post-APAP in mice, the 18-mer is still able to decrease ALT (FIG. 5D). These data suggest that 18-mer treatment has a potential advantage for late-presenting APAP overdose patients by providing a wider therapeutic window.

Example 8

Conclusions

The use of synthetic HS to treat APAP-induced ALF by targeting HMGB1-mediated sterile inflammation is disclosed herein. The availability of homogeneous oligosaccharides has made it possible to identify candidate targets and compounds underlying this effect. In addition to neutralizing HMGB1, HS of syndecan-1 can also activate liver repair and modulate the activity of chemokines. 18-mer could also contribute to these functions. HS is well-tolerated by patients (Shriver, 2004) and unfractionated heparin, a highly sulfated form of HS, has been used as an anticoagulant for nearly a century (Szajek, 2016). Now, the synthesis of HS oligosaccharides can be achieved on a large scale and in a cost-effective manner. HMGB1-neutralizing synthetic oligosaccharides should offer a promising therapeutic approach for ALF. Because HMGB1 has been implicated in diverse disease states including cancers, stroke and arthritis (Venereau, 2016), novel HS-based therapeutics provide promising opportunities as inhibitors of HMGB1.

REFERENCES

All references listed herein including but not limited to all patents, patent applications and publications thereof, scientific journal articles, and database entries (e.g., GEN-BANK® database entries and all annotations available therein) are incorporated herein by reference in their entireties to the extent that they supplement, explain, provide a background for, or teach methodology, techniques, and/or compositions employed herein.

1. L. Zitvogel, O. Kepp, G. Kroemer, Decoding cell death signals in inflammation and immunity. *Cell* 140, 798-804 (2010).
2. G. Y. Chen, G. Nuñez, Sterile inflammation: sensing and reacting to damage. *Nat. Immunol.* 10, 826-837 (2010).
3. M. E. Bianchi et al., High-mobility group box 1 protein orchestrates responses to tissue damage via inflammation, innate and adaptive immunity, and tissue repair. *Immunol. Rev.* 280, 74-82 (2017).
4. P. Huebener et al., The HMGB1/RAGE axis triggers neutrophil-mediated injury amplification following necrosis. *J. Clin. Invest.* 125, 539-550 (2015).

5. K. J. Heard, Acetylcystein for acetaminophen poisoning. *N. Eng. J. Med.* 359, 285-292 (2008).
6. W. M. Lee, Acetaminophen toxicity: changing perceptions on a social/medical issue. *Hepatology* 46, 966-970 (2007).
7. M. Blieden, L. C. paramore, D. Shah, R. Ben-Joseph, A perspective on the epidemiology of acetaminophen exposure and toxicity in the United States. *Expert Rev. Clin. Pharmacol.* 7, 341-348 (2014).
8. F. Tacke, J. C. Mossanen, Acetaminophen-induced acute liver injury in mice. *Lab. Anim.* 49, 30-36 (2015).
9. D. Xu, J. Young, D. Song, J. D. Esko, Heparan sulfate is essential for high mobility group protein 1 (HMGB1) signaling by the receptor for advanced glycation end products (RAGE). *J. Biol. Chem.* 286, 41736-41744 (2011).
10. A. E. Proudfoot et al., Glycosaminoglycan binding and oligomerization are essential for the in vivo activity of certain chemokines. *Proc. Natl. Acad. Sci. USA* 100, 1885-1890 (2003).
11. L. Wang, M. Fuster, P. Srramarao, J. D. Esko, Edothelial heparan sulfate deficiency impairs L-selectin- and chemokine-mediated neutrophil trafficking during inflammatory responses. *Nat. Immunol.* 6, 902-910 (2005).
12. J. Axelsson et al., Inactivation of heparan sulfate 2-O-sulfotransferase accentuates neutrophil infiltration during acute inflammation in mice. *Blood* 120, 1742-1751 (2013).
13. M. Sarris et al., Inflammatory chemokines direct and restrict leukocyte migration within live tissues as glycan-bound gradients. *Curr. Biol.* 22, 2375-2382 (2012).
14. C. Gama et al., Sulfation patterns of glycosaminoglycans encode molecular recognition and activity. *Nat. Chem. Biol.* 2, 467-473 (2006).
15. J. Liu, R. J. Linhardt Chemoenzymatic synthesis of heparan sulfate and heparin. *Nat. Prod. Rep.* 31, 1676-1685 (2014).
16. Y. Xu et al., Chemoenzymatic synthesis of homogeneous ultra-low molecular weight heparin. *Science* 334, 498-501 (2011).
17. Y. Xu et al., Homogeneous and reversible low-molecular weight heparins with reversible anticoagulant activity. *Nat. Chem. Biol.* 10, 248-250 (2014).
18. Y. Xu et al., Synthetic oligosaccharides can replace animal-sourced low-molecular weight heparins. *Sci. Transl. Med.* 9, eaan5954 (2017).
19. E. J. Nam et al., Syndecan-1 Limits the Progression of Liver Injury and Promotes Liver Repair in Acetaminophen-Induced Liver Injury. *Hepatology*, doi: 10.1002/hep.29265 (2017).
20. A. Kopec et al., Fibrin(ogen) drives repair after acetaminophen-induced liver injury via leukocyte aMb2 integrin-dependent upregulation of Mmp12. *J. Hepatol.* 66, 787-797 (2017).
21. P. W. Park, O. Reizes, M. Bemfield, Cell surface heparan sulfate proteoglycans: selective regulators of ligand-receptor encounters. *J. Biol. Chem.* 275, 29923-29926 (2000).
22. D. J. Antoine et al., Mechanistic biomarkers provide early and sensitive detection of acetaminophen-induced acute liver injury at first presentation to hospital. *Hepatology* 68, 777-787 (2013).
23. G. P. Bailey et al., Delays during the administration of acetylcysteine for the treatment of paracetamol overdose. *Br. J. Clin. Pharmacol.* 62, 1358-1363 (2016).
24. K. C. Wildhagen et al., Nonanticoagulant heparin prevents histone-mediated cytotoxicity in vitro and improves survival in sepsis. *Blood* 123, 1098-1101 (2014).
25. Y. Monneau, F. Arenzana-Seisdedos, H. Lortat-Jacob, The sweet spot: how GAGs help chemokines guide migrating cells. *J. Leukoc. Biol.* 99, 935-953 (2016).
26. P. Lundback et al., A novel high mobility group box 1 neutralizing chimeric antibody attenuates drug-induced liver injury and postinjury inflammation in mice. *Hepatology* 64, 1699-1710 (2016).
27. T. Yamamoto, Y. Tajima, HMGB1 is a promising therapeutic target for acute liver failure. *Expert Rev. Gatroenterol. Hepatol.* 11, 673-682 (2017).
28. Z. Shriver, S. Raguram, R. Sasisekharan, Glycomics: A pathway to a class of new and improved therapeutics. *Nat Rev Drug Discov* 3, 863-873 (2004).
29. A. Szajek et al., The US regulatory and pharmacopeia responses to the global heparin contamination crisis. *Nat. Biotechnol.* 34, 625-630 (2016).
30. E. Venereau et al., HMGB1 as biomarker and drug target. *Pharmacol. Res.* 111, 534-544 (2016).
31. P. Hsieh, Y. Xu, D. A. Keire, J. Liu, Chemoenzymatic synthesis and structural characterization of 2-O-sulfated glucuronic acid containing heparan sulfate hexasaccharides. *Glycobiology* 24, 681-692 (2014).
32. B. Liliensiek et al., Receptor for advanced glycation end products (RAGE) regulates sepsis but not the adaptive immune response. *J. Clin. Invest.* 113, 1641-1650 (2004).
33. PCT Publication No. WO2012/088416, published Jun. 28, 2012
34. Published U.S. Patent Application No. US2013/0296540, published Nov. 7, 2013
35. PCT Publication No. WO2014204929, published Dec. 24, 2014
36. Published U.S. Patent Application No. US2016/0122446, published May 5, 2016
37. Xu, Y., Chandarajoti, K., Zhang, X., Pagadala, V., Dou, W., Hoppensteadt, D. M., Sparkenbaugh, E., Colley, B., Daily, S., Key, N., Severynse-Stevens, D., Fareed, J., Linhardt, R. J., Pawlinksi, R., and Liu, J. (2017) Synthetic oligosaccharides can replace animal-sourced low-molecular weight heparins *Sci. Transl. Med.*, 9, eaan5954.
38. Xu, Y, Cai, C., Chandarajoti, K, Li, L., Hsieh, P., Pham, T., Sparkenbaugh, E. M., Sheng, J., Key, N., Pawlinski, R., Harris, E., Linhardt, R. J., and Liu, J. (2014) Homogeneous and reversible low-molecular weight heparins with reversible anticoagulant activity. *Nat. Chem Biol.* 10: 248-250.
39. Renpeng Liu, Yongmei Xu, Miao Chen, Michel Weiwer, Xianxuan Zhou, Arlene S. Bridges, Paul L. DeAngelis, Qisheng Zhang, Robert J. Linhardt and Jian Liu (2010) Chemoenzymatic design of heparan sulfate oligosaccharides *J. Biol. Chem.* 285:34240-34249
40. Xu, D., Moon, A. F., Song, D., Pedersen, L. C. and Uu, J. (2008) Engineering the sulfotransferases to modify heparan sulfate *Nat. Chem. Biol.* 4: 200-202.

It will be understood that various details of the presently disclosed subject matter may be changed without departing from the scope of the presently disclosed subject matter. Furthermore, the foregoing description is for the purpose of illustration only, and not for the purpose of limitation.

-continued
Structure 5 (NS6S2S)
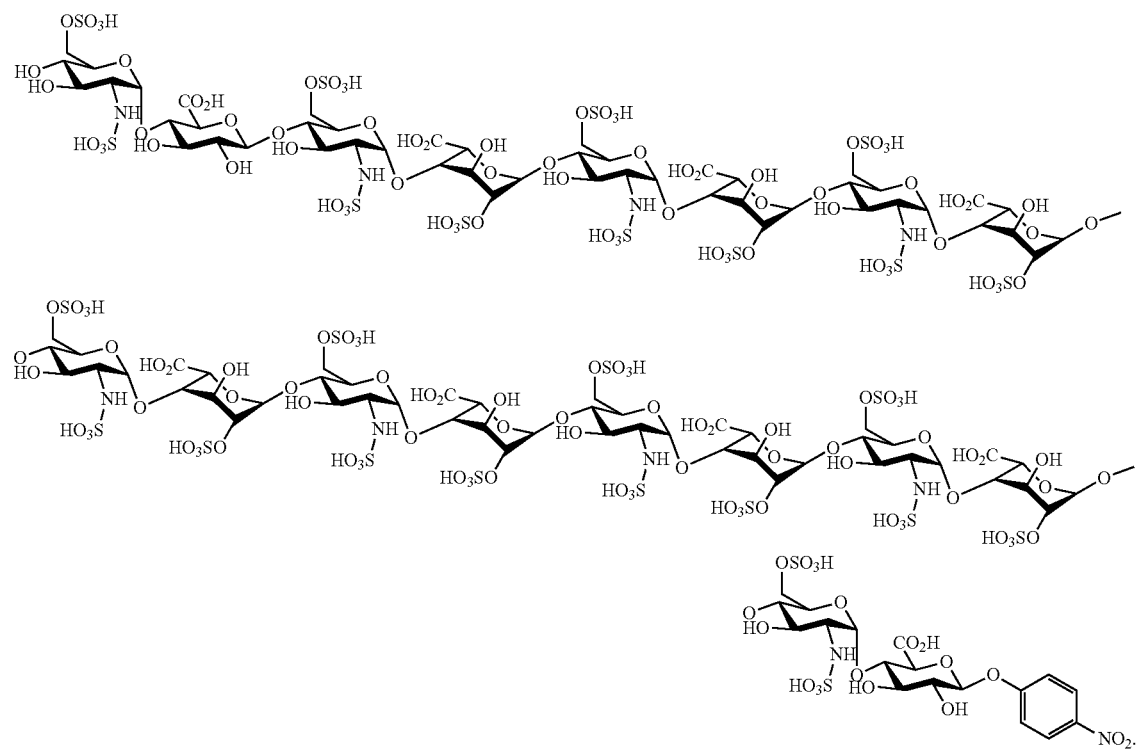

What is claimed is:

1. A method of treating a subject, the method comprising:
providing a subject to be treated, wherein the subject is suffering from inflammation; and
administering to the subject a small molecule compound having an anti-inflammatory property, the small molecule compound comprising a non-anticoagulant heparan sulfate oligosaccharide molecule comprising one of the following structural formulas:

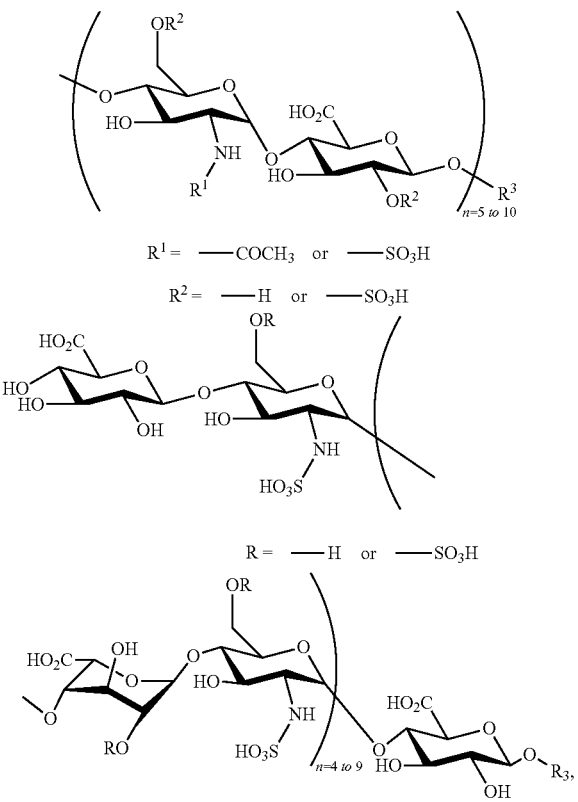

wherein $R^3$ is H or a detectable tag.

2. The method of claim 1, wherein the subject suffers from any injury resulting in increased inflammation.

3. The method of claim 1, wherein the subject suffers from liver injury.

4. The method of claim 1, wherein the subject in need of treatment is a subject suffering from an overdose of Paracetamol (APAP).

5. The method of claim 1, wherein the subject in need of treatment is a human subject.

6. The method of claim 1, wherein the small molecule compound comprises a disaccharide structure unit as shown:

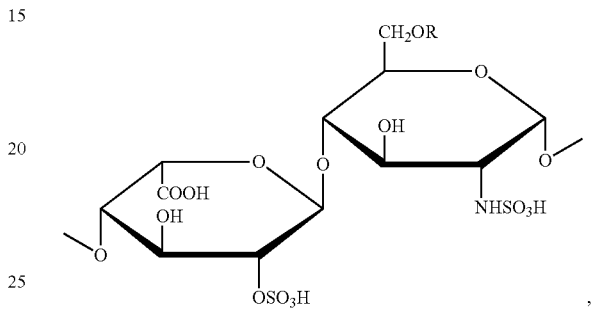

wherein R=—H or —SO₃H.

7. The method of claim 6, wherein the small molecule compound comprising a disaccharide structure unit is selected from the group consisting of non-anticoagulant heparin, non-anticoagulant low-molecular weight heparin, and O-desulfated heparin (ODSH).

8. The method of claim 1, wherein the oligosaccharide molecule comprises about 10 to about 20 saccharide units, or about 12 to about 18 saccharide units.

9. The method of claim 1, wherein the oligosaccharide molecule comprises about 18 saccharide units.

10. The method of claim 1, wherein the oligosaccharide molecule comprises one of the following structures:

Structure 1 (NAc)

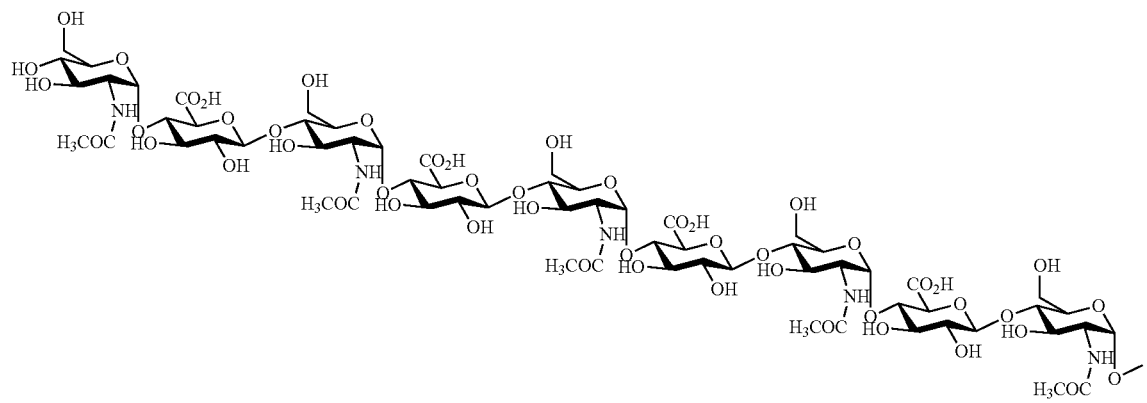

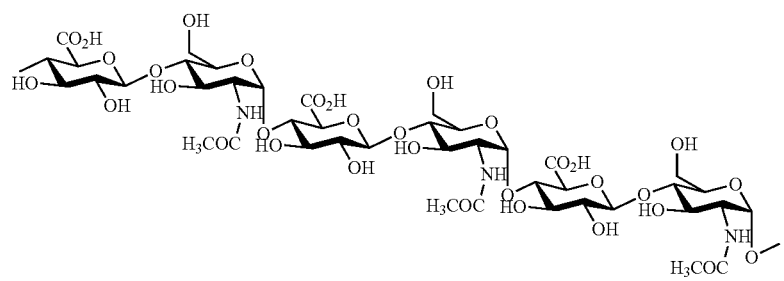
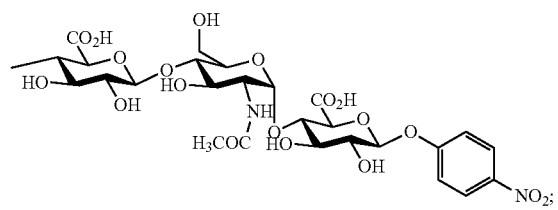
Structure 2 (NS)
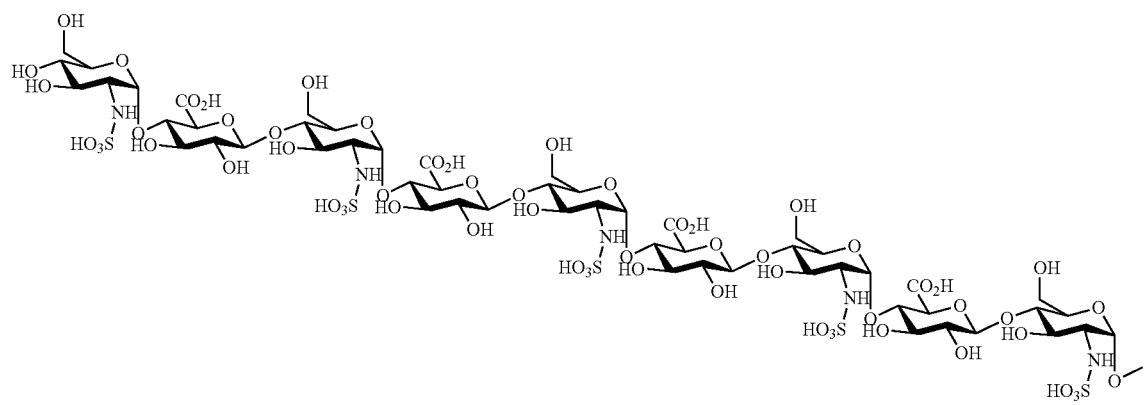
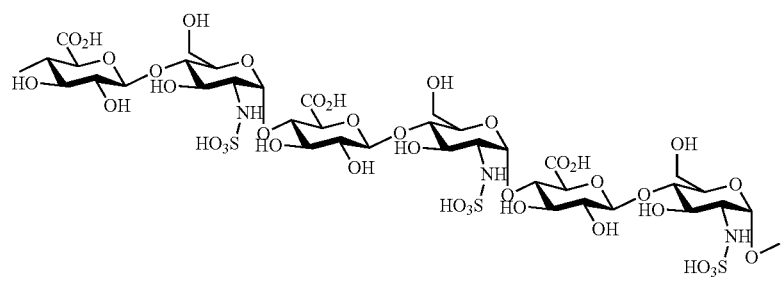
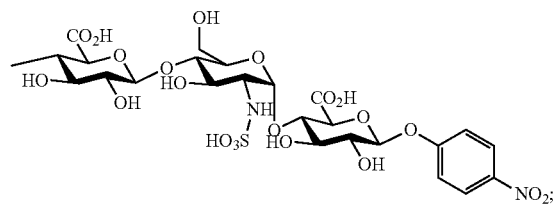

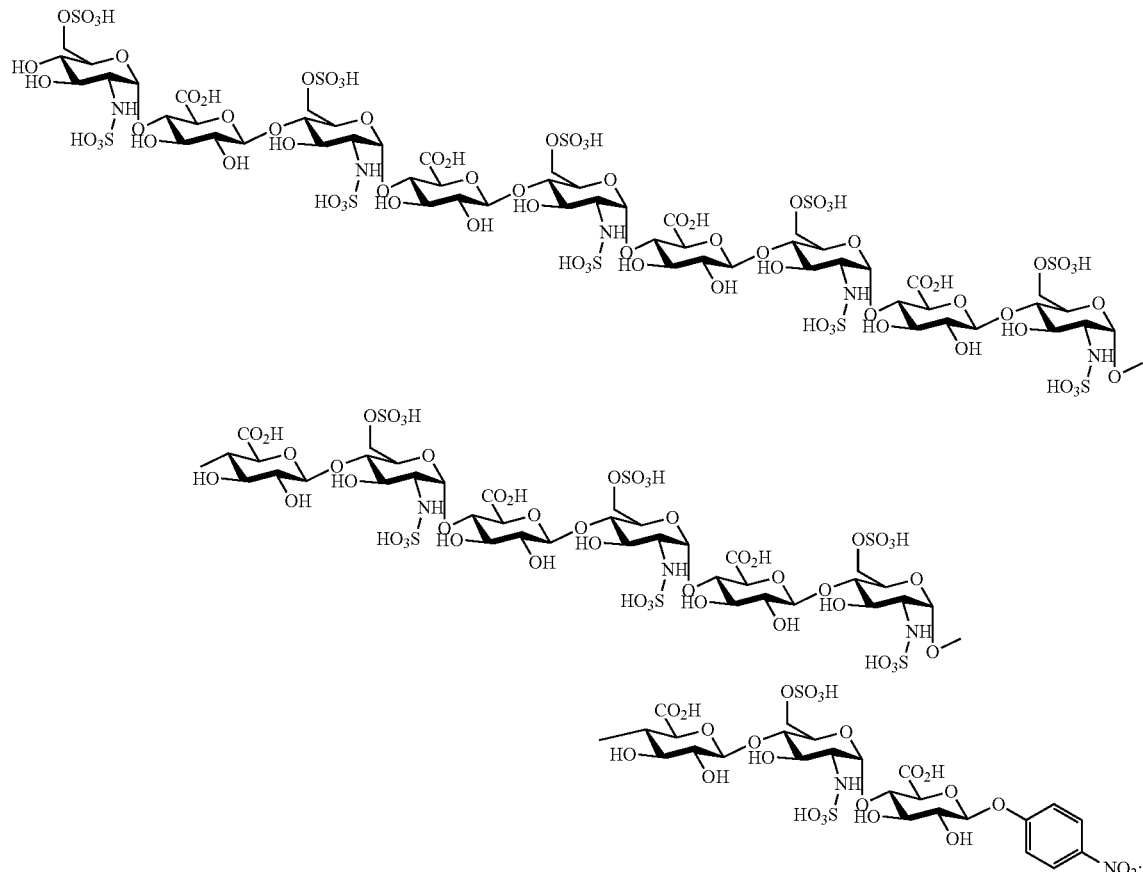
Structure 3 (NS6S)
Structure 4 (NS2S)
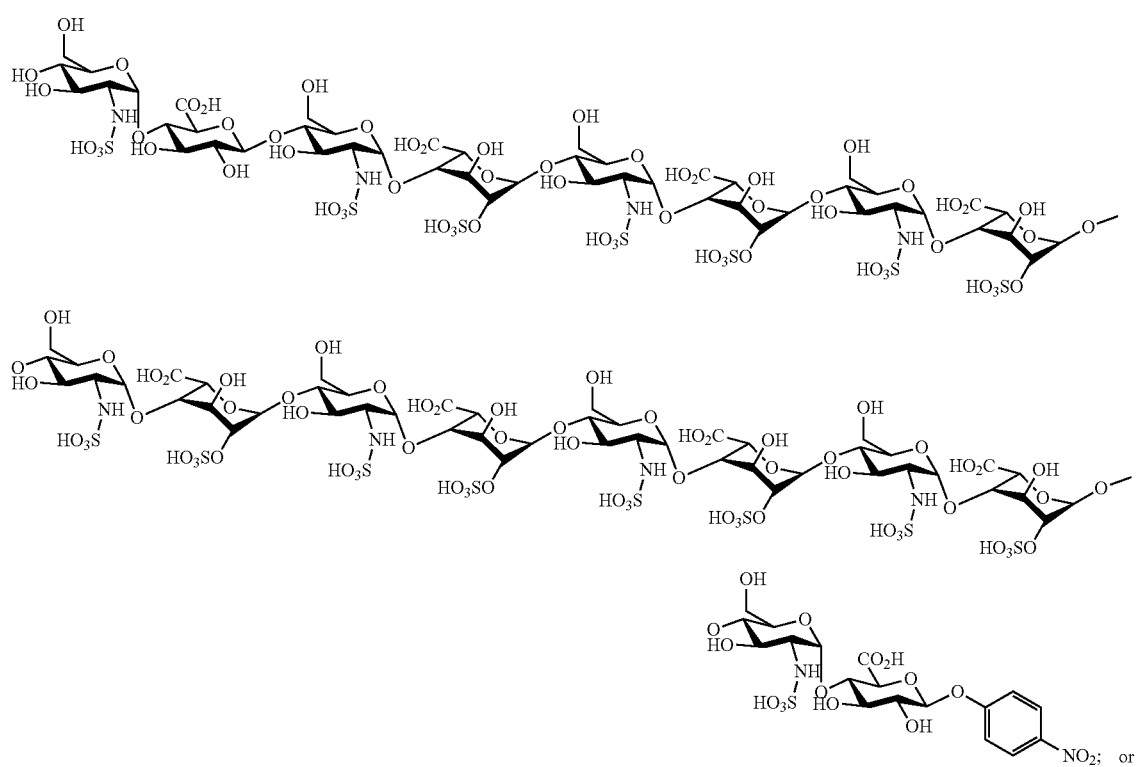

-continued

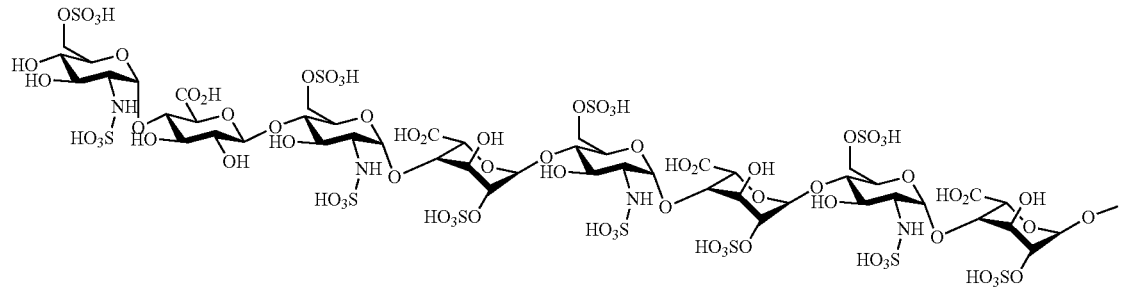

Structure 5 (NS6S2S)

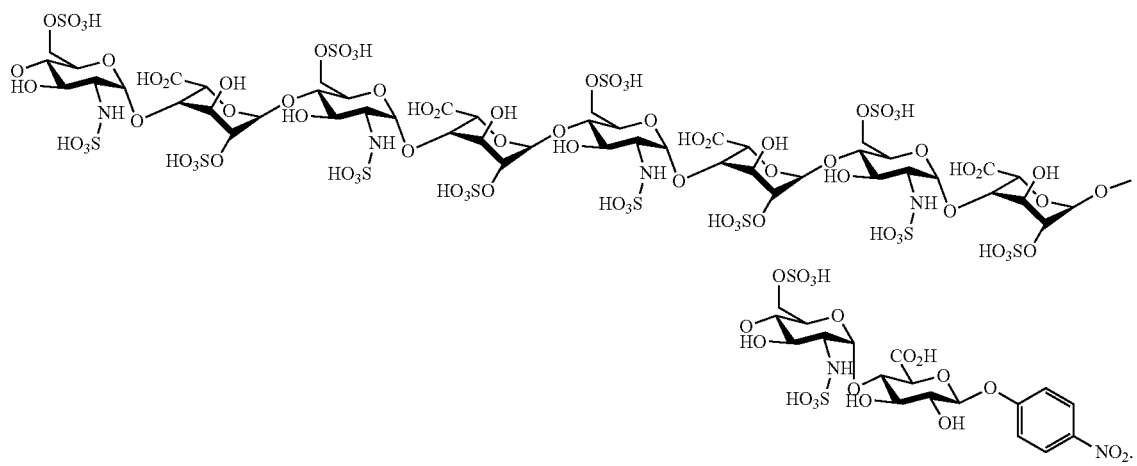

11. The method of claim 1, wherein administration of the oligosaccharide molecule decreases neutrophil infiltration in the subject.

12. The method claim 1, wherein administration of the oligosaccharide molecule decreases inflammation in the subject.

13. The method of claim 1, wherein administration of the oligosaccharide molecule protects against liver damage and multi-organ system failure in the subject.

14. The method claim 1, wherein the subject to be treated suffers from drug-induced inflammation.

15. A method of treating Paracetamol (APAP) overdose in a subject, the method comprising:

providing a subject in need of treatment for APAP overdose;

administering to the subject a small molecule compound having an anti-inflammatory property, the small molecule compound comprising a non-anticoagulant heparan sulfate oligosaccharide molecule comprising one of the following structural formulas:

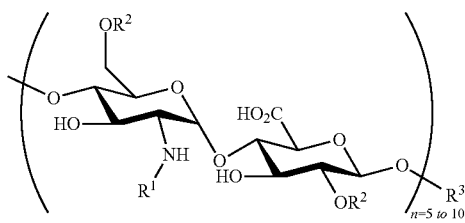

$R^1 =$ —COCH$_3$ or —SO$_3$H $R^2 =$ —H or —SO$_3$H

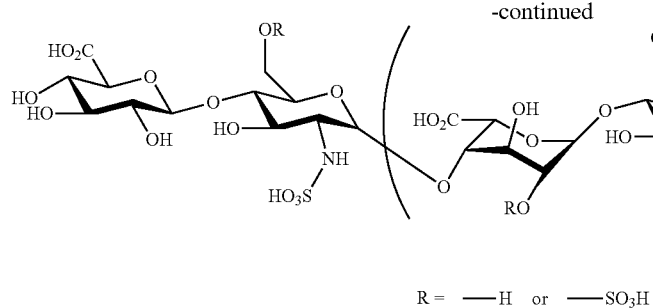
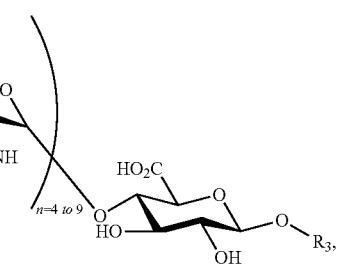

R = —H or —SO₃H wherein R³ is H or a detectable tag and wherein damage from the APAP overdose in the subject is mitigated.

16. The method of claim 15, wherein the treatment for the APAP overdose in the subject is effective between 0 hours and 24 hours after the overdose, or at least within 12 hours after the overdose.

17. The method of claim 15, wherein the treatment for the APAP overdose in the subject comprises protection against liver injury and/or multi-organ system failure.

18. The method of claim 15, wherein the treatment for the APAP overdose in the subject comprises a decrease in neutrophil infiltration in the subject.

19. The method of claim 15, wherein the treatment for the APAP overdose in the subject comprises blocking an interaction between a high mobility group box 1 (HMGB1) protein and a receptor for advanced glycation endproducts (RAGE).

20. The method of claim 15, wherein the small molecule compound comprises a disaccharide structure unit as shown:

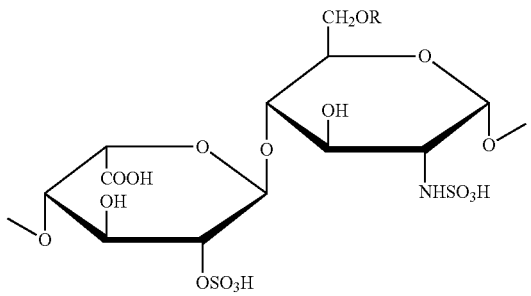

wherein R=—H or —SO₃H.

21. The method of claim 20, wherein the small molecule compound comprising a disaccharide structure unit is selected from the group consisting of non-anticoagulant heparin, non-anticoagulant low-molecular weight heparin, and O-desulfated heparin (ODSH).

22. The method of claim 15, wherein the oligosaccharide molecule comprises about 10 to about 20 saccharide units, or about 12 to about 18 saccharide units.

23. The method claim 15, wherein the oligosaccharide molecule comprises about 18 saccharide units.

24. A method of treating Paracetamol (APAP) overdose in a subject, the method comprising:

providing a subject in need of treatment for APAP overdose;

administering to the subject a non-anticoagulant heparan sulfate oligosaccharide molecule having an anti-inflammatory property, wherein damage from the APAP overdose in the subject is mitigated, and wherein the oligosaccharide molecule comprises one of the following:

Structure 1 (NAc)

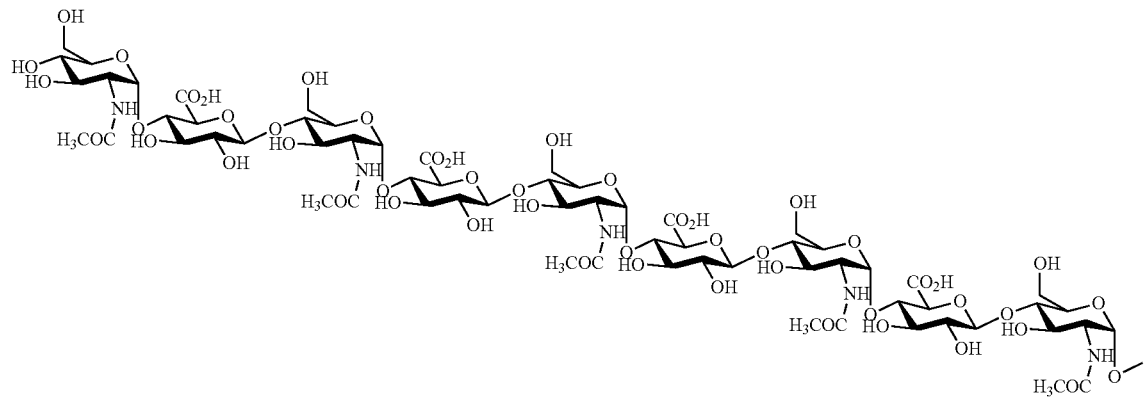

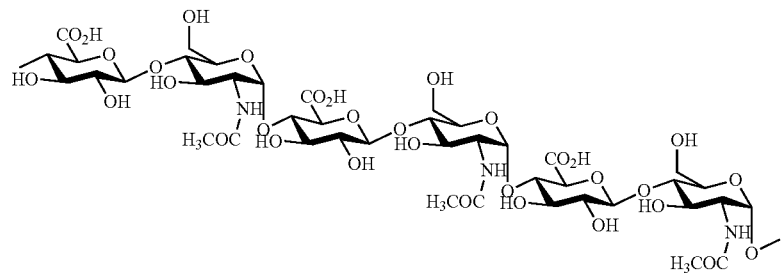
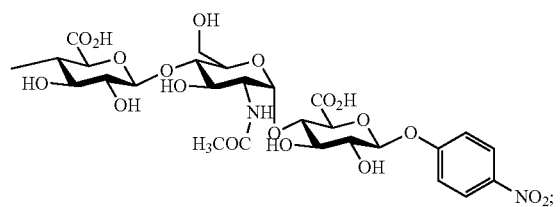
Structure 2 (NS)
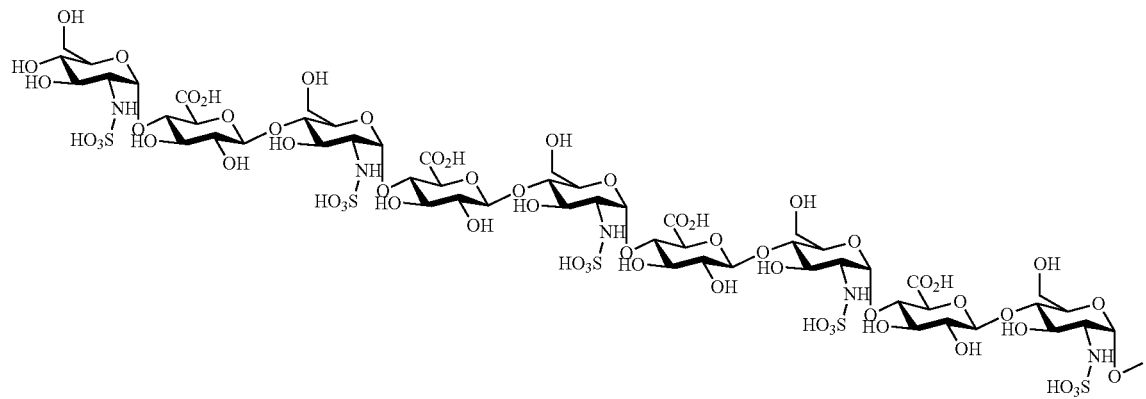
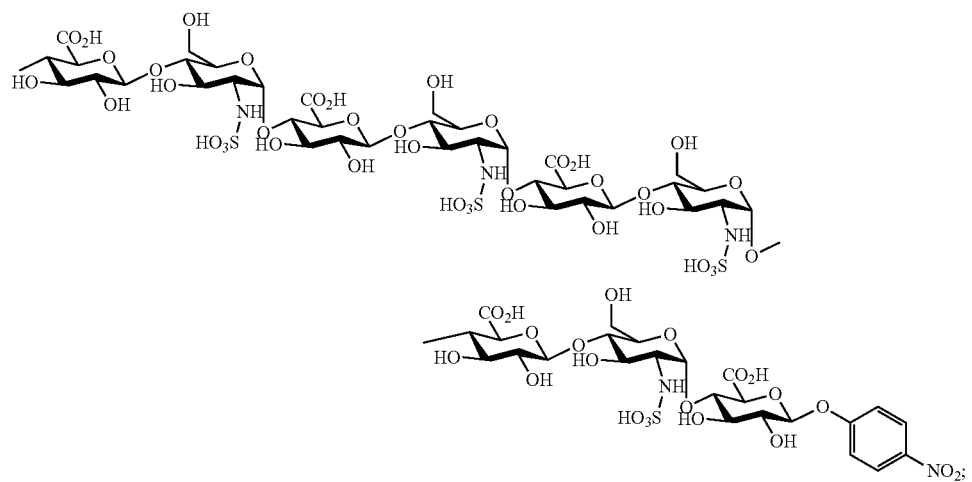

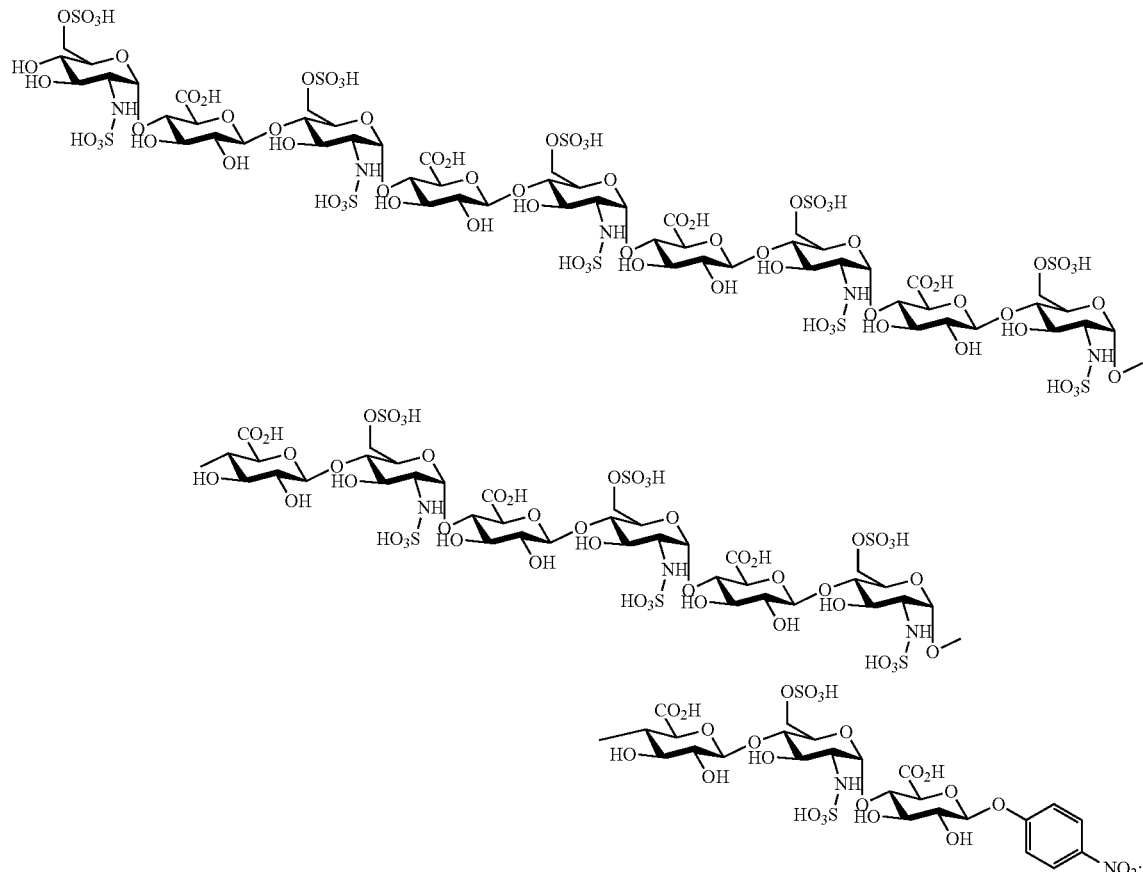
Structure 3 (NS6S)
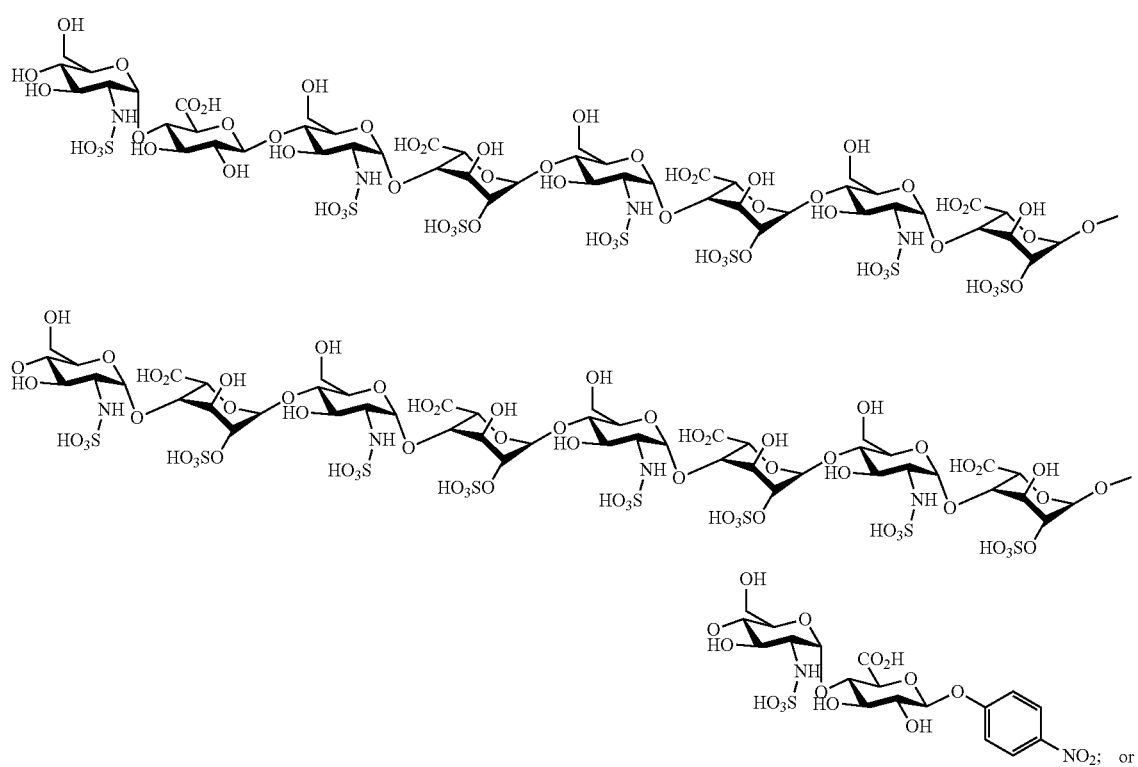
Structure 4 (NS2S)